(12) United States Patent
Messing et al.

(10) Patent No.: US 9,376,423 B2
(45) Date of Patent: Jun. 28, 2016

(54) PKC-EPSILON INHIBITORS

(71) Applicant: The Regents of the University of California, Oakland, CA (US)

(72) Inventors: Robert Owen Messing, Emeryville, CA (US); Michael A. Pleiss, Sunnyvale, CA (US); Jon D. Levine, San Francisco, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/321,727

(22) Filed: Jul. 1, 2014

(65) Prior Publication Data

US 2015/0005349 A1    Jan. 1, 2015

Related U.S. Application Data

(60) Division of application No. 13/340,406, filed on Dec. 29, 2011, now Pat. No. 8,785,648, which is a continuation-in-part of application No. 13/205,373, filed on Aug. 8, 2011, now abandoned.

(60) Provisional application No. 61/372,400, filed on Aug. 10, 2010.

(51) Int. Cl.
| | | |
|---|---|---|
| *A61K 31/44* | (2006.01) | |
| *C07D 213/72* | (2006.01) | |
| *C07D 409/12* | (2006.01) | |
| *C07D 213/75* | (2006.01) | |
| *C07D 405/12* | (2006.01) | |
| *C12N 9/99* | (2006.01) | |
| *C07D 405/14* | (2006.01) | |
| *C07D 401/12* | (2006.01) | |
| *C07D 409/14* | (2006.01) | |
| *C07D 471/04* | (2006.01) | |

(52) U.S. Cl.
CPC ............ *C07D 409/12* (2013.01); *C07D 213/75* (2013.01); *C07D 401/12* (2013.01); *C07D 405/12* (2013.01); *C07D 405/14* (2013.01); *C07D 409/14* (2013.01); *C07D 471/04* (2013.01); *C12N 9/99* (2013.01)

(58) Field of Classification Search
None
See application file for complete search history.

(56) References Cited

U.S. PATENT DOCUMENTS

| | | | |
|---|---|---|---|
| 4,997,834 | A | 3/1991 | Muro et al. |
| 5,698,578 | A | 12/1997 | Heath et al. |
| 5,739,322 | A | 4/1998 | Heath et al. |
| 5,962,504 | A | 10/1999 | Kozikowski et al. |
| 6,057,440 | A | 5/2000 | Heath et al. |
| 6,080,784 | A | 6/2000 | Driedger et al. |
| 6,284,784 | B1 | 9/2001 | Kozikowski et al. |
| 6,369,086 | B1 | 4/2002 | Davis et al. |
| 6,369,087 | B1 | 4/2002 | Whittle et al. |
| 6,372,733 | B1 | 4/2002 | Caldwell et al. |
| 6,372,778 | B1 | 4/2002 | Tung et al. |
| 6,376,467 | B1 | 4/2002 | Messing et al. |
| 2002/0164389 | A1 | 11/2002 | Crandall |
| 2003/0118529 | A1 | 6/2003 | Rotenberg et al. |
| 2003/0134774 | A1 | 7/2003 | Steinberg et al. |
| 2003/0166678 | A1 | 9/2003 | Kwiatkowski et al. |
| 2003/0176423 | A1 | 9/2003 | He et al. |
| 2003/0176424 | A1 | 9/2003 | He et al. |
| 2003/0199423 | A1 | 10/2003 | Gallatin et al. |

FOREIGN PATENT DOCUMENTS

| | | |
|---|---|---|
| DE | 197 40 384 A1 | 3/1999 |
| EP | 0 370 498 A2 | 5/1990 |
| WO | WO-94/18328 | 8/1994 |
| WO | WO-96/40894 | 12/1996 |
| WO | WO-97/15575 | 5/1997 |
| WO | WO-99/33792 | 7/1999 |
| WO | WO-99/33793 | 7/1999 |
| WO | WO-99/33795 | 7/1999 |
| WO | WO-99/33815 | 7/1999 |
| WO | WO-00/01415 | 1/2000 |
| WO | WO-00/01805 | 1/2000 |
| WO | WO-01/30331 A2 | 5/2001 |
| WO | WO-01/81633 A1 | 11/2001 |
| WO | WO-01/83449 A2 | 11/2001 |
| WO | WO-02/22709 A1 | 3/2002 |
| WO | WO-02/087417 A2 | 11/2002 |
| WO | WO-02/102232 A2 | 12/2002 |
| WO | WO-02/103000 A2 | 12/2002 |
| WO | WO-03/004612 A2 | 1/2003 |
| WO | WO-03/082859 A1 | 10/2003 |
| WO | WO-03/089456 A2 | 10/2003 |

(Continued)

OTHER PUBLICATIONS

Silva, T. Mini Rev Med Chem 2005 vol. 5 pp. 893-914.*
Basta et al., "Sequence and expression of human protein kinase C-epsilon," Biochimica et Biophysica Acta., (1992), 1132:154-160.
Castrillo et al., "Protein Kinase C epsilon is Required for Macrophage Activation and Defense Against Bacterial Infection," J. Exp. Med., (2001), 194(9):1231-1242.
Donnelly et al., "Mechanisms of Insulin Resistance and New Pharmacological Approaches to Metabolism and Diabetic Complications," Clinical and Experimental Pharmacology and Physiology, (1998), 25:79-87.

(Continued)

*Primary Examiner* — Heidi Reese
(74) *Attorney, Agent, or Firm* — Foley & Lardner LLP

(57) ABSTRACT

The present invention relates to new AGC kinase inhibitors, in particular to compounds of Formula I or II or a stereoisomer, tautomer, racemic, metabolite, pro- or pre-drug, salt, hydrate, or solvate thereof, wherein Ar, Cy, $R^1$, $R^3$, p and n have the meaning defined in the claims. In particular, the present invention relates to more specifically AGC kinases inhibitors, compositions, in particular pharmaceuticals, comprising such inhibitors, and to uses of such inhibitors in the treatment and prophylaxis of disease.

9 Claims, 24 Drawing Sheets

(56) References Cited

FOREIGN PATENT DOCUMENTS

| WO | WO-03/089457 A3 | 10/2003 |
|---|---|---|
| WO | WO-2005/082367 | 9/2005 |
| WO | WO-2007/006546 | 1/2007 |
| WO | WO-2007/042321 | 4/2007 |
| WO | WO-2008/049919 | 5/2008 |

OTHER PUBLICATIONS

Goodman and Gilman's The Pharmacological Basis of Therapeutics, 8th Edition, "Biotransformation of Drugs" (1992) 13-18.

Nishizuka, N., "Intracellular Signaling by Hydrolysis of Phospholipids and Activation of Protein Kinase C," Science, (1992), 258(5082):607-614.

PCT International Search Report and Written Opinion for PCT/US2014/045164 dated Apr. 24, 2015.

PubChem, CID 57262067, 2012 (https://pubchem.ncbi.nlm.nih.gov/compound/57262067#section=Top).

Qu et al., "Tissue and isoform-selective activation of protein kinase C in insulin-resistance obese Zucker rats—effects of feeding," J. Endocrinology, (1999), 162:207-214.

Selbie et al., "Molecular Cloning and Characterization of PKCiota, an Atypical Isoform of Protein Kinase C Derived from Insulin-secreting Cells," J. Biological Chemistry, (1993), 268(32):24296-24302.

Shafrir et al., "Nutritionally Induced Resistance and Receptor Defect Leading to Beta-Cell Failure in Animal Models," Annals New York Academy of Sciences, (1999), 892:223-241.

Soh et al., "Novel Roles of Specific Isoforms of Protein Kinase C in Activation of the c-fos Serum Response Element," Molecular and Cellular Biology, (1999), 19(2):1313-1324.

* cited by examiner

PKC-EPSILON INHIBITORS

CROSS REFERENCE TO RELATED APPLICATIONS

This application is a divisional application of U.S. patent application Ser. No. 13/340,406, filed on Dec. 29, 2011, which is a continuation in part of U.S. patent application Ser. No. 13/205,373, filed on Aug. 8, 2011, and claims the benefit under 35 U.S.C. §119(e) of U.S. provisional application No. 61/372,400, filed on Aug. 10, 2010, all of which are incorporated herein by reference in their entirety.

FIELD OF THE INVENTION

The present invention relates to new kinase inhibitors, compositions, in particular pharmaceuticals, comprising such inhibitors, and to uses of such inhibitors in the treatment and prophylaxis of disease.

BACKGROUND OF THE INVENTION

The AGC-kinases include the protein kinase C (PKC) and Rho-associated, coiled-coil containing protein kinase (ROCK) families. The PKC family of serine-threonine kinases transduce signals involving lipid second messengers. There are 9 genes that encode isozymes of PKC, several of which have splice variants. These isoforms are known as alpha, beta, gamma, delta, epsilon, zeta, eta, iota/lambda and theta (Nishizuka, Science 258, 607-614 (1992), Selbie et al., J Biol Chem 268, 24296-24302 (1993)). Based on sequence homology and biochemical properties, these PKC isozymes can be subdivided into three subgroups:

(a) the group of "conventional" PKCs comprising the alpha, beta, and gamma isozymes, which are all activated by calcium and diacylglycerol and can be stimulated by phorbol esters, (b) the group of "novel" PKCs comprising the delta, epsilon, theta and eta isozymes, which are all calcium-independent, but diacylglycerol- and phorbol ester-sensitive, and (c) the group of "atypical" PKCs, the zeta and iota (lambda in rodents) isozymes, which are insensitive to calcium, diacylglycerol and phorbol esters, but are activated by other lipids.

Members of the PKC family have been implicated in several disease states that could be treated by a PKC inhibitor. This application focuses on inhibitors directed against one isozyme, novel PKC epsilon, which has roles in pain, anxiety, addiction, inflammation, cardiac and cerebral ischemia, cancer, and diabetes. Embodiments of this invention for these and related indications are described below.

One embodiment of this invention is the development of a PKCs inhibitor for the treatment of pain. Pain is defined as an unpleasant sensory and emotional experience associated with actual or potential tissue damage, or described in terms of such damage. It is an extremely common complaint and accounts for over 40% of outpatient medical visits in the US each year, resulting in more than $100 billion in health care costs and lost productivity. Pain can be classified according to its pathophysiology, as inflammatory, widespread (generalized), or neuropathic. Inflammatory and partially widespread pain is caused by activation or sensitization of peripheral nociceptors, which are the peripheral sensory neurons that detect noxious stimuli. Neuropathic pain results from injury mainly to the peripheral nervous system. Acute pain is often inflammatory and accompanies trauma, dysfunction of viscera, inflammation, or infection. Chronic pain persists beyond the usual course of an acute episode, generally longer than 1 to 6 months, and may be inflammatory, widespread, or neuropathic, or a combination of these.

Pain medications are widely prescribed, accounting for about 12% of all outpatient prescriptions written in the US, and also constitute a huge over-the-counter market. The most widely used are non-steroidal anti-inflammatory drugs (NSAIDS), opioid analgesics, monoamine reuptake inhibitors, and anticonvulsants. Many have serious side effects that limit their use. NSAIDs can cause GI bleeding and renal insufficiency, and the COX-2 inhibitors in particular carry increased risk of cardiovascular events. Tricyclic antidepressants can cause autonomic dysfunction, and in high doses, arrhythmias and hypotension. Opioids are sedating, frequently cause nausea and constipation, and in high doses produce respiratory depression. They also induce tolerance and in a minority of patients can lead to addiction. Side effects associated with the anticonvulsants gabapentin and pregabalin include somnolence, fatigue, dizziness, ataxia and weight gain. Because of these limitations, and a lack of efficacy especially for chronic pain syndromes, there is still a major need for developing more effective pain mediations with an improved side effect profile. There are many ongoing clinical pain trials in the US. For example, a recent search of the ClinicalTrials.gov website even when restricted to the term "pain in rheumatoid arthritis" revealed nearly 200 proposed, ongoing, or recently completed trials. Therefore, as an example, performing a later-phase clinical trial on pain in rheumatoid arthritis patients is very feasible.

WO 00/01415 and U.S. Pat. No. 6,376,467 describe the use of inhibitors of PKC epsilon in the treatment of pain, in particular chronic hyperalgesia and/or inflammatory pain (reference is also made to WO 02/102232 and WO 03/089457). As examples of suitable inhibitors, both peptides as well as small molecules are mentioned. WO 97/15575 and WO 01/83449 describe modulators of PKC with specific binding activity with respect to PKC epsilon. Peptide inhibitors that provide isozyme-specific modulation of PKC (in particular of PKC gamma and PKC epsilon) are described in WO 03/089456 and WO 03/089457.

For the sequence of human PKC epsilon, reference is made inter alia made to Basta et al., Biochim Biophys Acta, 1132 (1992), 154-160, as well as to SWISS-PROT entry Q02156 and EMBL entry X65293.

WO 03/04612 describes the use of inhibitors of PKC theta as an immunosuppressive agent (e.g. during organ transplant) and for treatment of systemic lupus erythematosus. Reference is also made to Castrillo et al., J Exp Med, 194, 9 (2001), p 1231-1242, who describe that PKC epsilon plays a role as a mediator in signaling cascades in activated macrophages.

The art also describes that PKC isozymes are associated with the metabolic diseases of diabetes and obesity. The link between PKC epsilon and these disorders has been established in two model systems for diabetes and obesity, viz the sand rat Psammomys and the High Fat Fed Rat. Reference is inter alia made to Shafrir et al., Annals New York Academy of Sciences 892 223-241 (1999), Donelly and Qu, Clin. Exper. Pharmacol. Phsyiol. 25: 79-87 (1998) and Qu et al., Journal of Endocrinology 162: 207-214 (1999). The latter two references also suggest that another novel PKC isozyme, PKC theta, may be involved in diabetes and obesity.

Other PKC isozymes have also been linked to diabetes and obesity; reference is inter alia made to U.S. Pat. No. 6,376,467, U.S. Pat. No. 6,284,784, U.S. Pat. No. 6,080,784, U.S. Pat. No. 6,057,440, U.S. Pat. No. 5,962,504, WO 02/22709, WO 01/30331, WO 96/40894 and the further references cited therein. U.S. Pat. No. 6,057,440, U.S. Pat. No. 5,698,578 and U.S. Pat. No. 5,739,322 describe the use of bisindolylmaleimide compounds as inhibitors of PKC beta in the prevention and treatment of diabetes and diabetes-related complications. These aforementioned patent applications and patents also describe an assay that can be used to determine the specificity of a given inhibitor for one isoform of PKC compared with another (referred to in these patents as the "PKC Enzyme Assay"). German patent application DE 197 40 384 A1 describes that antisense oligonucleotide sequences specific for certain PKC isozymes, and in particular against the alpha, delta, epsilon and zeta isoforms, may be used in the prevention or treatment of complications associated with diabetes. WO 01/81633 describes the association on PKC zeta with diabetes. Similarly, WO 94/18328 describes that the "atypical" PKC isozyme iota is involved in diabetes.

The art also describes that PKC epsilon is important for several neuropsychiatric disorders besides pain. WO 00/01805 describes PKC-epsilon knockout mice. This animal model is used to demonstrate that PKC epsilon can be used as a target for drugs to reduce anxiety, modulate alcohol consumption and drug abuse, addiction, withdrawal syndrome, muscle spasms, convulsive seizures, epilepsy and to modulate the action of drugs that target the GABA-A receptor.

US 2003/0134774 describes the use of inhibitors of PKC epsilon and PKC theta in inhibiting the onset of a cardiac disorder (e.g., hypertensive heart disease, valvular heart disease, diabetic heart disease, ischemic heart disease, etc.) and the progression of heart failure.

For other potential uses of inhibitors of PKC and/or of specific isoforms of PKC, reference is for example made to US 2002/0164389, US 2003/0118529, US 2003/0176424, US 2003/0176423, US 2003/0166678, US 2003/0134774, US 2003/0166678, US 2003/0176424, US 2003/0199423, WO 03/82859, WO 02/103000 and WO 02/87417.

SUMMARY OF THE INVENTION

The compounds described herein act as inhibitors of AGC-kinases and in particular as inhibitors of the novel calcium-independent but diacylglycerol- and phorbol ester-sensitive PKC epsilon isoform. The compounds described herein also act as inhibitors of novel PKC theta. The compounds described herein act as inhibitors of other AGC-kinases and in particular of Rho-associated, coiled-coil containing protein kinase (ROCK).

In one embodiment, the invention provides a compound of Formula I or II or a stereoisomer, tautomer, racemate, metabolite, pro- or pre-drug, salt, hydrate, or solvate thereof;

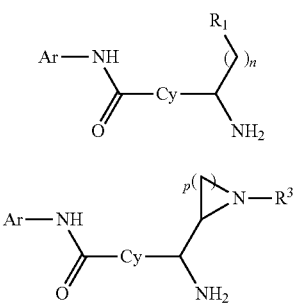

wherein

Ar is an aromatic 6-membered first ring containing carbon atoms and at least one nitrogen atom, said first ring being optionally fused to an unsaturated or aromatic 4-, 5-, 6-, or 7-membered second ring containing carbon atoms and optionally at least one nitrogen atom, said first or said second rings being independently substituted with one or more substituents independently selected from the group comprising hydrogen, halogen, alkyl, cycloalkyl, alkenyl, alkynyl, aralkyl, heteroarylalkyl, cycloalkylalkyl, acyl, aryl or heteroaryl wherein said substituents are optionally substituted by one or more further substituents selected from the group comprising halo, hydroxyl, oxo, nitro, amido, carboxy, amino, cyano, haloalkoxy, and haloalkyl;

Cy is a cycloalkylene or heterocycloalkylene third ring containing 3-12 carbon atoms, optionally one or two heteroatoms, and optionally one or two sites of unsaturation, provided that Cy is not aromatic, said third ring optionally fused to a cycloalkyl or heterocyclyl fourth ring containing carbon atoms and optionally at least one heteroatom atom, wherein said third ring is optionally substituted with one or more substituents selected from the group comprising halogen, alkenyl, alkyl, alkynyl, acylamino, alkoxy, arylamino, nitro, haloalkoxy, aryl or heteroaryl, wherein said substituents are optionally substituted by one or more further substituents selected from the group comprising halo, hydroxyl, oxo, nitro, amido, carboxy, amino, cyano, haloalkoxy, and haloalkyl;

n is an integer selected from 0, 1, 2, 3, and 4; and
$R^1$ is selected from the Formula:

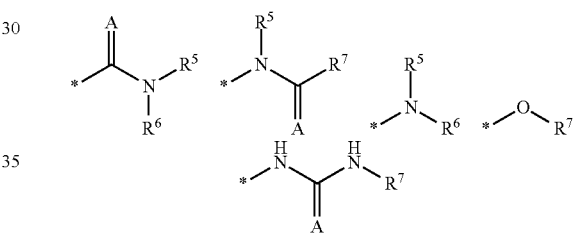

with the proviso that when n is 0, then $R^1$ is

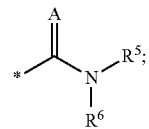

p is an integer selected from 2, 3, 4, 5, and 6;
$R^3$ is selected from the Formula:

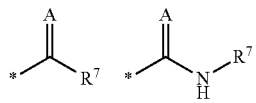

A is an oxygen or sulfur atom;
$R^5$, $R^6$ and $R^7$ are each independently selected from the group consisting of hydrogen, alkoxy, alkyl, alkylamino, alkylaminoalkyl, alkylcarbonyl, alkylcarbonylamino, amino, aralkyl, aryl, carbonylamino, cycloalkyl, formylamino, heteroaryl, heteroarylalkyl, heterocyclyl, or fused to the cycloalkyl, aryl, heterocyclyl or heteroaryl group may be one or more cycloalkyl, aryl, heterocyclyl or heteroaryl;

each group being optionally substituted by one or more substituent selected from halo, alkenylaminooxy, alkoxy, alkyl, alkylamino, alkylaminosulfonyl, alkylcarbonyl, alkylcarbonylamino, alkyloxyaminoalkenyl, alkyloxycarbonyl, alkylsulfonyl, alkylsulfonylamino, alkylthio, amino, aralkyl, aryl, arylalkenylaminooxy, arylamino, arylaminosulfonyl, arylcarbonyl, arylcarbonylamino, aryloxy, cyano, cycloalkyl, haloalkoxy, haloalkyl, haloaryl, heteroaryl, heteroarylalkenylaminooxy, heteroarylalkyl, heteroarylcarbonylamino, heterocyclyl, hydroxyalkyl, nitro, oxo, sulfonyl, or fused to the cycloalkyl, aryl, heterocyclyl substituent or heteroaryl may be one or more cycloalkyl, aryl, heterocyclyl or heteroaryl; and wherein each of said substituent being optionally substituted by one or more further substituent selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl.

In another embodiment, the invention provides a pharmaceutical and/or veterinary composition comprising a compound of the invention.

In another embodiment, the invention provides a compound of the invention for use in human or veterinary medicine.

In another embodiment, the invention provides the use of a compound of the invention, or a composition comprising such a compound, for inhibiting the activity of PKC epsilon and/or PKC theta, in vitro or in vivo.

In another embodiment, the present invention is directed to a method for treating a patient suffering from substance abuse and/or substance dependence, which method comprises administering an effective amount of a compound of the invention to said patient.

In another embodiment, the present invention is directed to a method for treating a patient suffering from depression or anxiety, which method comprises administering an effective amount of a compound of the invention to said patient.

In another embodiment, the invention provides the use of a compound of the invention in the preparation of a medicament for the prevention and/or treatment of at least one disease and/or disorder selected from the group comprising metabolic diseases (such as Type I and Type II diabetes, obesity, or metabolic syndrome), anxiety, addiction, withdrawal symptoms, muscle spasms, convulsive seizures, epilepsy, pain, cardiovascular disease, including heart disease, inflammatory diseases, and/or for regulating the immune system and/or an immune response and/or inflammatory response in a mammal.

In another embodiment, the invention provides the use of a compound of the invention in the preparation of a medicament for the prevention and/or treatment of type II diabetes, and/or for preventing, treating and/or alleviating complications and/or symptoms associated therewith.

In another embodiment, the invention provides the use of a compound of the invention in the preparation of a medicament for the prevention and/or treatment of obesity, and/or for preventing, treating and/or alleviating complications and/or symptoms associated therewith and/or alleviating complications and/or symptoms associated therewith.

In another embodiment, the invention provides the use of a compound of the invention in the preparation of a medicament for the prevention, treatment and/or management of pain, and/or for preventing, treating and/or alleviating complications and/or symptoms associated therewith.

In another embodiment, the invention provides the use of a compound of the invention in the preparation of a medicament for the prevention and/or treatment of inflammatory diseases (such as contact dermatitis, psoriasis, rheumatoid arthritis, inflammatory bowel disease, Crohn's disease, ulcerative colitis), kidney disease (such as renal dysfunction), cancer (such as cancer of the lung, intestine, nerve, skin, pancreas, liver, uterus, ovary, brain, thyroid gland, or leukemia or lymphoma melanoma), blood disease (such as sepsis, eosinophils or endotoxemia), atherosclerosis, allergy and autoimmune diseases or disorders, AIDS, diabetes (hyperglycemia), obesity and pancreas disease, multiple sclerosis and/or for preventing, treating and/or alleviating complications and/or symptoms associated therewith.

In another embodiment, the invention provides the use of a compound of the invention in the preparation of a medicament for the prevention and/or treatment of inflammatory diseases, such as contact dermatitis, psoriasis, rheumatoid arthritis, inflammatory bowel disease, Crohn's disease, ulcerative colitis, and/or for preventing, treating and/or alleviating complications and/or symptoms and/or inflammatory responses associated therewith.

In another embodiment, the invention provides the use of a compound of the invention in the preparation of a medicament for the prevention and/or treatment of sepsis, such as septic shock, and/or for preventing, treating and/or alleviating complications and/or symptoms associated therewith.

In another embodiment, the invention provides the use of a compound of the invention, or a composition comprising such a compound, for inhibiting the activity of at least one ROCK, for example ROCK1 and/or ROCK2 isoforms.

In another embodiment, the invention provides the use of a compound of the invention in the preparation of a medicament for the prevention and/or treatment of at least one disease and/or disorder selected from the group comprising eye diseases, erectile dysfunction, cardiovascular diseases, vascular diseases, proliferative diseases, inflammatory diseases, neurological diseases and disease of the central nervous system (CNS), bronchial asthma, osteoporosis, renal diseases, and AIDS.

In another embodiment, the invention provides the use of a compound of the invention in the preparation of a medicament for the prevention and/or treatment of eyes diseases including retinopathy, macular degeneration and glaucoma, and/or for preventing, treating and/or alleviating complications and/or symptoms associated therewith.

In another embodiment, the invention provides the use of a compound of the invention in the preparation of a medicament for the prevention and/or treatment of cardiovascular and vascular diseases, including but not limited to angina, coronary vasospasm, cerebral vasospasm, pulmonary vasoconstriction, restenosis, hypertension, (pulmonary) hypertension, arteriosclerosis, thrombosis (including deep thrombosis), platelet related diseases, acute stroke, congestive heart failure, cardiovascular ischemia, heart disease, and cardiac remodeling and/or for preventing, treating and/or alleviating complications and/or symptoms associated therewith and/or alleviating complications and/or symptoms associated therewith.

In another embodiment, the invention provides the use of a compound of the invention in the preparation of a medicament for the prevention, treatment and/or management of neurological and CNS disorders including but not limited to stroke, multiple sclerosis, brain or spinal cord injury, inflammatory and demyelinating diseases such as Alzheimer's disease, MS and neuropathic pain, and/or for preventing, treating and/or alleviating complications and/or symptoms associated therewith.

In another embodiment, the invention provides the use of a compound of the invention in the preparation of a medicament for the prevention and/or treatment of proliferative diseases such as cancer including but not limited to brain (e.g., gliomas), breast, colon, head and neck, kidney, lung, liver, melanoma, ovarian, pancreatic, prostate, sarcoma, or thyroid cancer, and/or for preventing, treating and/or alleviating complications and/or symptoms and/or inflammatory responses associated therewith.

In another embodiment, the invention provides the use of a compound of the invention in the preparation of a medicament for the prevention and/or treatment of erectile dysfunction, bronchial asthma, osteoporosis, renal diseases and AIDS, and/or for preventing, treating and/or alleviating complications and/or symptoms associated therewith.

In another embodiment, the invention provides the use of a compound of the invention, or a composition comprising such a compound, for inhibiting the activity of at least one kinase, in vitro or in vivo.

DETAILED DESCRIPTION OF THE INVENTION

Figure 1:
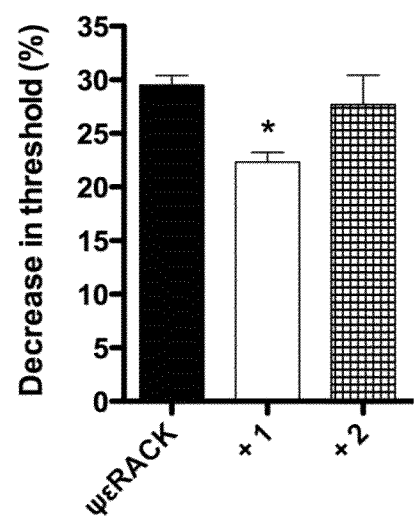
FIG. 1 shows the inhibition of PKCε-stimulated mechanical hyperalgesia in rats (Example 3, iii).

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

Undefined (racemic) asymmetric centers that may be present in the compounds of Formula I or II are interchangeably indicated by drawing a straight bond in order to visualize the undefined steric character of the bond, for example

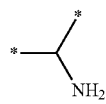

is used for the carbon bearing the amine of compounds of Formula I or II.

In an embodiment, the present invention provides a compound of Formula I or II

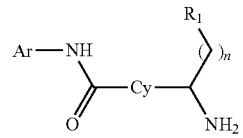

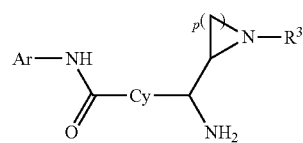

wherein

Ar is an aromatic 6-membered first ring containing carbon atoms and at least one nitrogen atom, said first ring being optionally fused to an unsaturated or aromatic 4-, 5-, 6-, or 7-membered second ring containing carbon atoms and optionally at least one nitrogen atom, said first or said second rings being independently substituted with one or more substituents independently selected from the group comprising hydrogen, halogen, alkyl, cycloalkyl, alkenyl, alkynyl, aralkyl, heteroarylalkyl, cycloalkylalkyl, acyl, aryl or heteroaryl wherein said substituents are optionally substituted by one or more further substituents selected from the group comprising halo, hydroxyl, oxo, nitro, amido, carboxy, amino, cyano, haloalkoxy, and haloalkyl;

Cy is a cycloalkyl or heterocyclkyl third ring containing 3-12 carbon atoms, optionally one or two heteroatoms, and optionally one or two sites of unsaturation, provided that Cy is not aromatic, said third ring optionally fused to a cycloalkyl or heterocyclyl fourth ring containing carbon atoms and optionally at least one heteroatom atom, wherein said third ring is optionally substituted with one or more substituents selected from the group comprising halogen, alkenyl, alkyl, alkynyl, acylamino, alkoxy, arylamino, nitro, haloalkoxy, aryl or heteroaryl, wherein said substituents are optionally substituted by one or more further substituents selected from the group comprising halo, hydroxyl, oxo, nitro, amido, carboxy, amino, cyano, haloalkoxy, and haloalkyl;

n is an integer selected from 0, 1, 2 or 3, preferably 0, 1 or 2;

p is an integer selected from 2, 3, 4 or 5, preferably 3 or 4, more preferably 3;

R$^1$ is selected from the Formula

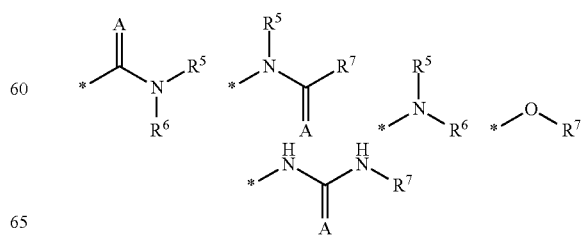

with the proviso that when n is 0, then $R^1$ is

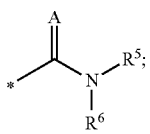

$R^3$ is selected from the Formula

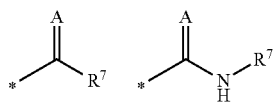

wherein
A is an oxygen or sulfur atom,
$R^5$, $R^6$ and $R^7$ are each independently selected from the group comprising:
(A) hydrogen,
(B) alkyl, alkenyl or alkynyl, optionally substituted with:
 (i) a homocyclic, heterocyclic, aryl or heteroaryl ring, to which may be a fused one or more homo or heterocyclic, aryl or heteroaryl rings, and which said ring or said one or more optional rings may be optionally substituted with one or more substituents independently selected from a first group comprising alkyl, hydroxyalkyl, haloalkyl, alkenyl, alkynyl, and homocyclic, heterocyclic, aryl or heteroaryl rings, wherein any substituents from this first group may be attached though an oxygen, sulfur or nitrogen atom or though one carbon atom, or independently selected from a second group comprising halo, oxo, nitro, amido, carboxy, hydroxyl, amino, cyano and haloalkoxy, or
 (ii) a substituent selected from the second group defined in part (i), or
 (iii) a substituent selected from the first group as defined in part (i) wherein said substituent is attached though an oxygen, sulfur or nitrogen atom or though one carbon atom, and wherein said a homocyclic, heterocyclic, aryl or heteroaryl rings are as defined in part (i),
(C) homocyclic and heterocyclic rings optionally substituted with
 (iv) a homocyclic, heterocyclic, aryl or heteroaryl ring as defined in part (i), or
 (v) a substituent selected from the second group as defined in part (i), or
 (vi) a substituent selected from the first group as defined in part (i) wherein said alkyl, hydroxyalkyl, haloalkyl, alkenyl, alkynyl, and homocyclic, heterocyclic, aryl or heteroaryl rings may, if present, be attached though an oxygen, sulfur or nitrogen atom or though one carbon atom, and wherein said homocyclic, heterocyclic, aryl or heteroaryl rings are as defined in part (i), and
 (vii) where the homocyclic or heterocyclic rings comprise 4 or more ring atoms, fused to the homocyclic and heterocyclic rings may be one or more homo or heterocyclic, aryl or heteroaryl rings, and said rings, if present, may be optionally substituted with one or more substituents independently selected from the first or a second groups as defined in part (i) wherein said substituents in said second group may, if present, be attached though an oxygen, sulfur or nitrogen atom or though one carbon atom, and
(D) an aryl or heteroaryl ring optionally substituted with
 (viii) a homocyclic, heterocyclic, aryl or heteroaryl ring as defined in part (i), or
 (ix) a substituent selected from the second group as defined in part (i), or
 (x) a substituent selected from the first group as defined in part (i) wherein said alkyl, hydroxyalkyl, haloalkyl, alkenyl, alkynyl, and homocyclic, heterocyclic, aryl or heteroaryl rings may, if present, be attached though an oxygen, sulfur or nitrogen atom or though one carbon atom, and wherein said homocyclic, heterocyclic, aryl or heteroaryl rings are as defined in part (i), and
 (xi) fused to the aryl or heteroaryl ring may be one or more homo or heterocyclic, aryl or heteroaryl rings, and said rings, if present, may be optionally substituted with one or more substituents independently selected from the first or a second groups as defined in part (i) wherein said substituents in said second group may, if present, be attached though an oxygen, sulfur or nitrogen atom or though one carbon atom, or a stereoisomer, tautomer, racemate, metabolite, pro- or pre-drug, salt, hydrate, or solvate thereof.

When describing the compounds of the invention, the terms used are to be construed in accordance with the following definitions, unless a context dictates otherwise.

The term "alkyl" by itself or as part of another substituent refers to a hydrocarbyl radical of Formula $C_nH_{2n+1}$ wherein n is a number greater than or equal to 1. Generally, alkyl groups of this invention comprise from 1 to 20 carbon atoms, more preferably from 1 to 10 carbon atoms, still more preferably 1 to 8 carbon atoms, in particular 1 to 6 carbon atoms, preferably 1 to 4 carbon atoms. Alkyl groups may be linear or branched and may be substituted as indicated herein. When a subscript is used herein following a carbon atom, the subscript refers to the number of carbon atoms that the named group may contain. Thus, for example, $C_{1-4}$alkyl means an alkyl of one to four carbon atoms. Examples of alkyl groups are methyl, ethyl, n-propyl, i-propyl, butyl and its isomers (e.g. n-butyl, i-butyl and t-butyl), pentyl and its isomers, hexyl and its isomers, heptyl and its isomers, octyl and its isomers, nonyl and its isomers, decyl and its isomers. $C_1$-$C_6$ alkyl includes all linear, branched or cyclic alkyl groups with between 1 and 6 carbon atoms, and thus includes methyl, ethyl, n-propyl, i-propyl, butyl and its isomers (e.g. n-butyl, i-butyl and t-butyl), pentyl and its isomers, hexyl and its isomers, cyclopentyl, 2-, 3- or 4-methylcyclopentyl, cyclopentylmethylene, and cyclohexyl.

The term "optionally substituted alkyl" refers to an alkyl group optionally substituted with one or more substituents (for example 1 to 4 substituents, for example 1, 2, 3 or 4 substituents) at any available point of attachment. Non-limiting examples of such substituents include halogen, hydroxy, carbonyl, nitro, amino, oximes, imines, azido, hydrazino, cyano, alkyl, aryl, heteroaryl, cycloalkyl, acyl, alkylamino, alkoxy, thiol, alkylthio, carboxylic acid, acylamino, alkyl esters, carbamates, thioamides, urea, sulphonamides and the like. When the term "alkyl" is used as a suffix following another term, as in "hydroxyalkyl," this is intended to refer to an alkyl group, as defined above, being substituted with one or two (preferably one) substituent(s) selected from the other, specifically-named group, also as defined herein.

The term "hydroxyalkyl" refers to a —$R^a$—OH group wherein $R^a$ is alkylene as defined herein. For example, "hydroxyalkyl" includes 2-hydroxyethyl, 1-(hydroxymethyl)-2-methylpropyl, 3,4-dihydroxybutyl, and so forth. "Alkoxyalkyl" refers to an alkyl group substituted with one to two of OR', wherein R' is alkoxy as defined below. For example, "aralkyl" or "(aryl)alkyl" refers to a substituted alkyl group as defined above wherein at least one of the alkyl substituents is an aryl as defined below, such as benzyl. For example, "heteroarylalkyl" refers to a substituted alkyl group as defined above, wherein at least one of the alkyl substituents is a heteroaryl as defined below, such as pyridinyl.

The term "cycloalkyl" as used herein is a cyclic alkyl group, that is to say, a monovalent, saturated, or unsaturated hydrocarbyl group having 1, 2 or 3 cyclic structure. Cycloalkyl includes all saturated or partially saturated (containing 1 or 2 double bonds) hydrocarbon groups containing 1 to 3 rings, including monocyclic, bicyclic or polycyclic alkyl groups. Cycloalkyl groups may comprise 3 or more carbon atoms in the ring and generally, according to this invention comprise from 3 to 10, more preferably from 3 to 8 carbon atoms stilt more preferably from 3 to 6 carbon atoms. The further rings of multi-ring cycloalkyls may be either fused, bridged and/or joined through one or more spiro atoms. Cycloalkyl groups may also be considered to be a subset of homocyclic rings discussed hereinafter. Examples of cycloalkyl groups are cyclopropyl, cyclobutyl, cyclopentyl, cyclohexyl, cycloheptyl, cyclooctyl, cyclononyl and cyclodecyl with cyclopropyl being particularly preferred. An "optionally substituted cycloalkyl" refers to a cycloalkyl having optionally one or more substituents (for example 1 to 3 substituents, for example 1, 2, 3 or 4 substituents), selected from those defined above for substituted alkyl. When the suffix "ene" is used in conjunction with a cyclic group, this is intended to mean the cyclic group as defined herein having two single bonds as points of attachment to other groups.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene. Similarly, where alkenyl groups as defined above and alkynyl groups as defined above, respectively, are divalent radicals having single bonds for attachment to two other groups, they are termed "alkenylene" and "alkynylene" respectively.

Generally, alkylene groups of this invention preferably comprise the same number of carbon atoms as their alkyl counterparts. "Cycloalkylene" herein refers to a saturated homocyclic hydrocarbyl biradical of Formula $C_nH_{2n+2}$. Cycloalkylene groups of this invention preferably comprise the same number of carbon atoms as their cycloalkyl radical counterparts. Where an alkylene or cycloalkylene biradical is present, connectivity to the molecular structure of which it forms part may be through a common carbon atom or different carbon atom, preferably a common carbon atom. To illustrate this applying the asterisk nomenclature of this invention, a C3 alkylene group may be for example *—$CH_2CH_2$ $CH_2$—*, *—CH(—$CH_2CH_3$)—* or *—$CH_2CH$ (—$CH_3$)—*. Likewise a $C_3$ cycloalkylene group may be

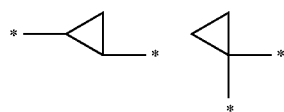

Where a cycloalkylene group is present, this is preferably a $C_3$-$C_6$ cycloalkylene group, more preferably a $C_3$ cycloalkylene (i.e. cyclopropylene group) wherein its connectivity to the structure of which it forms part is through a common carbon atom. Cycloalkylene and alkylene biradicals in compounds of the invention may be, but preferably are not, substituted, and may contain one or two sites of unsaturation, provided that the ring is not aromatic.

The term "alkenyl" as used herein refers to an unsaturated hydrocarbyl group, which may be linear, branched or cyclic, comprising one or more carbon-carbon double bonds. Alkenyl groups thus comprise two or more carbon atoms, preferably between 2 and 20 carbon atoms, more preferably between 2 and 10 carbon atoms, still more preferably between 2 and 8 carbon atoms, for example, between 2 and 6 carbon atoms. Examples of alkenyl groups are ethenyl, 2-propenyl, 2-butenyl, 3-butenyl, 2-pentenyl and its isomers, 2-hexenyl and its isomers, 2-heptenyl and its isomers, 2-octenyl and its isomers, 2,4-pentadienyl and the like. An optionally substituted alkenyl refers to an alkenyl having optionally one or more substituents (for example 1, 2 or 3 substituents, or 1 to 2 substituents), selected from those defined above for substituted alkyl. Similarly to cycloalkyl groups, cycloalkenyl groups may be considered to be a subset of homocyclic rings discussed hereinafter.

The term "alkynyl" as used herein, similarly to alkenyl, refers to a class of monovalent unsaturated hydrocarbyl groups, wherein the unsaturation arises from the presence of one or more carbon-carbon triple bonds. Alkynyl groups typically, and preferably, have the same number of carbon atoms as described above in relation to alkenyl groups. Examples alkynyl groups are ethynyl, 2-propynyl, 2-butynyl, 3-butynyl, 2-pentynyl and its isomers, 2-hexynyl and its isomers, 2-heptynyl and its isomers, 2-octynyl and its isomers and the like. An optionally substituted alkynyl refers to an alkynyl having optionally one or more substituents (for example 1 to 4 substituents, or 1 to 2 substituents), selected from those defined above for substituted alkyl. Similarly to cycloalkyl groups, cycloalkynyl groups may be considered to be a subset of homocyclic rings discussed hereinafter.

The term "homocyclic ring" as used herein is a ring wherein the ring atoms comprise only carbon atoms. Examples of homocyclic rings thus include cycloalkyl, cycloalkenyl and cycloalkynyl, with cycloalkyl and cycloalkenyl being preferred. Where a ring carbon atom is replaced with a heteroatom, preferably nitrogen, oxygen of sulfur, the heteroatom-containing ring resultant from such a replacement is referred to herein as a heterocyclic ring. More than one carbon atom in a ring may be replaced so forming heterocyclic ring having a plurality of heteroatoms.

The terms "heterocyclyl" or "heterocyclo" as used herein by itself or as part of another group refer to non-aromatic, fully saturated or partially unsaturated cyclic groups (for example, 3 to 13 member monocyclic, 7 to 17 member bicyclic, or 10 to 20 member tricyclic ring systems, or containing a total of 3 to 10 ring atoms) which have at least one heteroatom in at least one carbon atom-containing ring, and optionally one or two sites of unsaturation provided that it is not-aromatic. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system, where valence allows. The rings of multi-ring heterocycles may be fused, bridged and/or joined through one or more spiro atoms. An optionally substituted heterocyclic refers to a heterocyclic having optionally one or more substituents (for example 1 to 4 substituents, or for example 1, 2, 3 or 4), selected from those defined above for substituted aryl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, indolinyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quiinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, triazinyl, cinnolinyl, phthalazinyl, oxetanyl, thietanyl, 3-dioxolanyl, 1,4-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl.

"heterocycloalkylene" herein refers to a biradical heterocyclyl group, where heterocyclyl is as defined above. The heterocycloalkylene group may be attached at any heteroatom or carbon atom of the ring or ring system, where valence allows.

The term "aryl" as used herein refers to a polyunsaturated, aromatic hydrocarbyl group having a single ring (i.e. phenyl) or multiple aromatic rings fused together (e.g. naphthalene or anthracene) or linked covalently, typically containing 5 to 8 atoms, wherein at least one ring is aromatic. The aromatic ring may optionally include one to three additional rings (either cycloalkyl, heterocyclyl or heteroaryl) fused thereto. Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7- or 8-azulenyl, 1- or 2-naphthyl, 1-, 2- or 3-indenyl, 1-, 2- or 9-anthryl, 1-, 2-, 3-, 4- or 5-acenaphtylenyl, 3-, 4- or 5-acenaphtenyl, 1-, 2-, 3-, 4- or 10-phenanthryl, 1- or 2-pentalenyl, 1-, 2-, 3- or 4-fluorenyl, 4- or 5-indanyl, 5-, 6-, 7- or 8-tetrahydronaphthyl, 1,2,3,4-tetrahydronaphthyl, 1-4-dihydronaphthyl, dibenzo[a,d]cylcoheptenyl, 1-, 2-, 3-, 4- or 5-pyrenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment. Non-limiting examples of such substituents are selected from halogen, hydroxy, oxo, nitro, amino, hydrazine, aminocarbonyl, azido cyano, alkyl, cycloalkyl, alkenyl, alkynyl, cycloalkylalkyl, alkylamino, alkoxy, —$SO_2$—$NH_2$, aryl, heteroaryl, aralkyl, haloalkyl, haloalkoxy, alkyloxycarbonyl, alkylaminocarbonyl, heteroarylalkyl, alkylsulfonamide, heterocyclyl, alkylcarbonylaminoalkyl, aryloxy, alkylcarbonyl, acyl, arylcarbonyl, aminocarbonyl, alkylsulfoxide, —$SO_2R^{115}$, alkylthio, carboxy, and the like, wherein $R^{115}$ is alkyl or cycloalkyl.

The term "arylene" as used herein is intended to include divalent carbocyclic aromatic ring systems such as phenylene, biphenylene, naphthylene, anthracenylene, phenanthrenylene, fluorenylene, indenylene, pentalenylene, azulenylene and the like. Arylene is also intended to include the partially hydrogenated derivatives of the carbocyclic systems enumerated above. Non-limiting examples of such partially hydrogenated derivatives are 1,2,3,4-tetrahydronaphthylene, 1,4-dihydronaphthylene and the like.

Where a carbon atom in an aryl group is replaced with a heteroatom, the resultant ring is referred to herein as a heteroaryl ring.

The term "heteroaryl" as used herein by itself or as part of another group refers but is not limited to 5 to 12 carbon-atom aromatic rings or ring systems containing 1 to 3 rings which are fused together or linked covalently, typically containing 5 to 8 atoms, at least one of which is aromatic in which one or more carbon atoms in one or more of these rings can be replaced by oxygen, nitrogen or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring Non-limiting examples of heteroaryl can be 2- or 3-furyl, 2- or 3-thienyl, 1-, 2- or 3-pyrrolyl, 1-, 2-, 4- or 5-imidazolyl, 1-, 3-, 4- or 5-pyrazolyl, 3-, 4- or 5-isoxazolyl, 2-, 4- or 5-oxazolyl, 3-, 4- or 5-isothiazolyl, 2-, 4- or 5-thiazolyl, 1,2,3-triazol-1-, -2-, -4- or -5-yl, 1,2,4-triazol-1-, -3-, -4- or -5-yl, 1,2,3-oxadiazol-4- or -5-yl, 1,2,4-oxadiazol-3- or -5-yl, 1,2,5-oxadiazolyl, 1,3,4-oxadiazolyl, 1,2,3-thiadiazol-4- or -5-yl, 1,2,4-thiadiazol-3- or -5-yl, 1,2,5-thiadiazol-3- or -4-yl, 1,3,4-thiadiazolyl, 1- or 5-tetrazolyl, 2-, 3- or 4-pyridyl, 3- or 4-pyridazinyl, 2-, 4-, 5- or 6-pyrimidinyl, 2-, 3-, 4-, 5-6-2H-thiopyranyl, 2-, 3- or 4-4H-thiopyranyl, 2-, 3-, 4-, 5-, 6- or 7-benzofuryl, 1-, 3-, 4- or 5-isobenzofuryl, 2-, 3-, 4-, 5-, 6- or 7-benzothienyl, 1-, 3-, 4- or 5-isobenzothienyl, 1-, 2-, 3-, 4-, 5-, 6- or 7-indolyl, 2- or 3-pyrazinyl, 1,4-oxazin-2- or -3-yl, 1,4-dioxin-2- or -3-yl, 1,4-thiazin-2- or -3-yl, 1,2,3-triazinyl, 1,2,4-triazinyl, 1,3,5-triazin-2-, -4- or -6-yl, thieno[2,3-b]furan-2-, -3-, -4-, or -5-yl, 1-, 2-, 4- or 5-benzimidazolyl, 1-, 3-, 4-, 5-, 6- or 7-benzopyrazolyl, 3-, 4-, 5-, 6- or 7-benzisoxazolyl, 2-, 4-, 5-, 6- or 7-benzoxazolyl, 3-, 4-, 5-, 6- or 7-benzisothiazolyl, 2-, 4-, 5-, 6- or 7-benzothiazolyl, 1-, 2-thianthrenyl, 3-, 4- or 5-isobenzofuranyl, 1-, 2-, 3-, 4- or 9-xanthenyl, 1-, 2-, 3- or 4-phenoxathinyl, 2-, 3-pyrazinyl, 1-, 2-, 3-, 4-, 5-, 6-, 7- or 8-indolizinyl, 2-, 3-, 4- or 5-isoindolyl, 1-, 2-, 3-, 4-, 5-, 6- or 7-indazolyl, 2-, 6-, 7- or 8-purinyl, 4-, 5- or 6-phthalazinyl, 2-, 3- or 4-naphthyridinyl, 2-, 5- or 6-quinoxalinyl, 2-, 4-, 5-, 6-, 7- or 8-quinazolinyl, 1-, 2-, 3- or 4-quinolizinyl, 2-, 3-, 4-, 5-, 6-, 7-, or 8-quinolinyl(quinolyl), 2-, 4-, 5-, 6-, 7- or 8-quinazolyl, 1-, 3-, 4-, 5-, 6-, 7- or 8-isoquinolinyl(isoquinolyl), 3-, 4-, 5-, 6-, 7- or 8-cinnolinyl, 2-, 4-, 6- or 7-pteridinyl, 1-, 2-, 3-, 4- or 9-carbazolyl, 1-, 2-, 3-, 4-, 5-, 6-, 7-, 8- or 9-carbolinyl, 1-, 2-, 3-, 4-, 5-, 6-, 7-, 8-, 9- or 10-phenanthridinyl, 1-, 2-, 3- or 4-acridinyl, 1-, 2-, 3-, 4-, 5-, 6-, 7-, 8- or 9-perimidinyl, 2-, 3-, A-, 5-, 6-, 7-, 8-, 9- or 10-(1,7)phenanthrolinyl, 1- or 2-phenazinyl, 1-, 2-, 3-, 4-, or 10-phenothiazinyl, 3- or 4-furazanyl, 1-, 2-, 3-, A-, or 10-phenoxazinyl, or additionally substituted derivatives thereof.

An "optionally substituted heteroaryl" refers to a heteroaryl having optionally one or more substituents (for example 1 to 4 substituents, for example 1, 2, 3 or 4), selected from those defined above for substituted aryl.

The term "oxo" as used herein refers to the group =O.

The term "aryloxy" as used herein denotes a group —O-aryl, wherein aryl is as defined above.

The term "aroyl" as used herein denotes a group —C(O)-aryl, wherein aryl is as defined above.

The term "cycloalkylalkyl" by itself or as part of another substituent refers to a group having one of the aforementioned cycloalkyl groups attached to one of the aforementioned alkyl chains. Examples of such cycloalkylalkyl radicals include cyclopropylmethyl, cyclobutylmethyl, cyclopentylmethyl, cyclohexylmethyl, 1-cyclopentylethyl, 1-cyclohexylethyl, 2-cyclopentylethyl, 2-cyclohexylethyl, cyclobutylpropyl, cyclopentylpropyl, 3-cyclopentylbutyl, cyclohexylbutyl and the like.

The term "heterocyclylalkyl" by itself or as part of another substituents refers to a group having one of the aforementioned heterocyclyl group attached to one of the aforementioned alkyl group, i.e., to a group —$R^b$—$R^c$ wherein $R^b$ is alkylene or alkylene substituted by alkyl group and $R^c$ is a heterocyclyl group.

The term "acyl" by itself or as part of another substituent refers to an alkanoyl group having 2 to 6 carbon atoms or a phenylalkanoyl group whose alkanoyl moiety has 1 to 4 carbon atoms, i.e. a carbonyl group linked to a radical such as, but not limited to, alkyl, aryl, more particularly, the group —$COR^{10}$, wherein $R^{10}$ can be selected from alkyl, aryl, substituted alkyl, or substituted aryl, as defined herein. The term acyl therefore encompasses the group alkylcarbonyl (—$COR^{10}$), wherein $R^{10}$ is alkyl. Preferably, acyl is $C_2$-$C_{11}$acyl or $C_2$-$C_7$acyl. Where the oxygen atom is an acyl group is substituted with sulfur, the resultant radical is referred to as thioacyl. Said acyl can be exemplified by acetyl, propionyl, butyryl, valeryl and pivaloyl, benzoyl, phenylacetyl, phenylpropionyl and phenylbutyryl.

The term "amino" refers to the group —$NH_2$.

The term "alkylamino" by itself or as part of another substituent refers to a group consisting of an amino groups attached to one or two independently selected and optionally substituted alkyl groups, cycloalkyl groups, aralkyl or cycloalkylalkyl groups i.e., alkyl amino refers to —$N(R^8)(R^9)$ wherein $R^8$ and $R^9$ are each independently selected from hydrogen, cycloalkyl, arylalkyl, cycloalkylalky or alkyl, provided that only one is hydrogen. Non-limiting examples of alkylamino groups include methylamino ($NHCH_3$), ethylamino ($NHCH_2CH_3$), n-propylamino, isopropylamino, n-butylamino, isobutylamino, sec-butylamino, tert-butylamino, n-hexylamino, and the like.

The term "arylamino" by itself or as part of another substituent refers to a group consisting of an amino groups attached to one or two independently selected and optionally substituted aryl groups i.e., arylamino refers to —$N(R^8)(R^9)$ wherein $R^8$ and $R^9$ are each independently hydrogen or aryl, provided that only one is hydrogen.

The term "aminoalkyl" refers to the group —$R^b$—$NR^dR^e$ wherein $R^b$ is alkylene or substituted alkylene, $R^d$ is hydrogen or alkyl or substituted alkyl as defined herein, and $R^e$ is hydrogen or alkyl as defined herein.

The term "aminocarbonyl" refers to the group —(C=O)—$NH_2$.

The term "alkylaminocarbonyl" refers to a group —(C=O)—$NR^dR^e$ wherein $R^d$ is hydrogen or alkyl or substituted alkyl as defined herein, and $R^e$ is alkyl or substituted alkyl as defined herein.

The term "amido" refers to the group —(C=O)—$NR^dR^e$ wherein each of $R^d$ and $R^e$ are independently selected form the group selected form hydrogen, alkyl, substituted alkyl, aryl or substituted aryl as defined herein.

The term "alkylaminocarbonylamino" refers to a group —NH(C=O)—$NR^dR^e$ or —NR'(C=O)—$NR^dR^e$ wherein $R^d$ is hydrogen or alkyl or substituted alkyl as defined herein, and $R^e$ is alkyl or substituted alkyl as defined herein, wherein R' is alkyl or substituted alkyl.

The term "carboxy" or "carboxyl" refers to the group —$CO_2H$ Thus, a carboxyalkyl is an alkyl group as defined above having at least one substituent that is —$CO_2H$.

The term "alkoxycarbonyl" refers to a carboxy group linked to an alkyl radical i.e. to form —C(=O)$OR^{10}$, wherein $R^{10}$ is as defined above for acyl.

The term "alkylcarbonyloxy" refers to a —O—C(=O)$R^{11}$ wherein $R^{11}$ is as defined above for acyl.

The term "alkylcarbonylamino" refers to an group of Formula —NH(C=O)R or —NR'(C=O)R, wherein R and R' are each independently alkyl or substituted alkyl.

The term "alkylcarbonylaminoalkyl" refers to a group —$R^b$—$NR^d$—C(=O)—$R^e$ wherein $R^b$ is alkylene or substituted alkylene, $R^d$ is hydrogen or alkyl as defined herein, and $R^e$ is alkyl as defined herein.

The term "alkoxy" by itself or as part of another substituent refers to a group consisting of an oxygen atom attached to one optionally substituted straight or branched alkyl group, cycloalkyl group, aralkyl or cycloalkylalkyl group. Non-limiting examples of suitable alkoxy group include methoxy, ethoxy, n-propoxy, isopropoxy, n-butoxy, iso-butoxy, sec-butoxy, tert-butoxy, hexanoxy and the like.

The term "alkylthio" by itself or as part of another substituent refers to a group consisting of a sulfur atom attached to one optionally substituted alkyl group, cycloalkyl group, aralkyl or cycloalkylalkyl group. Non-limiting examples of alkylthio groups include methylthio ($SCH_3$), ethylthio ($SCH_2CH_3$), n-propylthio, isopropylthio, n-butylthio, isobutylthio, sec-butylthio, tert-butylthio, n-hexylthio, and the like.

The term "acylamino" by itself or as part of another substituent refers to a group consisting of an amino group attached to one or two independently selected acyl groups as described before. In case the two acyl groups of a dicarboxylic acid are attached to the amino group these represent imides such as phtalimides, maleimides and the like, and are encompassed in the meaning of the term acylamino.

The term "halo" or "halogen" as a group or part of a group is generic for fluoro, chloro, bromo or iodo.

The term "haloalkyl" alone or in combination, refers to an alkyl radical having the meaning as defined above wherein one or more hydrogens are replaced with a halogen as defined above. Non-limiting examples of such haloalkyl radicals include chloromethyl, 1-bromoethyl, fluoromethyl, difluoromethyl, trifluoromethyl, 1,1,1-trifluoroethyl and the like.

The term "haloalkoxy" alone or in combination refers to a group of Formula —O-alkyl wherein the alkyl group is substituted by 1, 2 or 3 halogen atoms. For example, "haloalkoxy" includes —$OCF_3$ and —$OCHF_2$. The term "sulfonamide" alone or in combination refers to a group of Formula —$SO_2$—NRR wherein each R independently is hydrogen or alkyl as defined herein.

The term "alkylsulfonylamino" alone or in combination refers to a group of Formula —$NR^d$—$SO_2$—R wherein $R^d$ is hydrogen or alkyl as defined herein, and R independently is alkyl as defined herein.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent. Where groups may be optionally substituted, such groups may be substituted once or more, and preferably once, twice or thrice. Substituents may be selected from, for example, the group comprising halo, hydroxy, alkoxy, oxo, nitro, amido, carboxy, amino, cyano, haloalkoxy, and haloalkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

Whenever used in the present invention the term "compounds of the invention" or a similar term is meant to include the compounds of general Formula I or II and any subgroup thereof. This term also refers to the compounds as depicted in Tables 1, 2 and 3 and their derivatives, N-oxides, salts, solvates, hydrates, stereoisomers forms, racemic mixtures, tautomeric forms, optical isomers, analogues, pro-drugs, esters and metabolites, as well as their quaterized nitrogen analogues. The N-oxide forms of said compounds are meant to comprise compounds wherein one or several nitrogen atoms are oxidized to the so-called N-oxide.

As used in the specification and the appended claims, the singular forms "a", "an," and "the" include plural referents unless the context clearly dictates otherwise. By way of example, "a compound" means one compound or more than one compound.

The terms described above and others used in the specification are well understood to those in the art.

Specific embodiments of the compounds of this invention are now set forth.

In one embodiment, the present invention provides the N-hydroxyl compound of the formula:

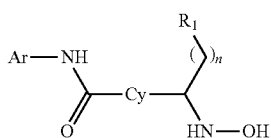

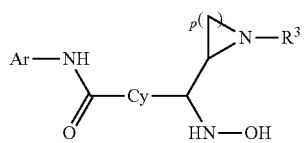

where Ar, Cy, n, and $R^1$ are as described above.

Ar is, preferably, a 4-pyridyl ring which, may be optionally substituted, or comprises a 4-pyridyl ring as part of a bicyclic structure wherein such bicyclic structure is attached to the nitrogen atom of the amide moiety shown in Formula I or II through the (1) carbon atom in the 4-pyridyl ring.

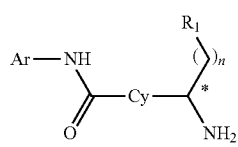

I

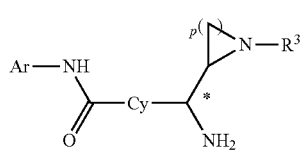

II

Preferred structures for Ar are of the Formula:

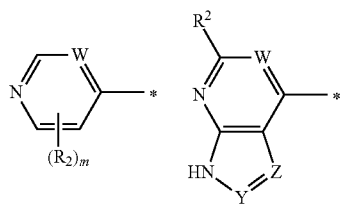

wherein m is an integer selected from 0, 1, 2 or 3, preferably 0, W is $C(R^2)$ or N, preferably $C(R^2)$, more preferably CH, Y and Z are independently selected from the group comprising N and $CR^2$, and $R^2$ is selected from hydrogen, halogen, or a group selected from alkyl, cycloalkyl, alkenyl, alkynyl, aryl or heteroaryl wherein each of said group is optionally substituted by one or more further substituents (for example 1, 2, or 3 substituents) selected from the group comprising halo, hydroxyl, amido, carboxy, amino, cyano, haloalkoxy, and haloalkyl.

In these preferred structures for Ar, the following features are preferred m is either 0 or 1, preferably 0, and W is N or $C(R^2)$, particularly wherein the $R^2$ present in W is hydrogen. In a particular embodiment, in these structures for Ar, the following features are preferred wherein Y is CH and Z is CH or wherein Y is CH and Z is N, or wherein Y is N and Z is CH.

It will be clear to the skilled person that Cy may be in the form of different stereoisomers (i.e. as cis- and trans-isomers. Both are included within the scope of the invention, with the trans-isomer being particularly preferred.

Cy is preferably of the Formula

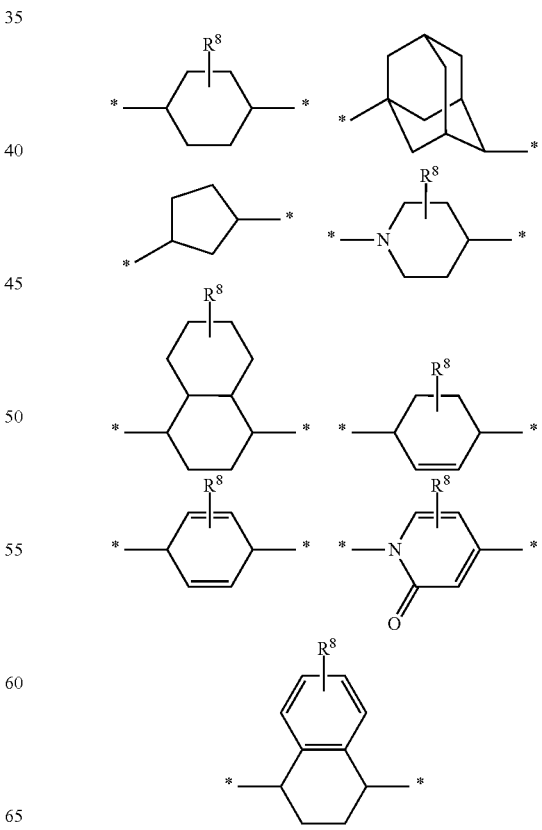

wherein $R^8$ is selected from the group comprising hydrogen and halogen, alkenyl, alkyl, alkynyl, acylamino, alkoxy, arylamino, nitro, haloalkoxy, aryl or heteroaryl, each group being optionally substituted by one or more substituents, and $R^9$ is selected from the group comprising hydrogen, halogen and alkyl.

Especially preferably, Cy is either of

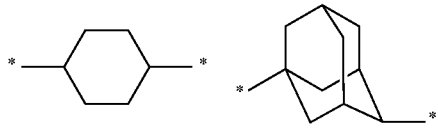

Preferably, where A is present in $R^1$, A is oxygen or sulfur. In some embodiments, A is preferably sulfur. In other embodiments, A is preferably oxygen. Generally, in the compounds of Formula I or II, in particular those in which n is 1, $R^1$ is preferably selected from the Formula

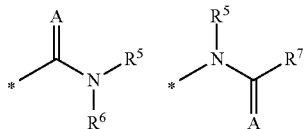

Generally, in the compounds of Formula I, in particular those in which n is 0, $R^1$ is preferably

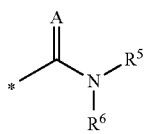

Particularly preferably, where $R^1$ is attached though one carbon atom, said one carbon atom is a methylene or cycloalkylene biradical, which is preferably unsubstituted. Where $R^1$ is attached though one carbon atom, and said one carbon atom is a cycloalkylene radical, this is preferably cyclopropylene.

In one embodiment of the invention $R^1$ is of the Formula
*—N(H)—C(=O)—$C^1$—$Ar^3$
wherein $C^1$ is a methylene or cycloalkylene biradical, and $Ar^3$ is an aromatic 5- or 6-membered ring containing carbon atoms and optionally one or two heteroatoms optionally substituted with one or more substituents (for example 1, 2, 3 or 4) selected from the group comprising halogen, alkenyl, alkyl, alkynyl, acylamino, alkoxy, arylamino, nitro and haloalkoxy.

In some embodiments, the invention is directed to compounds represented by Formula Ia, Ib or Ic:

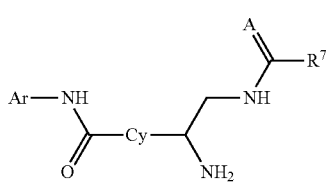

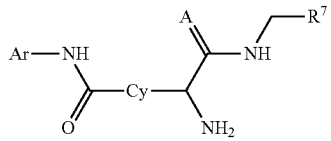

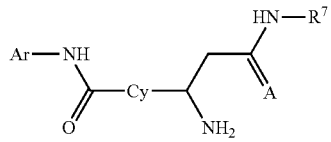

wherein
Ar is an aromatic 6-membered first ring containing carbon atoms and at least one nitrogen atom, said first ring being optionally fused to an unsaturated or aromatic 4-, 5-, 6-, or 7-membered second ring containing carbon atoms and optionally at least one nitrogen atom, said first or said second rings being independently substituted with one or more substituents independently selected from the group comprising hydrogen, halogen, alkyl, cycloalkyl, alkenyl, alkynyl, aralkyl, heteroarylalkyl, cycloalkylalkyl, acyl, aryl or heteroaryl wherein said substituents are optionally substituted by one or more further substituents selected from the group comprising halo, hydroxyl, oxo, nitro, amido, carboxy, amino, cyano, haloalkoxy, and haloalkyl;
Cy is a cycloalkylene or heterocycloalkylene third ring containing 3-12 carbon atoms, optionally one or two heteroatoms, and optionally one or two sites of unsaturation, provided that Cy is not aromatic, said third ring optionally fused to a cycloalkyl or heterocyclyl fourth ring containing carbon atoms and optionally at least one heteroatom atom, wherein said third ring is optionally substituted with one or more substituents selected from the group comprising halogen, alkenyl, alkyl, alkynyl, acylamino, alkoxy, arylamino, nitro, haloalkoxy, aryl or heteroaryl, wherein said substituents are optionally substituted by one or more further substituents selected from the group comprising halo, hydroxyl, oxo, nitro, amido, carboxy, amino, cyano, haloalkoxy, and haloalkyl;
A is an oxygen or sulfur atom; and
$R^7$ is selected from the group consisting of hydrogen, alkoxy, alkyl, alkylamino, alkylaminoalkyl, alkylcarbonyl, alkylcarbonylamino, amino, aralkyl, aryl, carbonylamino, cycloalkyl, formylamino, heteroaryl, heteroarylalkyl, heterocyclyl, or fused to the cycloalkyl, aryl, heterocyclyl or heteroaryl group may be one or more cycloalkyl, aryl, heterocyclyl or heteroaryl;
each group being optionally substituted by one or more substituent selected from halo, alkenylaminooxy, alkoxy, alkyl, alkylamino, alkylaminosulfonyl, alkylcarbonyl, alkylcarbonylamino, alkyloxyaminoalkenyl, alkyloxycarbonyl, alkylsulfonyl, alkylsulfonylamino, alkylthio, amino, aralkyl, aryl, arylalkenylaminooxy, arylamino, arylaminosulfonyl, arylcarbonyl, arylcarbonylamino, aryloxy, cyano, cycloalkyl, haloalkoxy, haloalkyl, haloaryl, heteroaryl, heteroarylalkenylaminooxy, heteroarylalkyl, heteroarylcarbonylamino, heterocyclyl, hydroxyalkyl, nitro, oxo, sulfonyl, or fused to the cycloalkyl, aryl, heterocyclyl substituent or heteroaryl may be one or more cycloalkyl, aryl, heterocyclyl or heteroaryl; and wherein
each of said substituent being optionally substituted by one or more further substituent selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl;

or a stereoisomer, tautomer, racemate, metabolite, pro- or pre-drug, salt, hydrate, or solvate thereof.

In some embodiments, Ar is selected from the group consisting of 1H-pyrrolo[2,3-b]pyridin-4-yl and pyridin-4-yl.

In some embodiments, A is an oxygen atom. In some embodiments, A is a sulfur atom.

Preferably, Cy is either of:

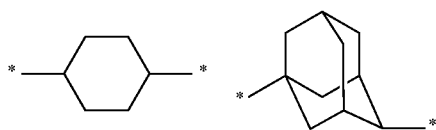

In some embodiments, the invention is directed to compounds represented by Formula IIIa, IIIb or IIIc:

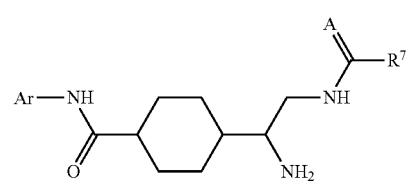

IIIa

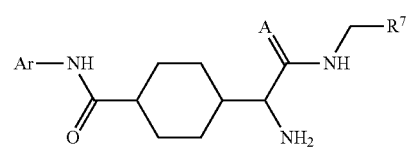

IIIb

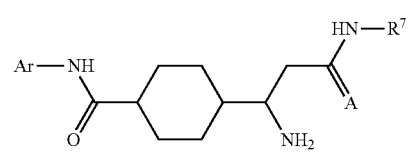

IIIc wherein Ar, A, and R⁷ are as defined therein;

or a stereoisomer, tautomer, racemate, metabolite, pro- or pre-drug, salt, hydrate, or solvate thereof.

In some embodiments, the invention is directed to compounds represented by Formula IIId, IIIe, or IIIf:

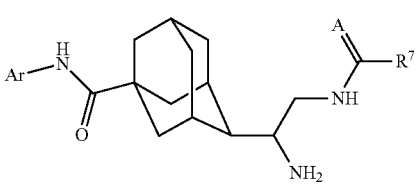

IIId

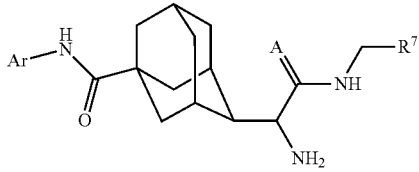

IIIe

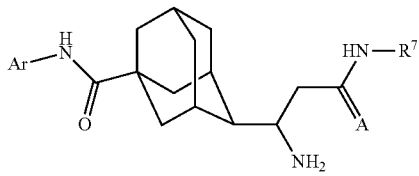

IIIf wherein Ar, A, and R⁷ are as defined therein;

or a stereoisomer, tautomer, racemate, metabolite, pro- or pre-drug, salt, hydrate, or solvate thereof.

In some embodiments, the invention is directed to compounds represented by Formula IVa, IVb or IVc:

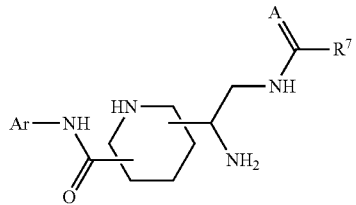

IVa

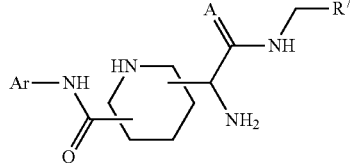

IVb

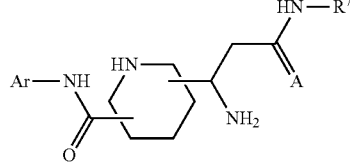

IVc wherein Ar, A, and R⁷ are as defined therein;

or a stereoisomer, tautomer, racemate, metabolite, pro- or pre-drug, salt, hydrate, or solvate thereof.

In some embodiments, the invention is directed to compounds represented by Formula Va, Vb or Vc:

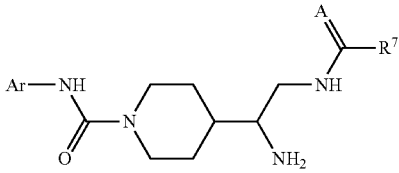

Va

-continued

Vb

Ar—NH—C(O)—N(piperidine)—CH(NH2)—C(A)=N—CH2—R7

Vc

Ar—NH—C(O)—N(piperidine)—CH(NH2)—CH2—C(A)=N—R7(HN)

wherein Ar, A, and R⁷ are as defined therein;
or a stereoisomer, tautomer, racemate, metabolite, pro- or pre-drug, salt, hydrate, or solvate thereof.

In one embodiment, the present invention relates to the compounds disclosed herein, wherein $R^6$ or $R^7$ are each independently selected from

[structures shown]

wherein
$Y^1$ is selected from —CH₂—, —CH($R^{14}$)—, —NH—, —O—, —S—, or —C(=O)—,
$Y^3$ is selected from —CH₂—, —CH₂—CH₂—, —O—, —S—, or —NH—,
$X^6$ is selected from N or CH,
$X^7$ is selected from N, C(=O), or CH,
$X^8$ is selected from N, NH or CH,
$X^9$ is selected from N or CH,
$X^{10}$ is selected from S, O or NH,
$X^{11}$ is selected from O, CH₂, C(=O), S or NH,
$X^{12}$ is selected from N, NH, O, S or CH,
$X^{13}$ is selected from NH, O, S or CH,
$X^{14}$ is selected from S, N, NH or CH,
$Z^1$ is selected from O or NH,
q is an integer selected from 1, 2, 3 or 4,
n is an integer selected from 1, 2, 3, 4, 5, 6 or 7,
wherein $R^{10}$ and $R^{11}$ are each independently a selected from hydrogen, alkyl, cycloalkyl, aryl, or aralkyl,
wherein $R^{12}$ is selected from aryl, cycloalkyl, heteroaryl or heterocyclyl, each being optionally substituted by one or more substituent (for example 1, 2, 3 or 4) selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl,
r is an integer selected from 0, 1, 2 or 3,
wherein $R^{13}$ and $R^{14}$ are each independently selected from hydrogen or alkyl,
or $R^{13}$ and $R^{14}$ form together with the carbon atoms to which they are attached form an aryl, an heteroaryl, a cycloalkyl or a heterocyclyl,
or r is 2 and two $R^{13}$ form together with the carbon atoms to which they are attached form an aryl, an heteroaryl, a cycloalkyl or a heterocyclyl,
wherein $R^{15}$ and $R^{16}$ together with the carbon atom to which they are attached form an aryl, a cycloalkyl, a heteroaryl a heterocyclyl, each being optionally substituted with one or more substituent (for example 1, 2, 3 or 4) selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl,
s is an integer selected from 0, 1, 2, 3 or 4,
wherein $R^{17}$ is selected from halo, or a group selected from alkenylaminooxy, alkoxy, alkyl, alkylamino, alkylaminosulfonyl, alkylcarbonyl, alkylcarbonylamino, alkyloxyaminoalkenyl, alkyloxycarbonyl, alkylsulfonyl, alkylsulfonylamino, alkylthio, amino, aralkyl, aryl, arylalkenylaminooxy, arylamino, arylaminosulfonyl, arylcarbonyl, arylcarbonylamino, aryloxy, cyano, cycloalkyl, haloalkoxy, haloalkyl, haloaryl, heteroaryl, heteroarylalkenylaminooxy, heteroarylalkyl, heteroarylcarbonylamino, heterocyclyl, hydroxyalkyl, nitro, oxo, sulfonyl, or two $R^{17}$ together with the atoms to which they are attached form an aryl, heteroaryl, cycloalkyl, or heterocyclyl, each group being optionally substituted with one or more substituents (for example 1, 2, 3 or 4) selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl,
wherein $R^{18}$ and $R^{19}$ are each independently selected from hydrogen, alkyl, cycloalkyl, cycloalkylalkyl, aryl, aralkyl, heteroaryl or heteroarylalkyl,
wherein $R^{20}$ is selected from hydrogen, or a group selected from alkyl, cycloalkyl, alkylaminoalkyl, alkylamino, alkylcarbonylamino, alkylcarbonylaminoalkyl, alkylsulfonyl, alkylsulfonylamino, alkylsulfonylaminoalkyl, amino, aminoalkyl, heterocyclyl, heterocyclylalkyl, cyano, cyanoalkyl, hydroxyl, hydroxyalkyl, alkoxy, alkoxyalkyl, alkoxycarbonyl, carboxy, alkoxycarbonylalkyl, aryl, aralkyl, heteroaryl, heteroarylalkyl, each group being optionally substituted by one or more substituent (for example 1, 2, 3 or 4) selected from halo, alkoxy, alkyl, alkylamino, alkylcarbonyl, alkylheteroaryl, alkylsuphonyl, aralkyl, aryl, arylamino, aryloxy, cyano, haloalkoxy, haloalkyl, heteroaryl, heteroarylalkyl, heteroarylcarbonyl, heterocyclyl, hydroxy, nitro, oxo, or sulfonyl,
wherein $R^{21}$ is selected from alkyl, aryl, alkylcarbonyl, heteroaryl or heteroarylcarbonyl.

In some embodiments, Ar is 1H-pyrrolo[2,3-b]pyridin-4-yl or pyridin-4-yl.

Specific compounds of the invention include the compounds exemplified in Tables 1, 2 and 3:

TABLE 1

| Compound |
|----------|

TABLE 1-continued

| Compound |
|---|

TABLE 1-continued
Compound
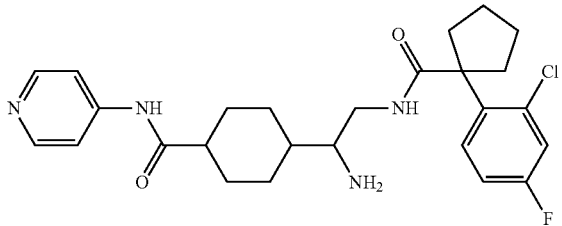
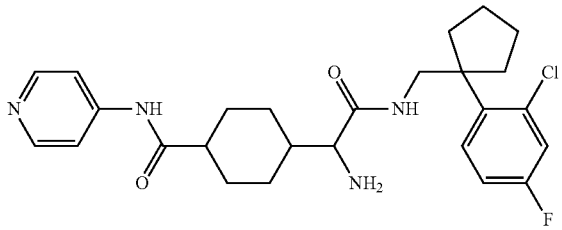 [SMILES: NC(C(=O)NCC1(c2ccc(F)cc2Cl)CCCC1)C1CCC(C(=O)Nc2ccncc2)CC1]
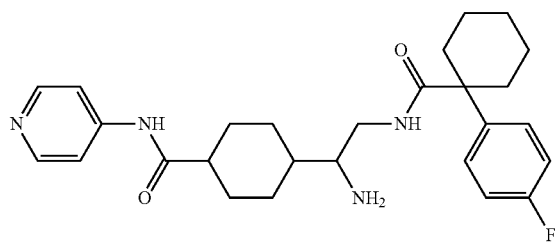
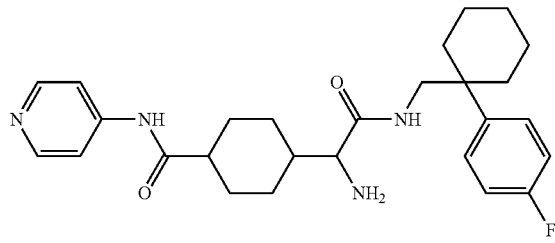 [SMILES: NC(C(=O)NCC1(c2ccc(F)cc2)CCCCC1)C1CCC(C(=O)Nc2ccncc2)CC1]
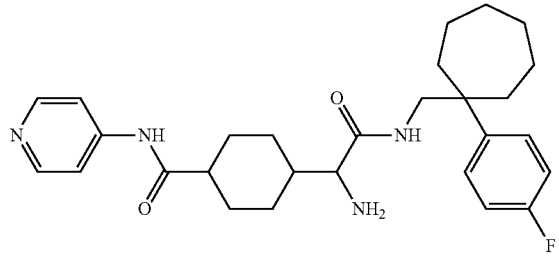
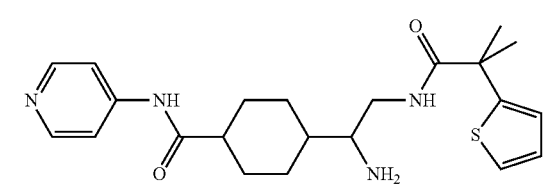
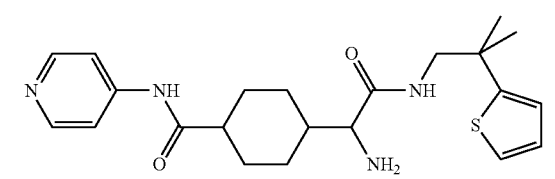

TABLE 1-continued
Compound
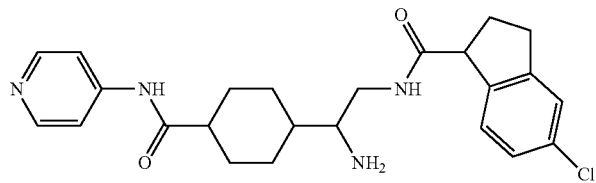 [SMILES: NC(CNC(=O)C1CCc2cc(Cl)ccc21)C1CCC(C(=O)Nc2ccncc2)CC1]
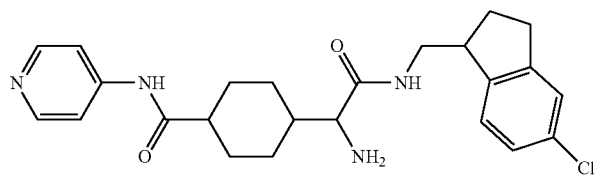
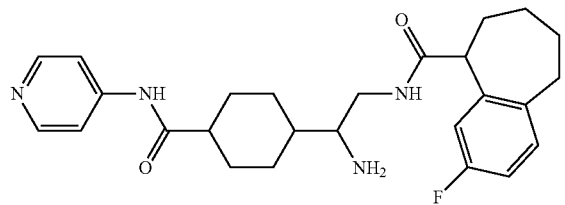 [SMILES: NC(CNC(=O)C1CCCCc2ccc(F)cc21)C1CCC(C(=O)Nc2ccncc2)CC1]
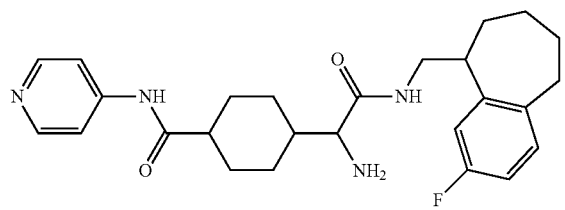 [SMILES: NC(C(=O)NCC1CCCCc2ccc(F)cc21)C1CCC(C(=O)Nc2ccncc2)CC1]
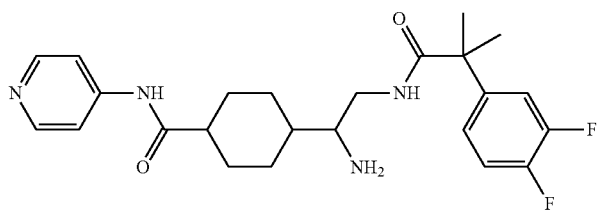
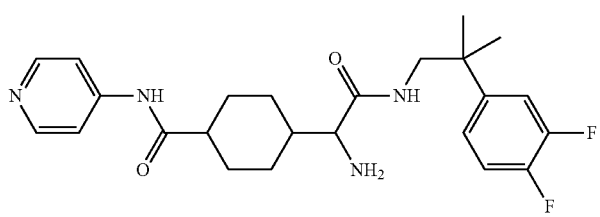 [SMILES: NC(C(=O)NCC1(c2ccc(F)c(F)c2)CC1)C1CCC(C(=O)Nc2ccncc2)CC1]
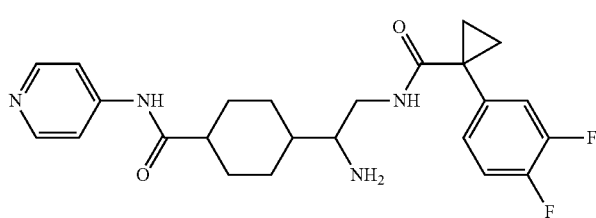

TABLE 1-continued

Compound

TABLE 1-continued

Compound

TABLE 1-continued

Compound

TABLE 1-continued

Compound

TABLE 1-continued
Compound
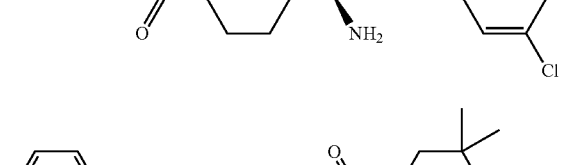
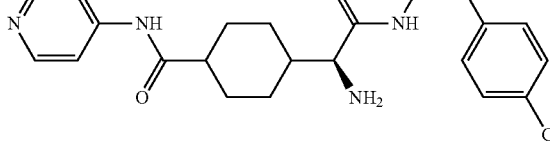
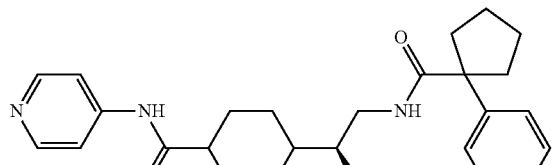
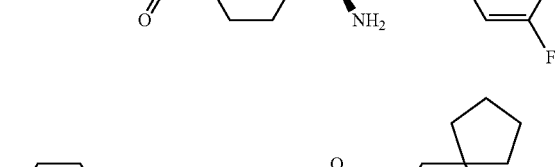
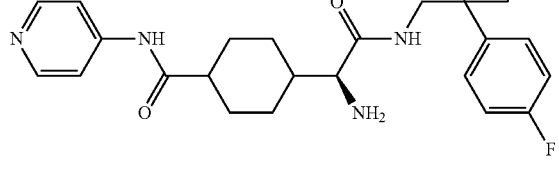
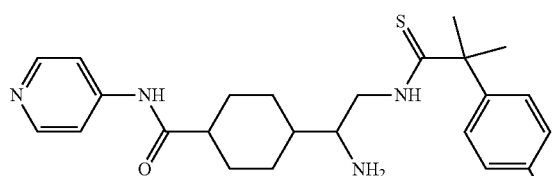
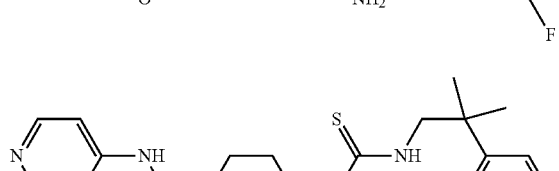

TABLE 1-continued

Compound

[Chemical structure: N-(pyridin-4-yl)-4-(1-amino-2-((2,3-dihydrobenzofuran-3-carboxamido))ethyl)cyclohexane-1-carboxamide]

[Chemical structure: N-(pyridin-4-yl)-4-(1-amino-2-((4-fluorobenzyl)amino)-3-oxopropyl)cyclohexane-1-carboxamide]

[Chemical structure: N-(pyridin-4-yl)-4-(1-amino-3-((2,3-dihydrobenzofuran-3-yl)amino)-3-oxopropyl)cyclohexane-1-carboxamide]

TABLE 2

Compound

[Chemical structure: adamantane derivative with pyridin-4-yl carboxamide and 1-(4-chlorophenyl)cyclopropane-1-carboxamide]

[Chemical structure: adamantane derivative with pyridin-4-yl carboxamide and (1-(4-chlorophenyl)cyclopropyl)methylamide]

[Chemical structure: adamantane derivative with pyridin-4-yl carboxamide and 2-ethyl-2-phenylbutanamide]

TABLE 2-continued
Compound
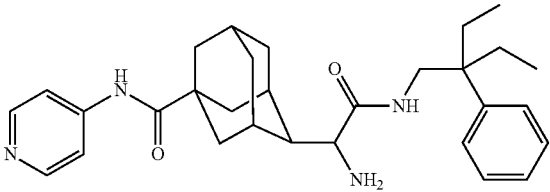 [SMILES: CCC(CC)(CNC(=O)C(N)C1C2CC3CC1CC(C(=O)Nc1ccncc1)(C3)C2)c1ccccc1]
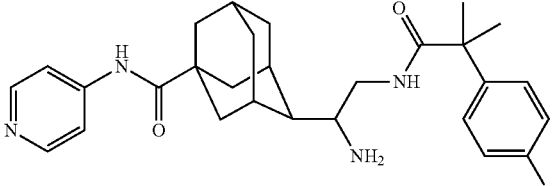
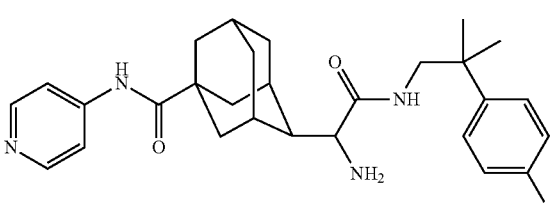
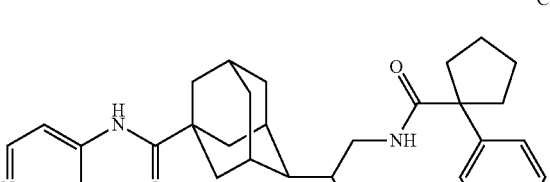
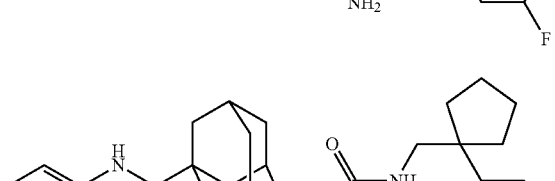
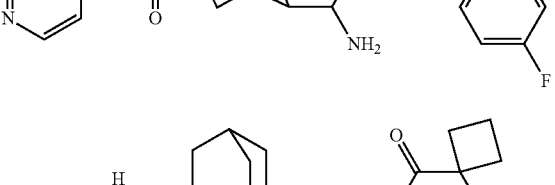
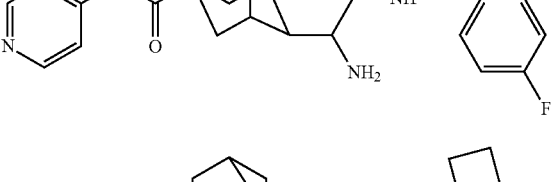

TABLE 2-continued
Compound
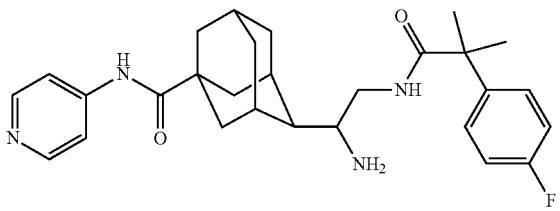 [SMILES: CC(C)(C(=O)NCC(N)C1C2CC3CC1CC(C(=O)Nc1ccncc1)(C3)C2)c1ccc(F)cc1]
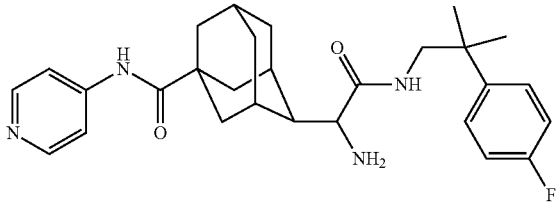 [SMILES: CC(C)(CNC(=O)C(N)C1C2CC3CC1CC(C(=O)Nc1ccncc1)(C3)C2)c1ccc(F)cc1]
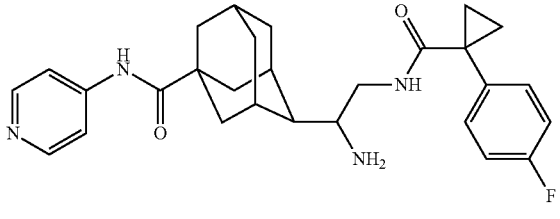 [SMILES: NC(CNC(=O)C1(c2ccc(F)cc2)CC1)C1C2CC3CC1CC(C(=O)Nc1ccncc1)(C3)C2]
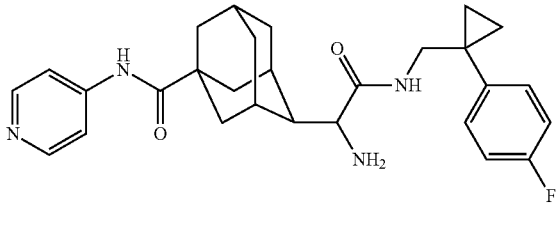
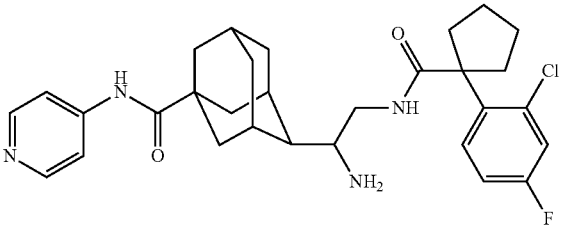 [SMILES: NC(CNC(=O)C1(c2ccc(F)cc2Cl)CCCC1)C1C2CC3CC1CC(C(=O)Nc1ccncc1)(C3)C2]
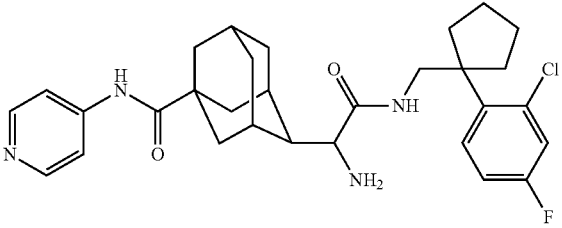 [SMILES: NC(C(=O)NCC1(c2ccc(F)cc2Cl)CCCC1)C1C2CC3CC1CC(C(=O)Nc1ccncc1)(C3)C2]

TABLE 2-continued

| Compound |
| --- |

TABLE 2-continued
Compound
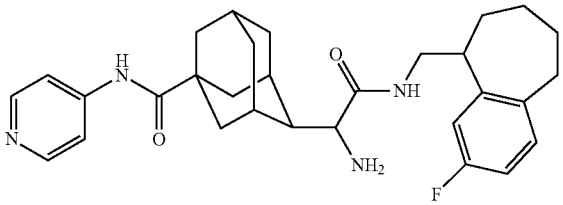 [SMILES: NC(C(=O)NCC1CCCCc2ccc(F)cc21)C1C2CC3CC1CC(C(=O)Nc1ccncc1)(C3)C2]
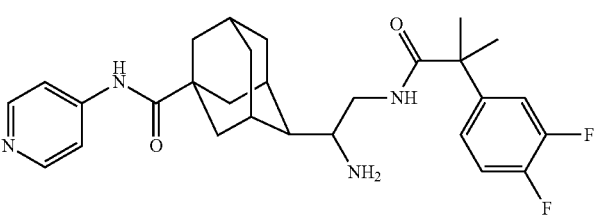
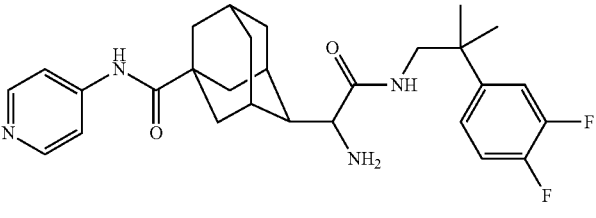 [SMILES: CC(C)(CNC(=O)C(N)C1C2CC3CC1CC(C(=O)Nc1ccncc1)(C3)C2)c1ccc(F)c(F)c1]
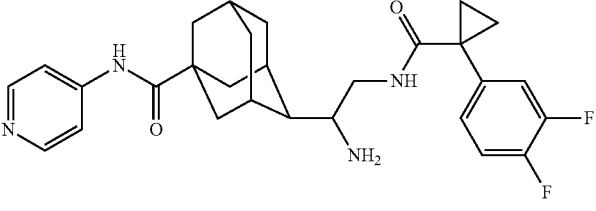 [SMILES: NC(CNC(=O)C1(c2ccc(F)c(F)c2)CC1)C1C2CC3CC1CC(C(=O)Nc1ccncc1)(C3)C2]
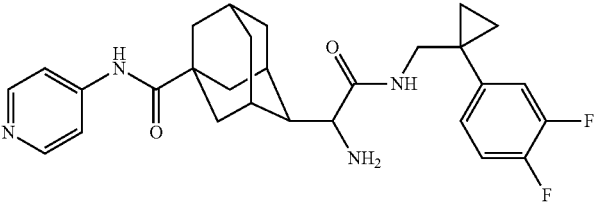
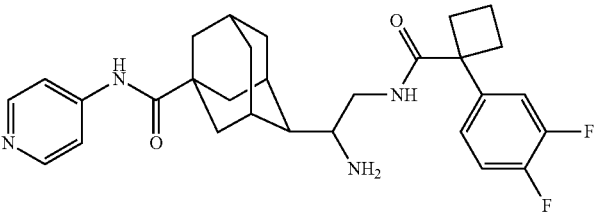 [SMILES: NC(CNC(=O)C1(c2ccc(F)c(F)c2)CCC1)C1C2CC3CC1CC(C(=O)Nc1ccncc1)(C3)C2]
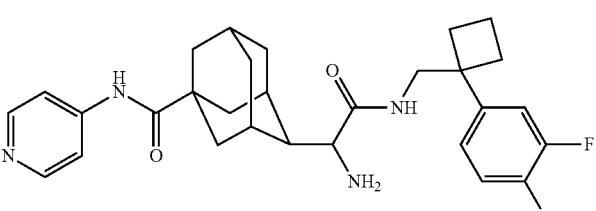

TABLE 2-continued
| Compound |
|---|
| 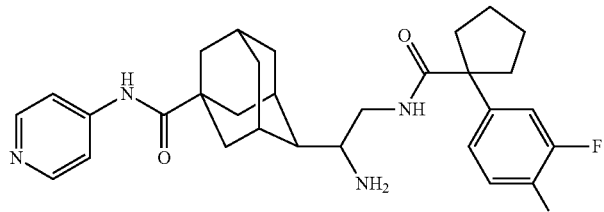 |
| 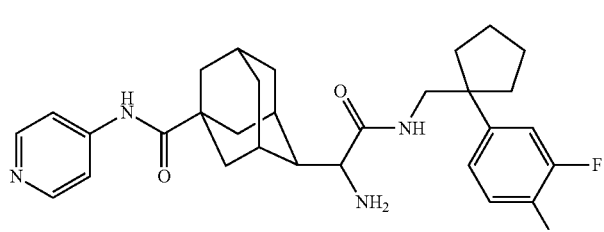 |
| 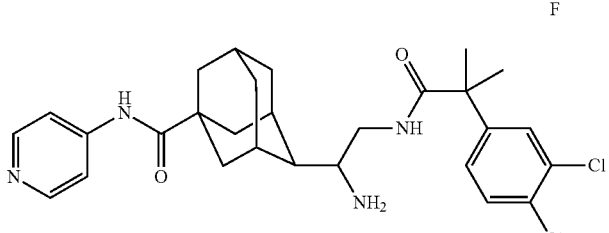 |
| 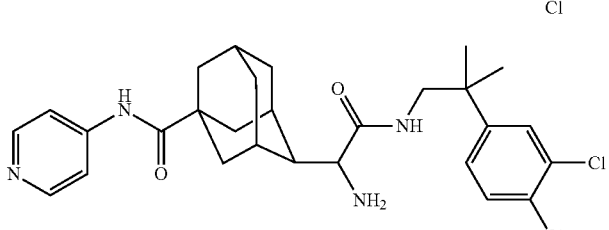 |
| 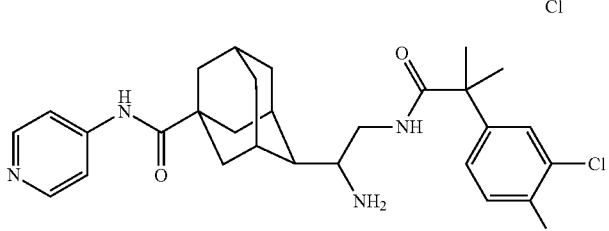 |
| 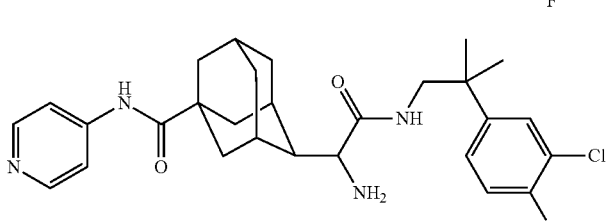 |
| 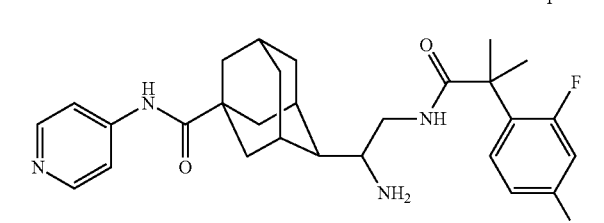 |

TABLE 2-continued

Compound

TABLE 2-continued
Compound
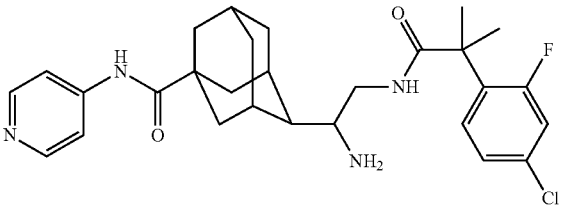
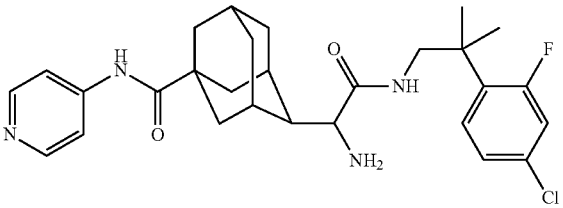
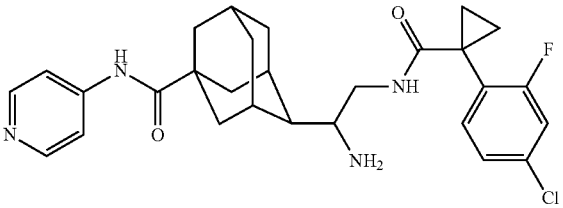 [SMILES: NC(CNC(=O)C1(c2ccc(F)cc2Cl)CC1)C1C2CC3CC1CC(C(=O)Nc1ccncc1)(C3)C2]
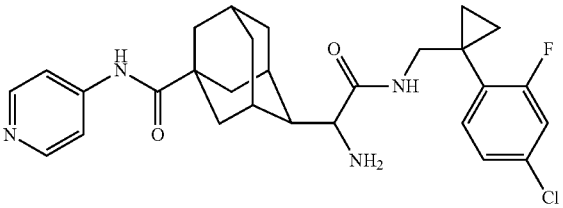 [SMILES: NC(C(=O)NCC1(c2ccc(F)cc2Cl)CC1)C1C2CC3CC1CC(C(=O)Nc1ccncc1)(C3)C2]
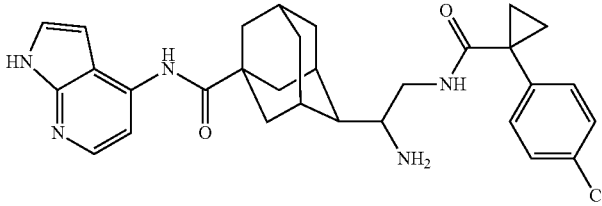 [SMILES: NC(CNC(=O)C1(c2ccc(Cl)cc2)CC1)C1C2CC3CC1CC(C(=O)Nc1ccnc4[nH]ccc14)(C3)C2]
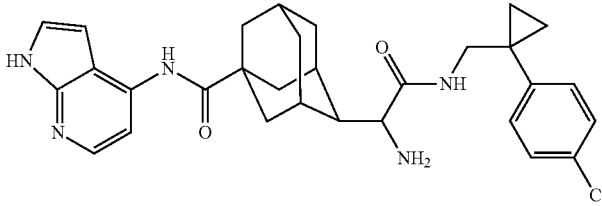 [SMILES: NC(C(=O)NCC1(c2ccc(Cl)cc2)CC1)C1C2CC3CC1CC(C(=O)Nc1ccnc4[nH]ccc14)(C3)C2]
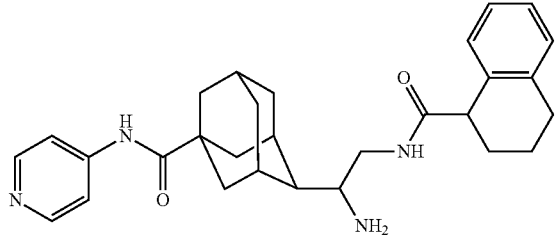 [SMILES: NC(CNC(=O)C1CCCc2ccccc21)C1C2CC3CC1CC(C(=O)Nc1ccncc1)(C3)C2]

TABLE 2-continued

Compound

TABLE 2-continued
Compound
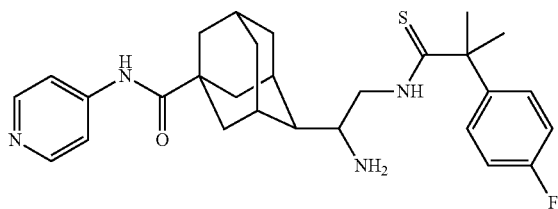
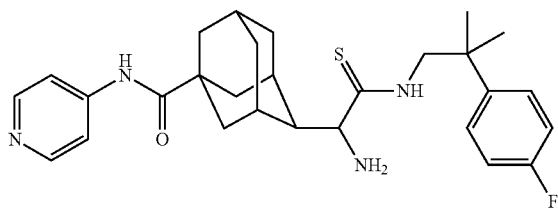 [SMILES: CC(C)(CNC(=S)C(N)C1C2CC3CC1CC(C(=O)Nc1ccncc1)(C3)C2)c1ccc(F)cc1]
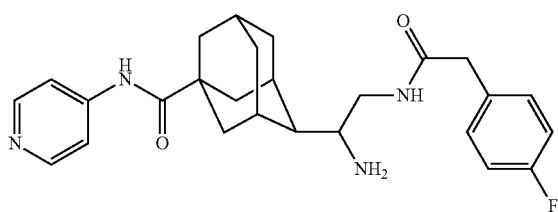 [SMILES: NC(CNC(=O)Cc1ccc(F)cc1)C1C2CC3CC1CC(C(=O)Nc1ccncc1)(C3)C2]
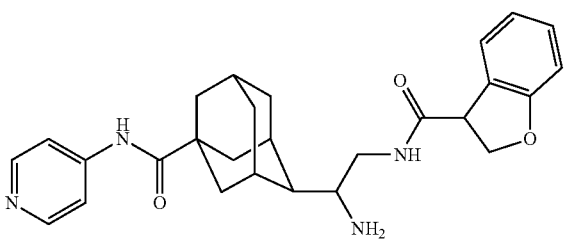 [SMILES: NC(CNC(=O)C1COc2ccccc21)C1C2CC3CC1CC(C(=O)Nc1ccncc1)(C3)C2]
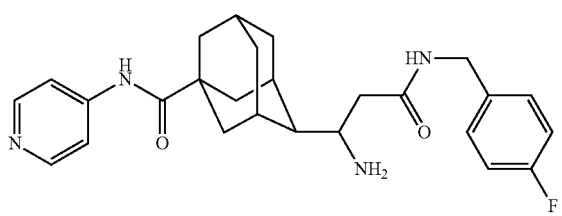 [SMILES: NC(CC(=O)NCc1ccc(F)cc1)C1C2CC3CC1CC(C(=O)Nc1ccncc1)(C3)C2]
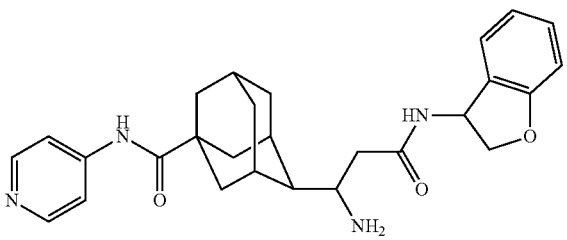 [SMILES: NC(CC(=O)NC1COc2ccccc21)C1C2CC3CC1CC(C(=O)Nc1ccncc1)(C3)C2]

TABLE 3

Compound

TABLE 3-continued
| Compound |
|---|
| 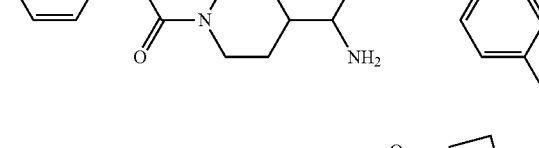 |
| 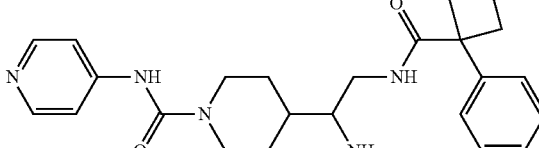 |
| 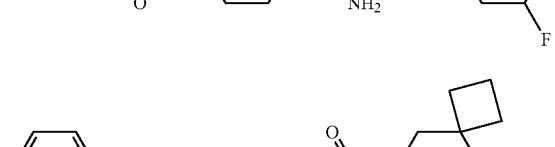 |
| 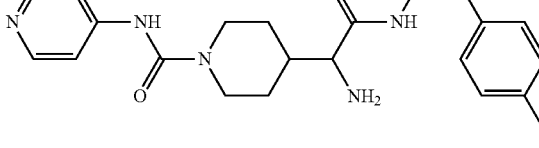 |
| 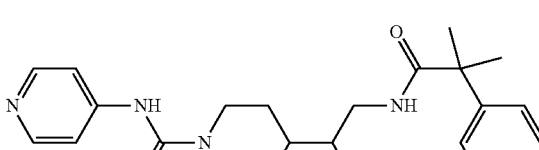 |
| 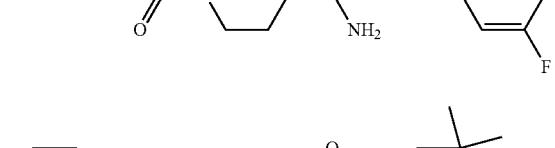 |

TABLE 3-continued
Compound
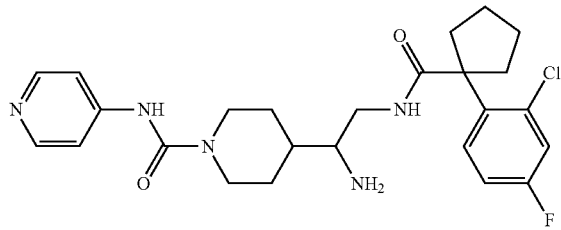
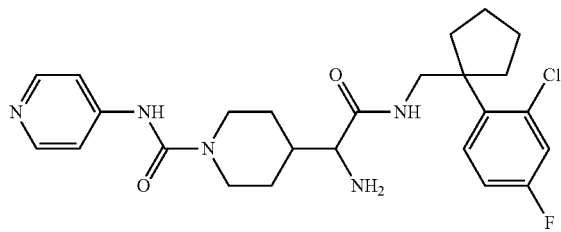 [SMILES: NC(C(=O)NCC1(c2ccc(F)cc2Cl)CCCC1)C1CCN(C(=O)Nc2ccncc2)CC1]
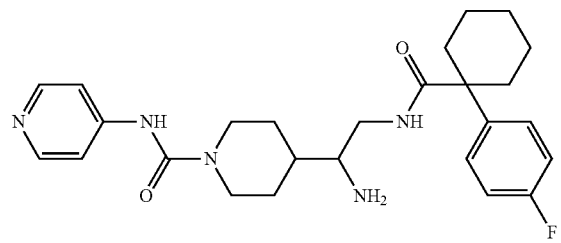 [SMILES: NC(CNC(=O)C1(c2ccc(F)cc2)CCCCC1)C1CCN(C(=O)Nc2ccncc2)CC1]
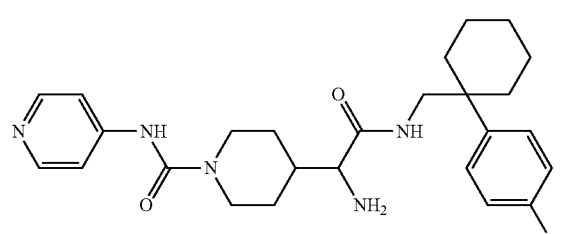
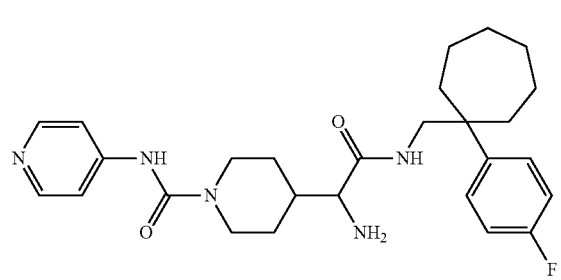 [SMILES: NC(C(=O)NCC1(c2ccc(F)cc2)CCCCCC1)C1CCN(C(=O)Nc2ccncc2)CC1]
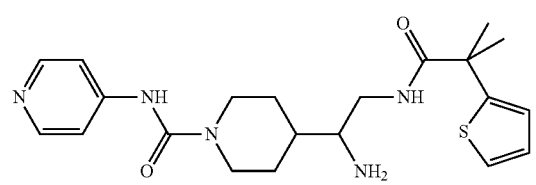 [SMILES: CC(C)(C(=O)NCC(N)C1CCN(C(=O)Nc2ccncc2)CC1)c1cccs1]
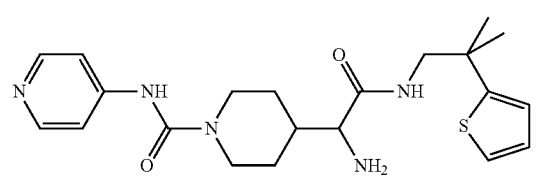

TABLE 3-continued
Compound
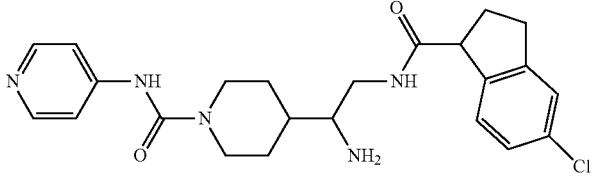
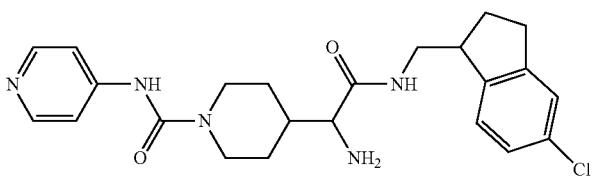 [SMILES: NC(C(=O)NCC1CCc2cc(Cl)ccc21)C1CCN(C(=O)Nc2ccncc2)CC1]
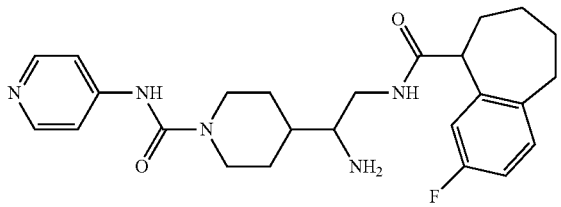
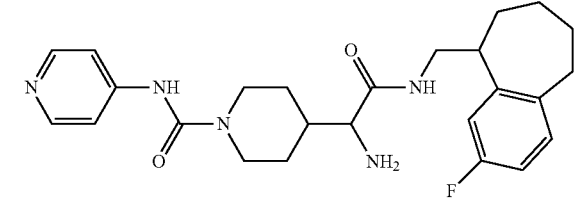
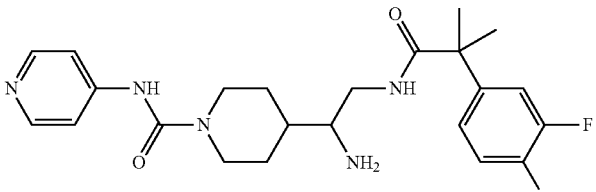
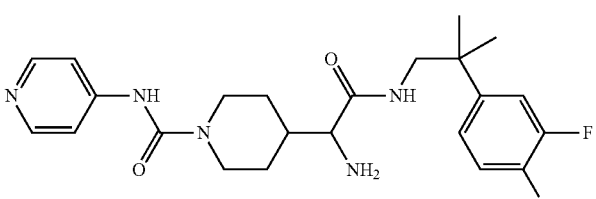
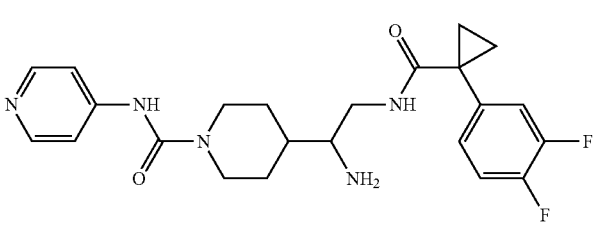

TABLE 3-continued

Compound

TABLE 3-continued
| Compound |
|---|
| 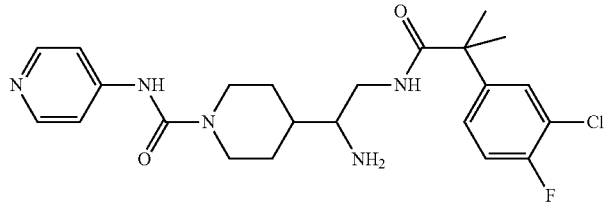 [SMILES: CC(C)(C(=O)NCC(N)C1CCN(C(=O)Nc2ccncc2)CC1)c1ccc(F)c(Cl)c1] |
| 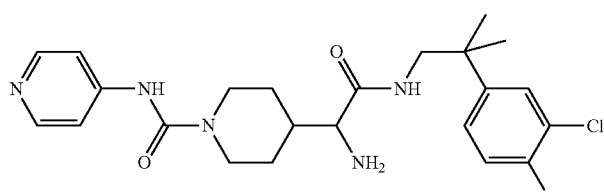 |
| 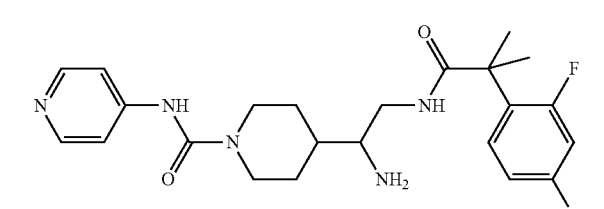 |
| 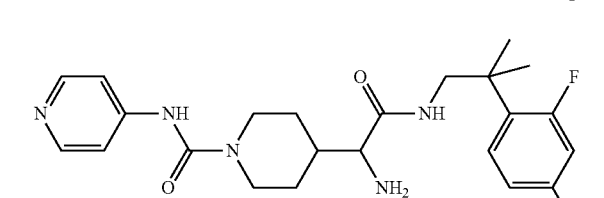 |
| 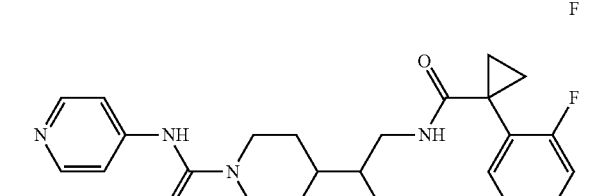 |
| 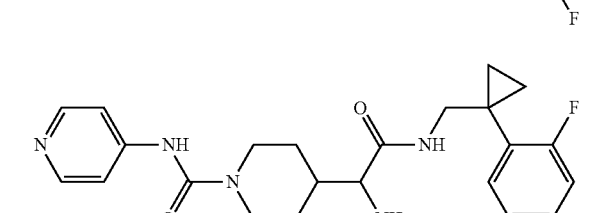 |
| 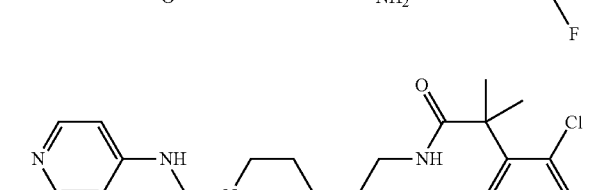 |

TABLE 3-continued

| Compound |
|---|

TABLE 3-continued

Compound

TABLE 3-continued

Compound

TABLE 3-continued

Compound

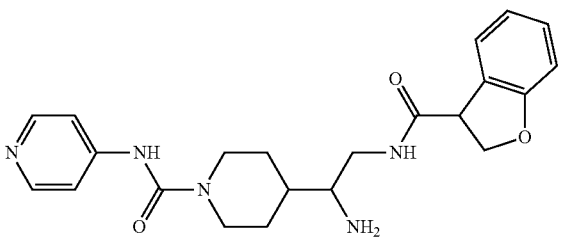

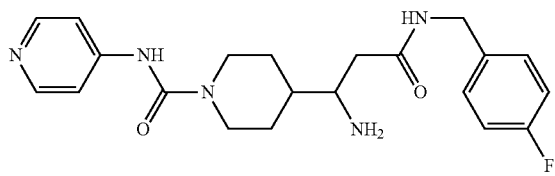 [SMILES: NC(CC(=O)NCc1ccc(F)cc1)C1CCN(C(=O)Nc2ccncc2)CC1]

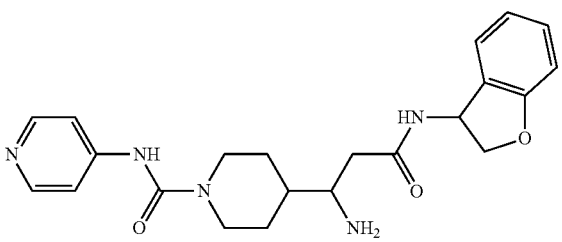 [SMILES: NC(CC(=O)NC1COc2ccccc21)C1CCN(C(=O)Nc2ccncc2)CC1]

or a stereoisomer, tautomer, racemate, metabolite, pro- or pre-drug, salt, hydrate, or solvate thereof.

It is clear to a person skilled in the art that the compounds of Formula I or II contain at least one asymmetric center and thus may exist as different stereoisomers forms. This asymmetric center is indicated with an asterisk (*) in the figure below.

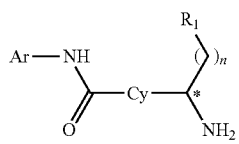

I

II

The absolute configuration of each asymmetric center that may be present in the compounds of Formula I or II may be indicated by the stereochemical descriptors R and S. When two chiral centers are present in the compound, in the configuration R,R for example the first letter refers to the configuration of the carbon bearing the amine group (*).

In a particular embodiment of the present invention, as illustrated hereunder at least one enantiomer is preferred for PKC and the other ones are preferred for ROCK In a particular embodiment, for the compounds when Cy is

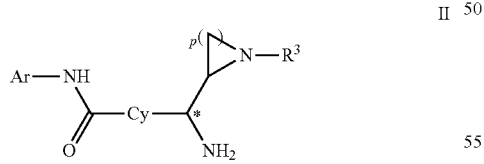

and $R^5$ and/or $R^6$ do not contain any chiral centers, the carbon atom marked with the asterisk (*) preferably has the configuration shown in the figure below for PKC inhibition, and the opposite configuration for ROCK inhibition. The trend is contemplated to be the inverse when Cy is a 5-membered heterocycle.

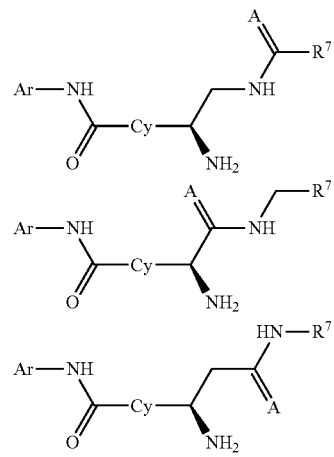

Compositions

The compounds of the invention may be in the form of pharmaceutically and/or veterinary acceptable salts, as generally described below. Some preferred, but non-limiting examples of suitable pharmaceutically acceptable organic and/or inorganic acids are as hydrochloric acid, hydrobromic acid, sulfuric acid, nitric acid, acetic acid and citric acid, as well as other pharmaceutically acceptable acids known per se (for which reference is made to the prior art referred to below).

When the compounds of the invention contain an acidic group as well as a basic group the compounds of the invention may also form internal salts, and such compounds are within the scope of the invention. When the compounds of the invention contain a hydrogen-donating heteroatom (e.g. NH), the invention also covers salts and/or isomers formed by transfer of said hydrogen atom to a basic group or atom within the molecule.

In addition, although generally, with respect to the salts of the compounds of the invention, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I or II above.

The invention also generally covers all pharmaceutically acceptable pre-drugs and pro-drugs of the compounds of Formula I or II, for which general reference is made to the prior art cited hereinbelow.

The term "pro-drug" as used herein means the pharmacologically acceptable derivatives such as esters, amides and phosphates, such that the resulting in vivo biotransformation product of the derivative is the active drug. The reference by Goodman and Gilman (The Pharmacological Basis of Therapeutics, 8th Ed, McGraw-Hill, Int Ed 1992, "Biotransformation of Drugs", p 13-15) describing pro-drugs generally is hereby incorporated. Pro-drugs of the compounds of the invention can be prepared by modifying functional groups present in said component in such a way that the modifications are cleaved, either in routine manipulation or in vivo, to the parent component. Typical examples of pro-drugs are described for instance in WO 99/33795, WO 99/33815, WO 99/33793 and WO 99/33792 all incorporated herein by reference. Pro-drugs are characterized by increased bio-availability and are readily metabolized into the active inhibitors in vivo. The term "pre-drug", as used herein, means any compound that will be modified to form a drug species, wherein the modification may take place either inside or outside of the body, and either before or after the pre-drug reaches the area of the body where administration of the drug is indicated.

As described above, some of the compounds of the invention may contain one or more asymmetric carbon atoms that serve as a chiral center, which may lead to different optical forms (e.g. enantiomers or diastereomers). The invention comprises all such optical forms in all possible configurations, as well as mixtures thereof.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereomers) and isomers that correspond to the presence of the same substituents on different positions of the rings present in the compounds of the invention. All such possible isomers, tautomers and mixtures thereof are included within the scope of the invention.

Compound Preparation

The compounds of Formula I or II may be prepared as described in the experimental section below using methods and chemistries with which those skilled in the art shall be familiar.

It will also be clear that when the desired compounds of the invention, and/or the starting materials, precursors and/or intermediates used in the preparation thereof, contain functional groups that are sensitive to the reaction conditions used in the preparation of the compounds of the invention (i.e. that would undergo undesired reactions under those conditions if they were not suitably protected) can be protected during said reaction with one or more suitable protective group, which protective group can then be suitably removed after either completion of said reaction and/or as a later or final step in the preparation of the compounds of the invention. Protected forms of the inventive compounds are included within the scope of the present invention. Suitable protective groups, as well as methods and conditions for inserting them and removing them, will be clear to the skilled person and are generally described in the standard handbooks of organic chemistry, such as Greene and Wuts, "Protective groups in organic synthesis", 3rd Edition, Wiley and Sons, 1999, which is incorporated herein by reference in its entirety. It will also be clear to the skilled person that compounds of the invention in which one or more functional groups have been protected with suitable functional groups can find use as intermediates in the production and/or synthesis of the compounds of the invention, and as such form a further aspect of the invention.

Generally, the compounds of the invention are prepared from amine- or carboxylic acid-containing intermediates described hereinafter which may be reacted with complementary reactive molecules so as to form the desired compound. The intermediates and complementary reactive molecules are either commercially available or may be easily prepared by the skilled person.

Exemplary compounds according to Formula I (e.g., Formula Ia, and compounds obtainable therewith wherein A is O, and wherein Ar, Cy, $R^5$ and $R^7$ have the same meaning as that defined above, and $R^{30}$ is an alkyl group, can be synthesized according to the methods shown below in Scheme A.

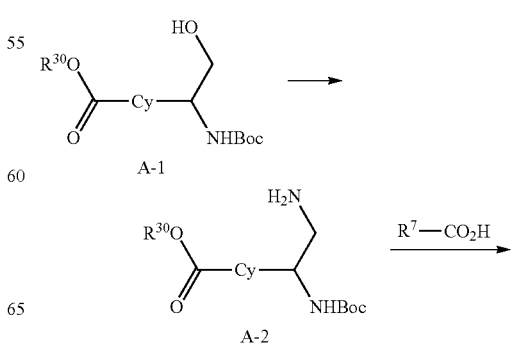

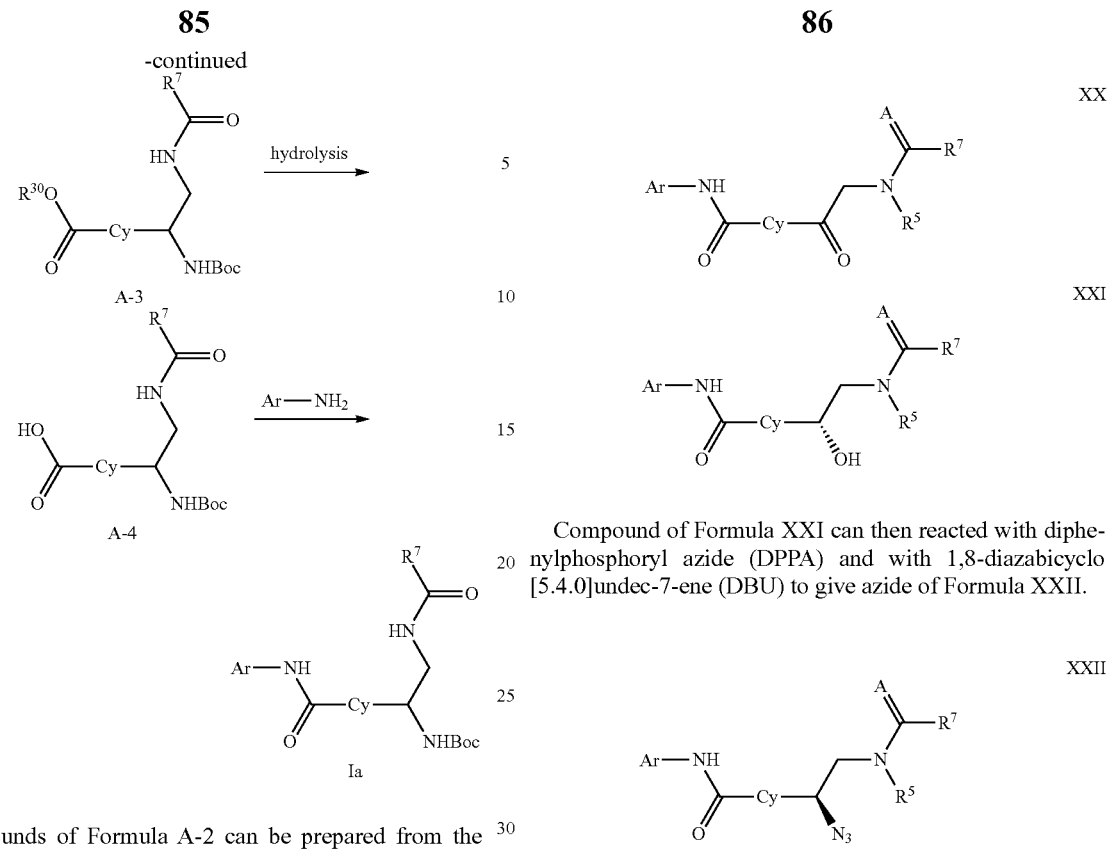

Compounds of Formula A-2 can be prepared from the corresponding alcohol A-1 under standard substitution reaction condition with a suitable amine reagent using methods known in the art. Exemplary reaction condition can comprise an amine nucleophile, such as an azide (e.g., diphenylphosphoryl azide (DPPA)) or phthalimide, which can be subsequently converted to the free amine. In some embodiments a coupling agent, such as diisopropyl azodicarboxylate (DIAD) or diethyl azodicarboxylate (DEAD) can be used. Amide A-3 can be provided from amine A-2 using a suitable carboxyl derivative of a compound of formula $R^7$—COOH (e.g., an acid, ester, carbonate, anhydride, etc.), where $R^7$ is as described hereinabove. Coupling agents such as O-benzotriazole-N,N,N',N'-tetramethyl-uronium-hexafluoro-phosphate (HBTU) can be used with a suitable base, such as diisopropylethylamine (DIPEA). Suitable coupling reaction conditions are well known in the art. Hydrolysis of the ester under standard hydrolysis reaction conditions yields carboxylic acid A-4. Compounds of Formula Ia can be provided from compound A-4 under standard amidation conditions using a suitable aryl amine of formula Ar—$NH_2$, where Ar is as described herein above, followed by tert-butoxycarbonyl (Boc) deprotection (e.g. trifluoroacetic acid). Suitable amidation reaction conditions can comprise coupling agents such as O-benzotriazole-N,N,N',N'-tetramethyl-uronium-hexafluoro-phosphate (HBTU) and N-hydroxybenzotriazole (HOBt) can be used with a suitable base, such as diisopropylethylamine (DIPEA).

According to a particular embodiment, the present invention encompasses the method for the preparation of enantiomers of Formula Ia, and compounds obtainable therewith wherein Cy is cyclohexylene, A is O, and wherein Ar, $R^5$ and $R^7$ have the same meaning as that defined above. Enantiomers of Formula Ia with Cy being cyclohexylene and A being O can be obtained by reacting a compound of Formula XX with Noyori's catalyst (JACS, 1996, 118, 2521; JACS, 2005, 127, 4596), thereby obtaining compound of Formula XXI.

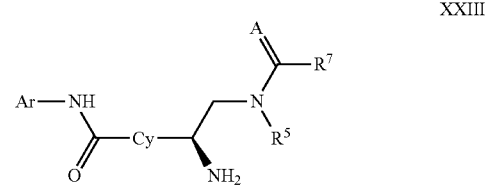

Compound of Formula XXI can then reacted with diphenylphosphoryl azide (DPPA) and with 1,8-diazabicyclo[5.4.0]undec-7-ene (DBU) to give azide of Formula XXII.

The azide of Formula XXII can then reacted with Pd/C to give the amine of Formula XXIII.

Exemplary compounds according to Formula I (e.g., Formula Ib, and compounds obtainable therewith wherein A is O, and wherein Ar, Cy, $R^5$ and $R^7$ have the same meaning as that defined above can be synthesized according to the methods shown below in Scheme B.

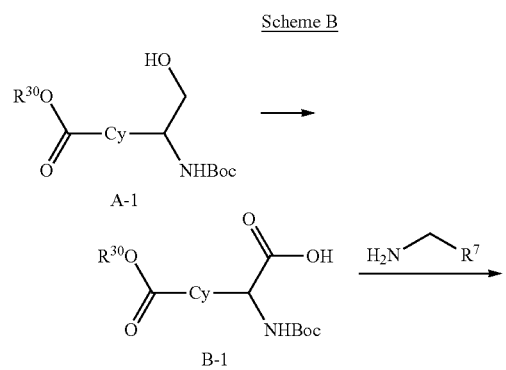

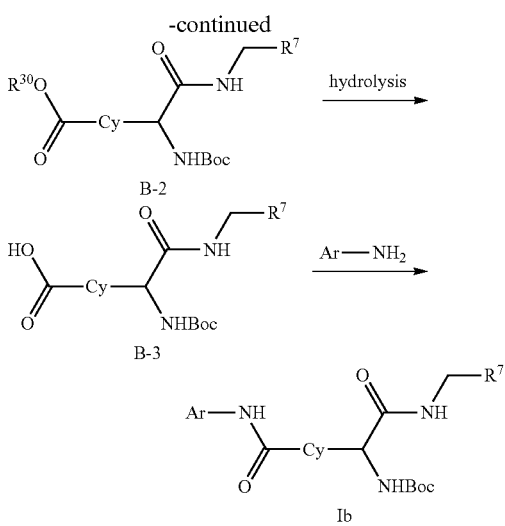

Amino acids of Formula B-1 can be prepared from the corresponding amino alcohol A-1 under standard oxidation reaction conditions using a suitable oxidant, such as a peroxide, TEMPO, etc. Amide B-2 can be provided via a reagent of formula $NH_2$—$CH_2$—$R^7$ (where $R^7$ is as described hereinabove) under suitable amidation reaction conditions. Suitable amidation reaction conditions can comprise coupling agents such as O-benzotriazole-N,N,N',N'-tetramethyl-uronium-hexafluoro-phosphate (HBTU) and N-hydroxybenzotriazole (HOBt) can be used with a suitable base, such as diisopropylethylamine (DIPEA). Hydrolysis of the ester of B-2 can proceed under standard basic conditions (e.g., ethanolic NaOH) to yield the corresponding carboxylic acid B-3. Compounds of Formula Ib can be provided from compound B-3 under standard amidation conditions using a suitable aryl amine of formula Ar—$NH_2$, where Ar is as described herein above, followed by tert-butoxycarbonyl (Boc) deprotection (e.g. trifluoroacetic acid). Suitable amidation reaction conditions can comprise coupling agents such as O-benzotriazole-N,N,N',N'-tetramethyl-uronium-hexafluoro-phosphate (HBTU) and N-hydroxybenzotriazole (HOBt) can be used with a suitable base, such as diisopropylethylamine (DIPEA).

In Schemes A and B, above, compounds of formula A-1, Ar—$NH_2$, $NH_2$—$R^7$ and $NH_2$—$CH_2$—$R^7$ are either commercially available from sources such as Aldrich®, USA, or can be prepared using methods known to one of skill in the art. For example, Compounds of formula A-1 can be prepared via hydrogenation of the corresponding phenylene compound (See, Examples 1 and 2).

Methods of Use

The compounds of the invention may be used for the inhibition of kinases in vitro or in vivo, preferably in vitro, for modulating biological pathways and/or processes in which such kinases are involved, and/or to prevent and/or treat diseases or disorders in which such kinases, pathways and/or processes are involved.

In a particular embodiment, the compounds of the invention may be used for the inhibition of PKC epsilon in vitro or in vivo, preferably in vitro, for modulating biological pathways and/or processes in which PKC epsilon is involved, and/or to prevent and/or treat diseases or disorders in which PKC epsilon, pathways and/or processes are involved.

According to one preferred, but non-limiting embodiment, the compounds of the invention may be used for any purposes known per se for inhibitors of PKC epsilon.

In one embodiment, the present invention is directed to compounds of Formula I or II that inhibit PKC epsilon in the inhibition assay for PKC epsilon (described below). In some embodiments, the compounds exhibits an $IC_{50}$ value of less than 100 µM, or less than 50 µM, or less than 10 µM, or less than 5 µM, or less than 1 µM, or less than 0.1 µM, or less than 10 nM, or less than or 1 nM, as determined by a suitable assay, such as the assay disclosed herein below.

The present invention also relates to the use of the compounds of Formula I or II above in (the preparation of a composition for) inhibiting PKC epsilon. Said inhibition may be effected in vitro and/or in vivo, and when effected in vivo, is preferably effected in a selective manner, as defined above. In another embodiment, the present invention also relates to the use of the compounds of Formula I or II above in (the preparation of a composition for) inhibiting PKC theta. Said inhibition may be effected in vitro and/or in vivo, and when effected in vivo, is preferably effected in a selective manner, as defined above.

Treatment of Pain

Pain is the most common reason why people seek medical attention and pain medications are among the most widely prescribed drugs. Most pain medications fall into 4 groups: non-steroidal anti-inflammatory drugs (NSAIDS), opioid analgesics, monoamine reuptake inhibitors, and anticonvulsants. However, these drugs are often only partially effective, and many have serious side effects that can limit their use, such as GI bleeding, renal insufficiency, cardiovascular events, autonomic dysfunction sedation, ataxia, and in the case of opiates, risk of addiction. Because of these limitations, there is still a need for new pain mediations with different mechanisms of action and improved safety.

Accordingly, provided herein are compounds and compositions for inhibiting PKCε and reducing inflammatory and neuropathic pain in mammals. In certain embodiments, the mammals are humans.

Treatment of Addiction

In addition to its role in pain, PKCε has a striking effect on behavioral responses to ethanol. Thus, mice lacking PKCε show increased signs of ethanol intoxication, delayed development of acute tolerance to ethanol, and markedly reduced ethanol self-administration compared with wild type mice. They also show decreased self-administration of nicotine-containing solutions. These findings indicate that inhibitors of PKCε could be useful to substance abuse/disorders and alcohol use disorders.

In another embodiment, the present invention is directed to a method for treating a patient suffering from substance abuse and/or substance dependence, which method comprises administering an effective amount of a compound of the invention to said patient.

As used herein, the terms "substance abuse" and "substance dependence" refer to the consumption or self-administration of a substance at a level that interferes with physical health, mental health, and social, family, or job responsibilities. Substance abuse may result in tolerance to the effect of the substance and withdrawal symptoms when use is reduced or stopped. When an individual persists in use of a substance despite problems related to use of the substance, substance dependence may be diagnosed. Substance dependence may be a result of psychological or physical dependence.

Such substances can be substances, such as opioids (e.g., heroin, morphine, oxycodon, etc.), amphetamines, barbiturates, benzodiazepines, nicotine, cocaine, and methaqualone. In some embodiments, the substance is alcohol. In some embodiments, the substance is nicotine.

According to particularly preferred embodiments, the compounds of the invention are preferably used in the prevention and/or treatment of at least one disease or disorder selected from the group consisting of alcohol abuse and alcohol dependence and substance abuse and substance dependence. Accordingly, in one of its method embodiments, the present invention is directed to a method for treating a patient suffering from alcohol abuse and/or alcohol dependence, which method comprises administering an effective amount of a compound of the invention to said patient. In another of its method embodiments, the present invention is directed to a method for treating a patient suffering from nicotine abuse and/or nicotine dependence, which method comprises administering an effective amount of a compound of the invention to said patient. It is contemplated that the patient can be effectively treated using the dosing regimens disclosed herein.

As used herein, the terms "alcohol abuse" and "alcohol dependence" refer to the consumption of alcoholic beverages at a level that interferes with physical health, mental health, and social, family, or job responsibilities.

Other Treatments

In a further method embodiment, the present invention is directed to a method for treating a patient suffering from depression, which method comprises administering an effective amount of a compound of the invention to said patient.

According to particularly preferred embodiments, the compounds of the invention are preferably used in the prevention and/or treatment of at least one disease or disorder, preferably in which PKC epsilon is involved. According to an even more particularly preferred embodiment, the compounds of the invention may be used in the prevention and/or treatment of at least one disease or disorder in which the epsilon isoform of PKC is involved.

For example, the compounds of the invention may be used in the prevention and/or treatment of diseases and disorders such as:

metabolic diseases, such as:
(1) hyperglycemic conditions and/or other conditions and/or diseases that are (primarily) associated with (the response or sensitivity to) insulin, including but not limited to all forms of diabetes and disorders resulting from insulin resistance, such as Type I and Type II diabetes, as well as severe insulin resistance, hyperinsuhnemia, and hyperlipemia, e.g., obese subjects, and insulin-resistant diabetes, such as Mendenhall's Syndrome, Werner Syndrome, leprechaunism, lipoatrophic diabetes, and other hypoatrophies;
(2) conditions caused or usually associated with hyperglycemic conditions and/or obesity, such as hypertension, osteoporosis and/or lipodystrophy;
(3) so-called "metabolic syndrome" (also known as "Syndrome X") which is a condition where several of the following conditions coexist: hypertension, insulin resistance, diabetes, dyslipidemia, and/or obesity;
as well as various diseases and disorders known per se, and may also be used also for preventing, treating and/or alleviating complications and/or symptoms associated with these diseases and disorders, anxiety, addiction such as alcohol abuse or drug abuse, withdrawal syndrome, muscle spasms, convulsive seizures, epilepsy and other prophylactic and/or therapeutic uses mentioned in WO 00/01895 (for example, to modulate the action of drugs that target the GABA-A receptor),
pain, such as chronic hyperalgesia, inflammatory pain and the other diseases and disorders mentioned in WO 00/01415, U.S. Pat. No. 6,376,467, WO 02/102232, WO 03/089456 and WO 03/089457 and the further prior art listed above,
Cardiovascular disease or heart disease, as mentioned in US 2003/0134774,
Proliferative disease such as cancer,
and also for regulating the immune system and/or regulating an immune response in a mammal, as mentioned in WO 03/04612 and/or regulating an inflammatory response in a mammal.

The compounds of the invention may also be used as an alternative for the peptide inhibitors described in WO 03/089456 and WO 03/089457, e.g. for the same disease indications mentioned in these references for the peptide inhibitors, such as the management of pain. In doing so, the compounds of the invention will have all the usual advantages of small molecules compared to small peptides, for example that they can conveniently be formulated for oral administration, that they are usually easier to manufacture, and that they often are more stable under storage.

Preferably, the compounds and compositions of the invention may be used for preventing and/or treating diabetes, especially Type I and Type II diabetes, obesity and pain, especially preferably diabetes, as well as the complications and/or symptoms associated therewith. "Diabetes" itself refers to a progressive disease of carbohydrate metabolism involving inadequate production or utilization of insulin and is characterized by hyperglycemia and glycosuria.

According to a specific, very preferred, embodiment, the compounds and compositions of the invention are particularly suited for preventing and/or treating Type II diabetes.

In one specific non-limiting embodiment, the present invention relates to the use of the compounds of Formula I or II above in (the preparation of a composition for) the prevention and/or treatment of metabolic diseases such as diabetes and obesity.

In another specific non-limiting embodiment, the present invention relates to the use of the compounds of Formula I or II above in (the preparation of a composition for) the prevention, treatment and/or management of pain, including but not limited to chronic hyperalgesia, generalized pain (e.g., fibromyalgia), inflammatory pain, and/or neuropathic pain.

In another specific non-limiting embodiment, the present invention relates to the use of the compounds of Formula I or II above in (the preparation of a composition for) the prevention, treatment and/or management of coronary heart disease, heart attack, cerebral vasospasm, stroke, kidney failure, kidney diseases or disorders, peripheral vasospasm, diabetic nephropathy, diabetic complications.

In another specific non-limiting embodiment, the present invention relates to the use of the compounds of Formula I or II above in (the preparation of a composition for) the prevention, treatment and/or management of diseases or disorders due to oxygen deprivation such as heart attack, stroke, kidney failure and the like.

In another specific non-limiting embodiment, the present invention relates to the use of the compounds of Formula I or II above in (the preparation of a composition for) the prevention, treatment and/or management of cardiovascular complications due to diabetes, high blood pressure, hypercholesterolemia, kidney failure and the like.

In another specific non-limiting embodiment, the present invention relates to the use of the compounds of Formula I or II above in (the preparation of a composition for) the prevention, treatment and/or management of transplant rejection (acute and chronic) as well as transplant dysfunction.

In another particular embodiment, the compounds of the invention may be used for the inhibition of PKC epsilon and PKC theta in vitro or in vivo, preferably in vitro, and also for modulating biological pathways and/or processes in which such kinases are involved, and/or to prevent and/or treat diseases or disorders in which such kinases, pathways and/or processes are involved.

In another specific non-limiting embodiment, the present invention relates to the use of the compounds of Formula I or II above in (the preparation of a composition for) the prevention, treatment and/or management of inflammatory diseases and auto-immune diseases such as contact dermatitis, psoriasis, rheumatoid arthritis, inflammatory bowel disease, Crohn's disease, ulcerative colitis, allergy and autoimmune diseases or disorders, AIDS and/or multiple sclerosis.

In another particular embodiment, the compounds of the invention may be used for the inhibition of ROCK in vitro or in vivo, preferably in vitro, and also for modulating biological pathways and/or processes in which such kinases are involved, and/or to prevent and/or treat diseases or disorders in which such kinases, pathways and/or processes are involved.

According to one preferred, but non-limiting embodiment, the compounds of the invention may be used to inhibit (at least one isoform of) ROCK, and as such may be used for any purposes known per se for inhibitors of ROCK.

In the invention, particular preference is given to compounds of Formula I or II above that in the inhibition assay for ROCK described below inhibit ROCK with an $IC_{50}$ value of less than 100 µM, preferably less than 50 µM, more preferably less than 10 µM, preferably less than 5 µM, even more preferably less than 1 µM, preferably less than 0.1 µM, and in particular less than 10 nM, for example less than or 1 nM, as determined by a suitable assay, such as the assay used in the Examples below.

The present invention also relates to the use of the compounds of Formula I or II above in (the preparation of a composition for) inhibiting at least one kinase, in particular for inhibiting at least one isoform of ROCK, more in particular for inhibiting ROCK I and/or ROCK II isoforms. As used herein, the term "ROCKI" can also be referred as ROK-β, p160ROCK, or Rho-kinase β and the term "ROCKII" can also be referred as ROK-α or Rho-kinase α. Said inhibition may be effected in vitro and/or in vivo, and when effected in vivo, is preferably effected in a selective manner, as defined above.

According to an embodiment, the invention provides a method for treating or lessening the severity of a ROCK-mediated disease or condition in a patient comprising the step of administering to said patient a compound according to the present invention.

The term "ROCK-mediated condition" or "disease", as used herein, means any disease or other deleterious condition in which is known to play a role. The term "ROCK-mediated condition" or "disease" also means those diseases or conditions that are alleviated by treatment with a ROCK inhibitor. Accordingly, another embodiment of the present invention relates to treating or lessening the severity of one or more diseases in which ROCK is known to play a role.

According to particularly preferred embodiments, the compounds of the invention are preferably used in the prevention and/or treatment of at least one disease or disorder, preferably in which at least one isoform of ROCK is involved. According to an even more particularly preferred embodiment, the compounds of the invention may be used in the prevention and/or treatment of at least one disease or disorder in which the ROCK I or ROCK II is involved, such as inflammatory diseases, chronic obstructive bladder disease (COBD) and the related erectile dysfunction (ED) as well as in diabetes related ED.

Specifically, the present invention relates to the use of a compound according to the invention for the preparation of a medicament for treating or lessening the severity of a disease or condition selected from eye disease or disorder (such as but not limited to retinopathy, glaucoma and degenerative retinal diseases such as macular degeneration and retinitis pigmentosa), kidney disease (such as but not limited to renal dysfunction), erectile and bladder dysfunction, neurological and CNS (brain) disease or disorder (such as but not limited to Alzheimer, meningitis and convulsions), hypertension, lung disease (such as but not limited to asthma, fibrosis, pneumonia, cystic fibrosis and respiratory distress syndrome), premature birth, cancer (such as but not limited to cancer of the lung, intestine, nerve, skin, pancreas, liver, uterus, ovary, brain, thyroid gland, and leukemia, lymphoma and melanoma), cardiovascular and vascular (blood vessel artery) disease or disorder (such as but not limited to cerebrovascular contraction, ischemia, reperfusion, hypoxia peripheral circulation disorder, atherosclerosis, thrombosis, aneurism and hemorrhage), blood disease (such as but not limited to sepsis, eosinophils and endotoxemia), musculoskeletal disease (such as but not limited to spasm), inflammatory disease, infection, allergy and autoimmune diseases or disorders, AIDS, bone disease (such as but not limited to osteoporosis), inflammatory diseases, diabetes (such as but not limited to hyperglycemia), obesity and pancreas disease.

For example, the compounds of the invention may be used in the prevention and/or treatment of diseases and disorders such as:

Cardiovascular and vascular diseases: including but not limited to acute stroke, congestive heart failure, cardiovascular ischemia, heart disease, cardiac remodeling, angina, coronary vasospasm, cerebral vasospasm, pulmonary vasoconstriction, restenosis, hypertension, (pulmonary) hypertension, arteriosclerosis, thrombosis (including deep thrombosis) and platelet related diseases.

Neurological and CNS disorders: including but not limited to stroke, multiple sclerosis, brain or spinal cord injury, inflammatory and demyelinating diseases such as Alzheimers disease, MS and neuropathic pain. The present compounds are therefore suitable for preventing neurodegeneration and stimulating neurogenesis in various neurological disorders.

Proliferative diseases: such as cancer including but not limited to cancer of the central or peripheral nervous system, breast, colon, intestine, skin, head and neck, kidney, lung, liver, ovarian, pancreatic, prostate, or thyroid, leukemia, lymphoma, sarcoma, and melanoma.

Inflammatory diseases: including but not limited to contact dermatitis, psoriasis, rheumatoid arthritis, inflammatory bowel disease, Crohn's disease or ulcerative colitis.

In addition, the compounds of the invention may be used in the prevention and/or treatment of diseases and disorders such as erectile dysfunction, bronchial asthma, osteoporosis, eye diseases such as glaucoma, macular degeneration and retinopathy, renal diseases and AIDS.

The present invention therefore relates to a method of treating or lessening the severity of a disease or condition selected from cardiovascular and vascular diseases including but not limited to angina, coronary vasospasm, cerebral vasospasm, pulmonary vasoconstriction, restenosis, hypertension, (pulmonary), arteriosclerosis, thrombosis (including deep thrombosis), platelet related diseases, acute stroke, congestive heart failure, cardiovascular ischemia, heart disease, and cardiac remodeling; neurological and CNS disorders including but not limited to stroke, multiple sclerosis, brain or spinal cord injury; inflammatory and demyelinating diseases such as Alzheimer's disease, MS and neuropathic pain; proliferative diseases such as cancer including but not limited to central or peripheral nervous system, breast, colon, head and neck, kidney, lung, liver, melanoma, ovarian, pancreatic, prostate, sarcoma, or thyroid cancer; erectile dysfunction; bronchial asthma; osteoporosis; eye diseases such as glaucoma, macular degeneration and retinopathy; renal diseases; AIDS; hypertension; preterm labor; vascular smooth muscle cell proliferation; myocardial hypertrophy; malignoma; ischemia/reperfusion-induced injury; endothelial dysfunction; Crohn's Disease and colitis neurite outgrowth; Raynaud's Disease; benign prostatic hyperplasia; and atherosclerosis; wherein said method comprises administering to a patient in need thereof a compound or a composition according to the present invention.

Formulations

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person, reference is for instance made to the salts, hydrates, solvates, etc described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl hahdes, such as methyl, ethyl, propyl, and butyl chloride, bromides and iodides, dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person, reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desmtegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers in order to enhance the solubility and/or the stability of the compounds of a pharmaceutical composition according to the invention, it can be advantageous to employ α-, β- or γ-cyclodextrins or their derivatives. In addition, co-solvents such as alcohols may improve the solubility and/or the stability of the compounds. In the preparation of aqueous compositions, addition of salts of the compounds of the invention can be more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with alkyl, particularly methyl, ethyl or isopropyl, e.g. randomly methylated β-CD, hydroxyalkyl, particularly hydroxyethyl, hydroxypropyl or hydroxybutyl, carboxyalkyl, particularly carboxymethyl or carboxyethyl, alkylcarbonyl, particularly acetyl, alkoxycarbonylalkyl or carboxyalkoxyalkyl, particularly carboxymethoxypropyl or carboxyethoxypropyl, alkylcarbonyloxyalkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxypropyl-γ-CD and (2-carboxymethoxy)propyl-β-CD, and in particular 2-hydroxypropyl-β-CD (2-HP-β-CD). The term mixed ether denotes cyclodextrin derivatives wherein at least two cyclodextrin hydroxy groups are etherified with different groups such as, for example, hydroxypropyl and hydroxyethyl. An interesting way of formulating the compounds in combination with a cyclodextrin or a derivative thereof has been described in EP-A-721,331. Although the formulations described therein are with antifungal active ingredients, they are equally interesting for formulating the compounds. Said formulations may also be rendered more palatable by adding pharmaceutically acceptable sweeteners and/or flavors. In particular, the present invention encompasses a pharmaceutical composition comprising an effective amount of a compound according to the invention with a pharmaceutically acceptable cyclodextrin. The present invention also encompasses cyclodextrin complexes consisting of a compound according to the invention and a cyclodextrin.

Particular reference is made to the compositions, formulations (and carriers, excipients, diluents, etc for use therein), routes of administration etc., which are known per se for analogous pyridinocarboxamides, such as those described in U.S. Pat. No. 4,997,834 and EP 0370498. For the treatment of pain, the compounds of the invention may be used locally or systemically, e.g. as described for the peptide inhibitors of PKC in WO 03/089456 and WO 03/089457. For local administration, the compounds may advantageously be used in the form of a spray, ointment or transdermal patch or another suitable form for topical, transdermal and/or intradermal administration, and for systemic administration, the compounds of the invention may advantageously be administered orally.

For ophthalmic application, solutions, gels, tablets and the like are often prepared using a physiological saline solution, gel or excipient as a major vehicle. Ophthalmic formulations are preferably prepared at a comfortable pH with an appropriate buffer system.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered. The term "a solid dispersion" also comprises dispersions that are less homogenous throughout than solid solutions. Such dispersions are not chemically and physically uniform throughout or comprise more than one phase.

The water-soluble polymer is conveniently a polymer that has an apparent viscosity of 1 to 100 mPa·s when dissolved in a 2% aqueous solution at 200° C. solution. Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Said beads comprise (a) a central, rounded or spherical core, (b) a coating film of a hydrophilic polymer and an antiretroviral agent and (c) a seal-coating polymer layer. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing the at least one compound according to the invention with the one or more pharmaceutically acceptable earners, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences. The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled), optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, ocular, rectal, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of the Formula I or II above that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

Thus, in a further aspect, the invention relates to a composition, and in particular a composition for pharmaceutical use, that contains at least one compound of the invention and at least one suitable carrier (i.e. a carrier suitable for pharmaceutical use). The invention also relates to the use of a compound of the invention in the preparation of such a composition.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arable, magnesia, magnesium carbonate, potassium phosphate, lactose, glucose, or starch, in particular, corn starch in this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous or intravenous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug. The compositions are of value in the veterinary field, which for the purposes herein not only includes the prevention and/or treatment of diseases in animals, but also—for economically important animals such as cattle, pigs, sheep, chicken, fish, etc—enhancing the growth and/or weight of the animal and/or the amount and/or the quality of the meat or other products obtained from the animal. Thus, in a further aspect, the invention relates to a composition for veterinary use that contains at least one compound of the invention (e.g. a compound that has been identified, discovered and/or developed using a nematode or method as described herein) and at least one suitable carrier (i.e. a carrier suitable for veterinary use). The invention also relates to the use of a compound of the invention in the preparation of such a composition.

Biological Assays

The compounds of the invention can be assessed using the protocols disclosed below.

Primary PKCε Phosphotransferase Assay

The assay mixture can contain 2 ng FLAG-tagged human PKCε expressed and purified from COS-7 cells in 25 μl kinase buffer containing 20 mM Tris-HCl, pH 7.4, 0.25 mM EGTA, 0.1 mg/ml BSA, 0.72% TritonX-100, 10 mM $MgCl_2$, 0.48 μg/μl L-α-phosphatidylserine (PS) and 0.107 μg/μl sn-1, 2-dioleoylglecerol (DG) (Avanti Polar Lipids, Alabaster, Ala., USA), 2 μM K(Biotin)-RFARKGSLRQKNV, 2.5 μM ATP and 0.05 μCi [$^{32}$γ-P]ATP. After incubation at 27° C. for 90 min, the reaction is terminated by adding 12.5 μl of 7.5 M of guanidine hydrochloride. Eight microliters of reaction mixture is spotted onto a pre-cut streptavidin-coated SAM Biotin Capture membrane. The membrane can then be washed once with 2 M NaCl for 30 sec, three times with 2 M NaCl for 2 min each wash, four times with 2 M NaCl in 1% $H_3PO_4$ for 2 min each wash, and twice with double distilled $H_2O$ for 30 sec each time. The membrane is then air dried at room temperature for 60 min and radioactivity remaining on the membrane can be measured by liquid scintillation counting. Specific PKCε activity can then be calculated as the difference between cpms detected in the presence and absence of lipids (PS and DG). Maximal PKCε activity (positive control) can be detected in reactions lacking an inhibitor. Complete inhibition (negative control) can be measured in the presence of the general PKC inhibitor 5 μM bisindolylmaleimide I. The normalized percent inhibition (NPI) can be calculated at each concentration of inhibitor by the formula:

$$NPI = \frac{c_+ - x_i}{c_+ - c_-}$$

where $x_i$ is the raw measurement at the $i^{th}$ concentration of inhibitor, and c+ and c− are the means of the positive and negative controls, respectively.

$IC_{50}$ values can be calculated from normalized dose-response curves by nonlinear regression analysis.

Counter-Screening Assays for Selectivity

Compound selectivity for inhibiting PKCε and not other PKC isozymes or ROCK1 can be determined according to the following assay. Specificity counter screens can be performed against one member of each subclass of PKCs (conventional, novel and atypical).

For example, to measure inhibition of conventional PKCγ, novel PKCδ, and atypical PKCζ, the same kinase assay disclosed above for PKCε can be used with recombinant human PKCγ, PKCδ, or PKCζ purchased from Invitrogen (Carlsbad, Calif., USA) in place of PKCε, with 0.4 mM $CaCl_2$ assay buffer for PKCγ. For atypical PKCζ the zeta inhibitor peptide (Tocris, Ellisville, Mo., USA; sequence=SIYRRGARRWRKL), which selectively inhibits atypical PKC isozymes can be used as a positive control instead of bisindoylylmaleimide I.

Biochemical PKC Theta Assays

Inhibition of PKC theta activity can be measured using the same primary phosphotransferase assay for PKCε except one substitutes recombinant human PKC theta purchased from Invitrogen for PKCε. PKC theta can also be assayed with a fluorescence polarization (FP) assay using the commercially available Protein Kinase C Assay Kit, Red, from Invitrogen (Product ID No P2941), essentially in accordance with the protocol supplied by the manufacturer. The substrate used is RFARKGSLRQKNV ($M_W$ 1561), which can be obtained from Invitrogen (Product ID No P2760). The isozyme PKC theta can be obtained from Invitrogen (Product ID No P2996).

In summary, compounds of the invention can be screened in the wells of a 384 well plate for inhibition of each of the isozymes with concentrations varying from 100 µM to 2 pM using a stepwise 2 (or 3)-fold dilution. Staurosporine can be used as a positive control (2 µM).

To perform the assay, 2 µl of a solution of the compound to be tested in DMSO (at each concentration) is added to 6 µl of a solution of the enzyme in 10 mM HEPES, 5 mM dithiotreitol, 0.1% Triton X-100, pH 7.4. The final concentration of the enzymes will be 60 ng/ml.

After incubating for 30 minutes at room temperature, 4 µl of a mixture of ATP and the protein substrate in 60 mM HEPES (pH7 4), 15 mM $MgCl_2$, 0.3 mM $CaCl_2$, 0.06% NP40 is added. The final concentration of the ATP will be 2.5 µM and the final concentration of protein substrate will be 1 µM.

After incubating for 80 minutes at room temperature, 3 µl of a mix solution of 500 mM EDTA (stop solution) and the Rhodamine-based PKC Red Tracer (from the Protein Kinase C Assay Kit) in BGG/phosphate buffer (pH7.4) with 0.02% $NaN_3$ and 0.1% Triton X-100 and 5 µl of the Anti-Phosphosenne antibody (also from the Protein Kinase C Assay Kit) in BGG/phosphate buffer (pH7.4) with 0.02% $NaN_3$ is added.

The mixture thus obtained (total volume 20l) is incubated for 60 minutes at room temperature, upon which the fluorescence polarization is measured using an automated plate reader (Perkin Elmer, Model Envision 2100-0010 HTS) with FP filters for rhodamine: excitation filter FITC FP 531 and emission filters FITC FP P-pol 595 and FITC FP S-pol 595 (Perkm-Elmer). The results are fitted to a curve using the XL-Fit algorithm and $IC_{50}$ values are calculated for each fitted curve, again using the XL-Fit algorithm.

Any PKC can be assayed in the manners disclosed above. In some cases it is beneficial to use both the fluorescence polarization (FP) assay and the phosphotransferase assay to avoid false positives.

Biochemical Assays for ROCK

The compounds can be tested for inhibition of a human ROCK1/ROCK2 mix according to the following protocol. The inhibition assay is performed with a fluorescence polarization (FP) assay using the commercially available ROCK IMAP Kit from Molecular Devices (Product ID No R8093), essentially in accordance with the protocol supplied by the manufacturer. The S6 ribosomal protein-derived substrate used is (Fl)-AKRRRLSSLRA, which also can be obtained from Molecular Devices (Product ID No R7184). The enzyme mix ROCK1/ROCK2 can be obtained from Upstate Biotechnology (Product ID No 14-451).

In summary, the compound is screened in the wells of a 384 well plate for enzymatic inhibition with concentrations varying from 100 µM to 0.3 nM using a stepwise 3 (or 2)-fold dilution.

To perform the assay, 1 µl of a solution of the compound to be tested in DMSO (at each concentration) is added to 2 µl of a solution of the enzyme in 10 mM Tris-HCl, 10 mM $MgCl_2$, 0.1% BSA, 0.05% $NaN_3$, pH 7.2 The final concentration of the enzyme will be 2.6 nM.

After incubating for 30 minutes at room temperature, 2 µl of a mixture of ATP and the protein substrate in 10 mM Tris-HCl, 10 mM $MgCl_2$, 0.1% BSA, 0 05% $NaN_3$, pH 7.2 is added. The final concentration of the ATP is 10 µM and the final concentration of protein substrate is 0.2 µM. After incubating for 60 minutes at room temperature, 12 µl of the IMAP Binding Solution (mix of the IMAP Binding Buffer A (1×) and the IMAP Binding Reagent (from the ROCK IMAP kit)) is added.

The mixture thus obtained (total volume 17 µl) is incubated for 60 minutes at room temperature, upon which the fluorescence polarization is measured using an automated plate reader (Perkin Elmer, Model Envision 2100-0010 HTS) with FP filters excitation: filter FITC FP 480 and emission filters FITC FP P-pol 535 and FITC FP S-pol 535 (Perkm-Elmer). The results can then be fitted to a curve using the XL-Fit algorithm and $IC_{50}$ values are calculated for each fitted curve, again using the XL-Fit algorithm.

Inhibition of ROCK can also be measured using a phosphotransferase assay developed by Cell Signaling Technology (Danvers, Mass.; Product #7532). Compounds can be incubated with 50 ng of recombinant ROCK1 kinase in 25 ml of a kinase buffer containing 5 mM MOPS, pH 7.2, 2.5 mM β-glycerophosphate, 1 mM EGTA, 4 mM $MgCl_2$, 0.05 mM DTT, 10 µg S6K substrate peptide (SignalChem, Richmond, BC, Canada: sequence=KRRRLASLR), 2.5 µM ATP and 0.8 µCi [32γ-P]ATP. After 10 min of preincubation with each test compound, the reaction can be started by adding ATP. After 15 min of incubation at 27° C., the reaction can be terminated by adding 5 µl of 3% phosphoric acid. Ten microliters of reaction mixture can be spotted onto a P30 filter mat. The membrane can be washed three times with 75 mM phosphoric acid for 5 min, and once with methanol for 5 min, and then air dried at 27° C. for 60 min. Radioactivity remaining on the membrane can be measured by liquid scintillation counting. ROCK1 kinase activity can be calculated as the difference in activity measured in the absence and in the presence of the ROCK inhibitor Y-27632 (10 µM).

Cell Models for Inhibitors of PKCε
Cellular Models are Used to Evaluate Potential for In Vivo Potency of PKCε Inhibitors
Cell-Based Assay for PKCε Modulation of GABA$_A$ Receptors PKCε inhibition can also be measured by assaying benzodiazepine modulation of GABA$_A$ receptors in intact cells. PKCε decreases benzodiazepine potency at GABA$_A$ receptors by phosphorylating S327 of GABA$_A$ γ2 subunits. The GABA$_A$ cell-based assay uses a HEK293 cell line that expresses α1β2γ2 GABA$_A$ receptors and over-expresses PKCε. The well-characterized benzodiazepine flunitrazepam increases 3 μM GABA-stimulated currents in HEK cells expressing these receptors with an EC$_{50}$ of 150 nM, and complete inhibition of PKCs decreases the EC$_{50}$ to 25 nM. This 6-fold difference in benzodiazepine potency can be detected without addition of a PKC activator. The assay is performed using an anti-phospho antibody that recognizes γ2S(P)327 in an ELISA format to generate 8 point dose-response curves for each compound. Background values, detected from wells in which no primary antibody was added, are subtracted from sample values. Maximal phosphorylation (positive control) is detected in reactions containing phorbol ester and lacking an inhibitor. Complete inhibition (negative control) is measured in the presence of 10 μM bisindolylmaleimide I. A dose-response curve for Compound 1,

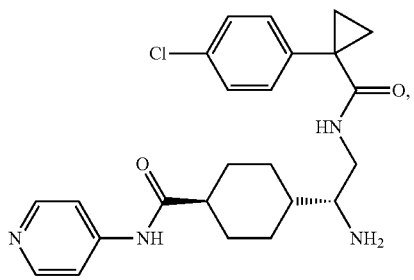

demonstrated that it acts as an inhibitor in this assay with an IC$_{50}$ of 8.9 nM (log IC$_{50}$=−8.05±0.14 M).

Cell Based Elk-1 Reporter Assay for PKCε Activity

This reporter assay is focused on PKCε specific inhibition in a recombinant system and assay exploits the effect of over-expressed PKCε on kinase activation and phosphorylation of a transcription factor to evaluate the potency and selectivity of PKCε inhibitors in a cellular context. It has been shown by Jae-Won Soh et al. (MCB, February 1999, p 1313-1324) that over-expression of PKC epsilon results in the activation of MAPK-pathway (c-raf/MEK/ERK) leading to the activation of Elk transcription factor. This event can be monitored using the PathDetect trans reporter assay system (Stratagene). pFA2-ELK codes for a fusion protein between the Gal4 DNA binding domain and the transactivation domain of Elk, which drives the expression of a secreted alkaline phosphatase (SEAP) reporter gene.

Compounds are incubated with reporter cell-lines either over-expressing PKCε, leading to continued activation of the kinase, or mock transfected cells. Inhibition of the PKCε induced signal in the absence of an effect on the basal level (mock transfected cells) is indicative of selective PKCε inhibition.

To position the data, the results are compared with the results obtained with bisindolylmaleimide (BIM I) in this assay. BIM I is the most potent, yet unselective, PKCε inhibitor known in literature.

LPS Induced TNFα Release In Vitro (Bio-Marker Assay)

This is a cellular assay measuring PKCε activity in a physiological context and is based on the observation that LPS induced TNFα release in monocytes/macrophages is dependent on PKCε. The assay can be performed in vitro as well as in vivo. As an example for the in vitro application, the concentration-response curve of compounds of the invention and BIM I on TNFα release can be measured 24 hours after LPS stimulation in whole blood.

Similarly, a cellular assay can be performed, based on the observation that LPS-induced TNFα release in monocytes/macrophages is dependent on ROCK. The assay can be performed in vitro as well as in vivo.

As an example for the in vitro application, the concentration-response curve of compounds of the invention on TNFα release can be measured 24 hours after LPS stimulation in whole blood.

In Vivo Assays
Mechanical Hyperalgesia Assay

Compounds of the invention can be tested for efficacy in reducing PKCε-dependent pain in rats. The efficacy can be measured by performing the Randall-Selitto paw-withdrawal test, using an Ugo Basile Analgesymeter® (Stoelting, Chicago, Ill.) (11, 12). This device generates a mechanical force that increases linearly with time. The force is applied by a dome-shaped plunger (diameter 1.4 mm, radius of curvature 36°), placed directly over the site of intradermal injection of test agents on the dorsum of the rat's hind paw. The nociceptive threshold is defined as the force, in grams, at which the rat withdraws its paw. Prior to testing the effects of agents on nociceptive threshold, rats can be trained in the paw-withdrawal test at 5 min intervals, for a period of 2 hrs each day for 3 days. This adaptation procedure provides decreased variability and increased sensitivity for detection of interventions that alter the nociceptive threshold. On the days when the effect of intradermal injection of drugs are evaluated, the rats can first be trained for 2 hrs. The average threshold of the last 6 training trials constitutes the baseline nociceptive threshold for that day. Fifteen minutes after the training trials, either εψRACK (1 μg in 2 μl; (11)) or a scrambled control peptide will be injected, followed immediately by the highest dose of test compound (10 μg in 2.5 μl) or its vehicle control, and 15 min later the paw-withdrawal threshold measured 3 times at 5 min intervals. The percentage decrease (or increase) in mechanical paw withdrawal threshold from the pre-injection baseline to each time point post-injection can be used as the measure of the magnitude of the hyperalgesic (or analgesic) effect. Mean values for paw withdrawal threshold can be calculated for each time point and compared by two-way ANOVA with a factor for treatment and a repeated measure for time. Pairs of means can be compared by post-hoc Tukey tests and can be considered significantly different if P<0.05. Once the time to maximal inhibitory effect is determined, a range of doses of the inhibitor (1 ng-10 μg in 1 μl) can be tested using the opposite hindpaw to generate a dose-response curve for inhibition of εψRACK-induced hyperalgesia. This can be evaluated by non-linear regression analysis to generate values for IC$_{50}$, Hill slope and maximal response.

LPS Induced TNFα Release In Vivo (Bio-Marker Assay)

The concept is the same as the in vitro TNFα release assay, but this time the animals receive compound (or vehicle) via oral IP injection before they are challenged with IP injection of LPS. 1 hour after the LPS challenge, a terminal blood sample is taken and the amount of TNFα in the serum is determined using standard ELISA (R&D systems). This assay not only gives information on the appropriate route and dose to obtain efficacy in vivo but it also gives an idea on the duration of action (how long is the compound around at sufficiently high levels to exert an effect on the target) by varying the time between dosing of compound and the LPS challenge.

Carrageenin-Induced Paw Edema

This is an acute model of inflammation useful in the initial in vivo evaluation of anti-inflammatory compounds developed for the treatment of diseases such as rheumatoid arthritis and multiple sclerosis. Injection of carrageenin into the subplantar region of the hind limb results in joint inflammation within hours after induction. The response is in part due to TNFalpha production.

The basic measurement in this model is comparison of paw volume (swelling) between the right, carrageenin treated, and left, untreated hindlimb over a period of 6 hours after the injection with carrageenin. The efficiency of compounds of the invention in acute inflammation are evaluated using the carrageenin model. 5-6 weeks old Swiss Webster mice (Harlan) are weighed and the right paw volume is measured by water displacement at the start of the experiment. The animals (n=10) are administered either vehicle or different doses of compound of the invention by the oral route. Two hours after oral administration, animals are anesthetized and injected with 50 μl (10 mg/ml) carrageenin in the sub plantar region of the paw. Two, four and six hours following the injection, the paw volumes are measured.

Mice are dosed with: vehicle alone, 10 mg/kg and 30 mg/kg of a compound of the invention orally, 2 h before carrageenin injection into the paw. Paw volume is investigated for groups of 10 treated animals (n=10). The two hour value has a significance of >99% according to the T test.

The invention will now be illustrated by means of the following synthetic and biological examples, which do not limited the scope of the invention in any way.

EXAMPLES

Unless otherwise noted, reagents and solvents were used as received from commercial suppliers. Proton Nuclear Magnetic Resonance spectra were obtained on a Bruker ARX 400 spectrometer at 400 MHz. The solvent peak was used as a reference peak for proton spectra. TLCs were run on silica, unless otherwise noted.

Example 1

Synthesis of trans-4-[1-Amino-2-[[[1-(4-chlorophenyl)cyclopropyl]carbonyl]amino]ethyl]-N-4-pyridinyl-cyclohexylcarboxamide (1)

Scheme 1

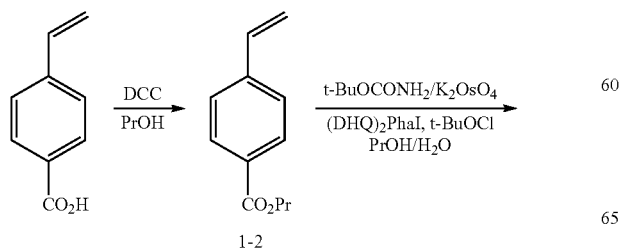

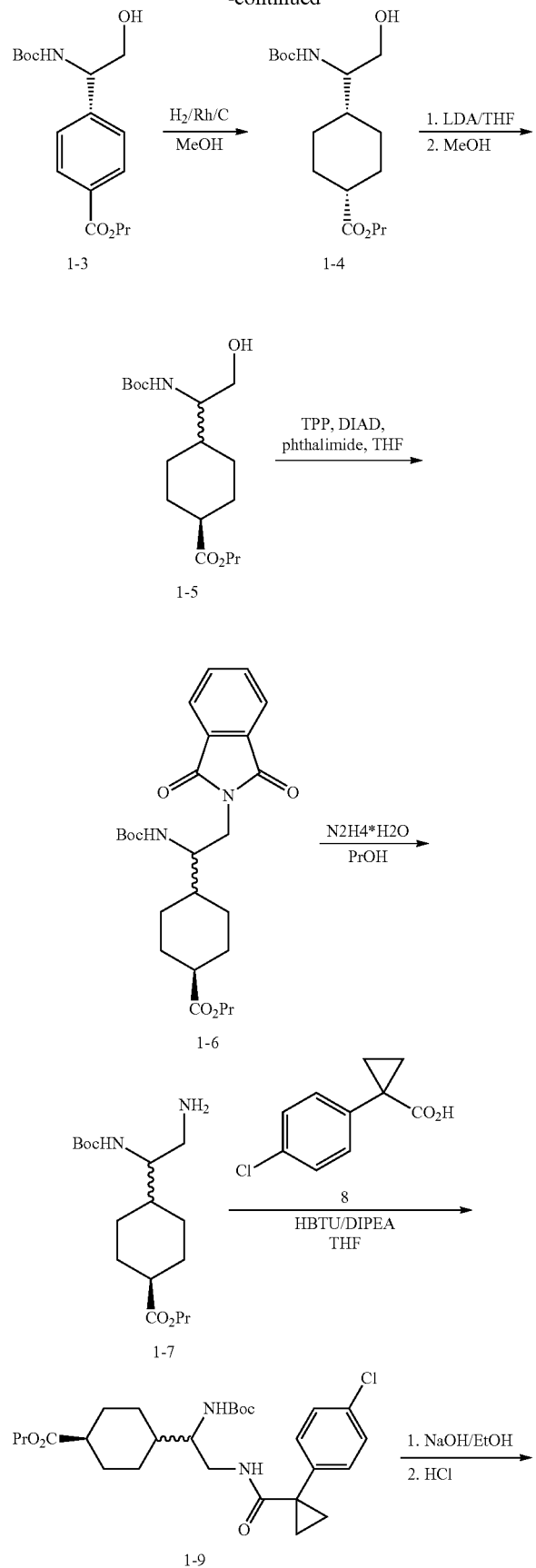

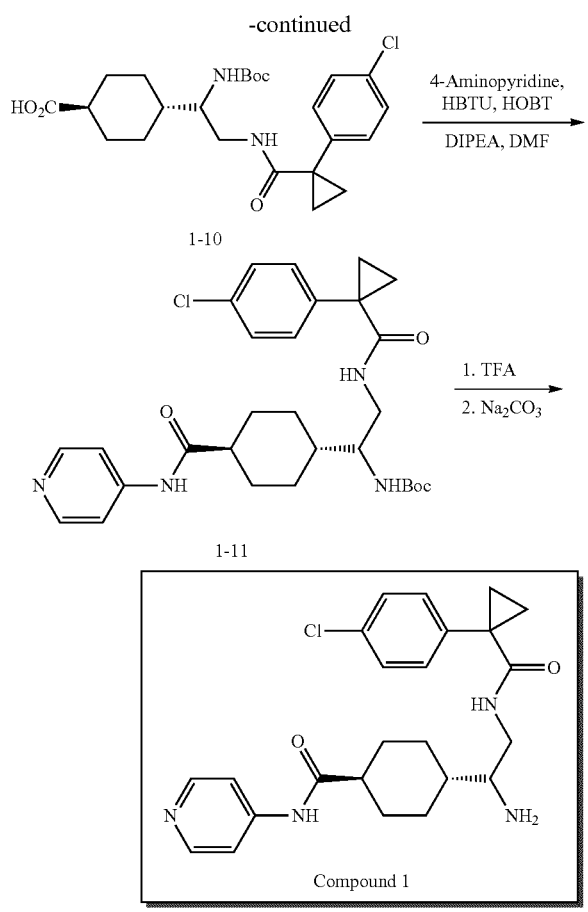

Propyl 4-vinylbenzoate (1-2)

Figure 2:
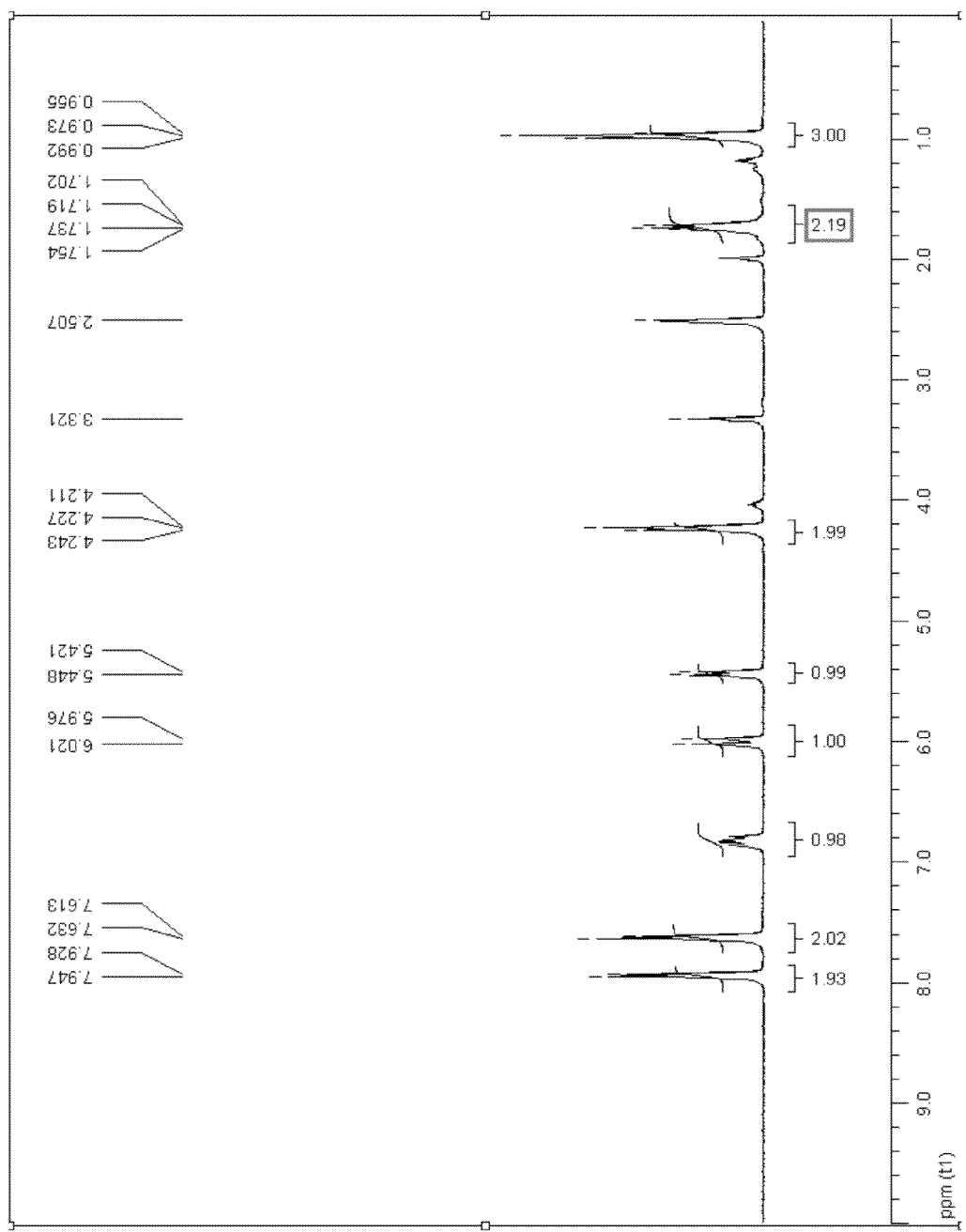
FIGS. 2-9 show $^1$H NMR data with DMSO solvent of the indicated compounds of Example 1.

DCC (MW 206.33, 7.9 g, 0.0383 mol, 1.1 eq) was added to a solution of 4-vinylbenzoic acid (1-1) (MW 148.16, 5.16 g, 0.0348 mol, 1 eq) and 1-propanol (MW 60.1, 5.3 mL, 0.0697 mol, 2 eq) in anhydrous $CH_2Cl_2$ (50 mL) at 0° C. followed by DMAP (MW 122.17 m, 52 mg, 1% wt). The reaction mixture was stirred for 1 hour at 0° C., and then at RT overnight. The solid was filtered off washed with $CH_2Cl_2$ (300 mL) and the filtrate evaporated to dryness. The residue was purified on a silica gel column, eluted with EtOAc/Hexanes to get 5.79 g (87.5%) of pure 1-2. The $^1H$ NMR (DMSO-$d_6$) data is depicted in FIG. 2.

Propyl 4-(1-tert-Butoxycarbonylamino-2-hydroxy-ethyl)-benzoate (1-3)

i. Formation of tert-Butyl hypochlorite

Bleach (250 mL) was added to a 1 L flask fitted with a mechanical stirrer. The solution was cooled with an ice-$H_2O$ bath to <10° C. The flask was covered with tin foil. A solution of t-BuOH (18.5 mL) and AcOH (12.3 mL) was added in a single portion to the rapidly stirred bleach solution. The reaction mixture was stirred for 5 min. The layers were separated. The organic layer was washed with 10% $Na_2CO_3$ (1×30 mL), water (1×30 mL). After drying over $Na_2SO_4$ and filtration, 11.54 g of an oily yellow liquid was obtained.

Figure 3:
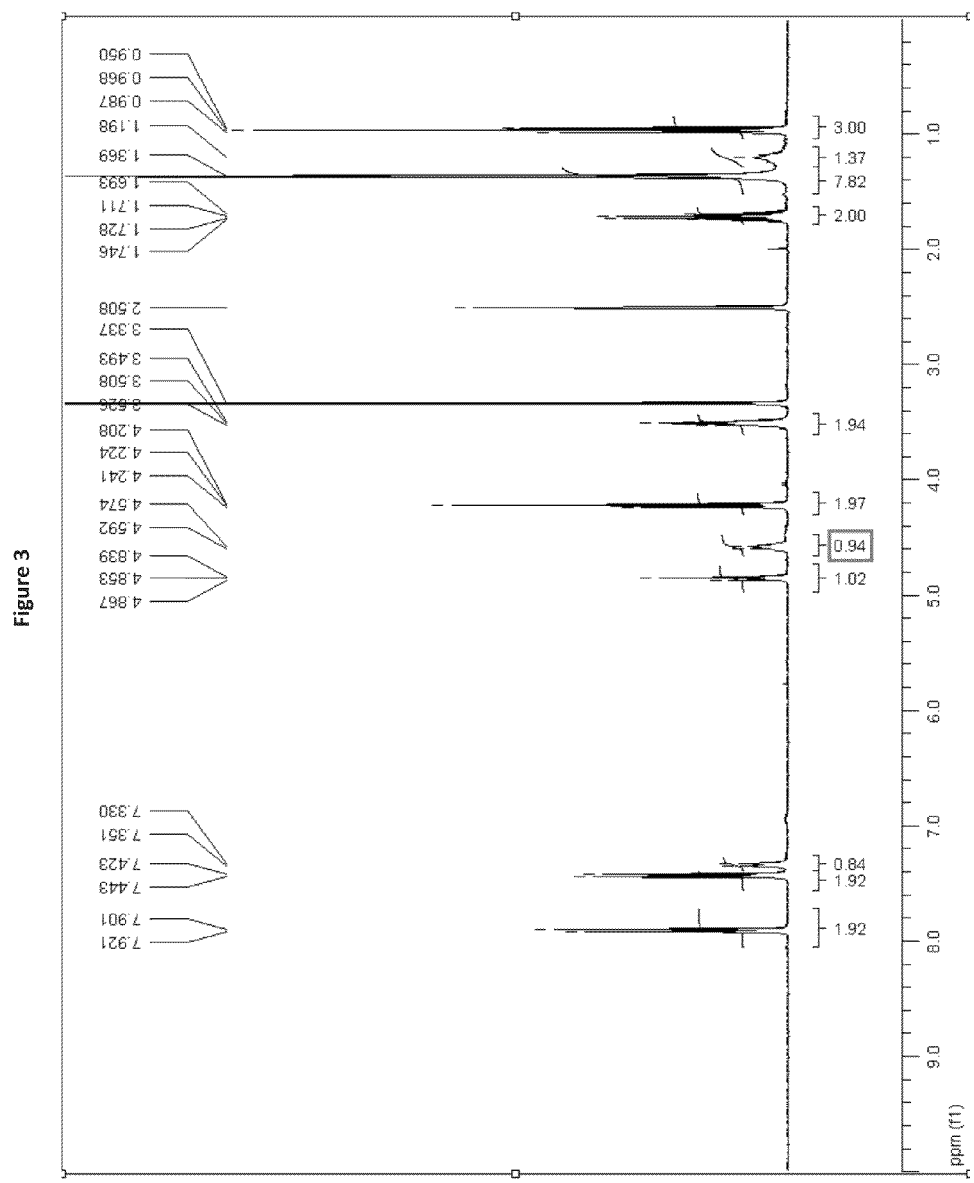

II. Formation of (1-3)

t-Boc-$NH_2$ (MW 108.57, 9.8 g, 0.0837 mol, 2.95 eq) was dissolved in n-PrOH (110 mL) in a 1 L RB flask, The solution was treated with NaOH (MW 40, 3.6 g, 0.9 mol, 3.17 eq) in $H_2O$ (220 mL) and tert-Butyl hypochlorite (MW 108.57, 10 mL, 0.0868 mol, 3.06 eq). After stirring for 20 minutes, the solution was cooled to 0° C. A solution of $(DHQ)_2phal$ (MW 779, 0.43 g, 0.552 mmol, 0.019 eq) in n-PrOH (110 mL) was added. A solution of propyl 4-vinylbenzoate (MW 190.24, 5.41 g, 0.0284 mol, 1 eq) in n-PrOH (220 mL) was then added, followed by the addition of $K_2OsO_4$ (MW 368.43, 427 mg, 0.00116 mol, 0.04 eq). The reaction mixture was stirred at 0° C. and monitored by LC/MS and TLC. After stirring at 0° C. for 2 hours, the reaction was quenched with sat. $Na_2SO_3$ and n-PrOH was removed under vacuum. The residue was diluted with water and extracted with EtOAc (3×). The combined EtOAc fraction was washed with 5% HCl (1×) and brine (1×). After drying over $Na_2SO_4$ and filtration, the filtrate was concentrated under vacuum to dryness. The residue was purified on a silica gel column, eluted with EtOAc/Hexanes (10-40%) to give 5.17 g (56% yield) of the pure 1-3. The $^1H$ NMR (DMSO-$d_6$) data is depicted in FIG. 3.

4-(1-tert-Butoxycarbonylamino-2-hydroxy-ethyl)-cyclohexanecarboxylic acid propyl ester (1-4)

Propyl 4-(1-tert-Butoxycarbonylamino-2-hydroxy-ethyl)-benzoate (3) (5.35 g, 16.5 mmol) was dissolved in MeOH (150 mL). Argon was bubbled for 20 minutes. 5% Rh/C (1 g) was charged to the solution and argon was bubbled for another 10 minutes. The reaction mixture was stirred at 60 psi hydrogen pressure for 16 hours then at 100 psi for 7 days. Another portion of 10% Rh/C 1% Pd/C (1.2 g) was added. The reaction mixture was stirred at 100 psi hydrogen pressure for another 7 days after which LC/MS analysis indicated complete hydrogenation of the aromatic ring. The reaction mixture was filtered through a celite bed and rinsed with MeOH. The filtrate was concentrated under vacuum to dryness. The residue was filtered through a silica gel bed and eluted with EtOAc/Hexanes (20~40%) to give 4.9 g (89.9% yield) of the pure 1-4.

cis-/trons-4-(1-tert-Butoxycarbonylamino-2-hydroxy-ethyl)-cyclohexane-carboxylic acid propyl ester (1-5)

Figure 4:
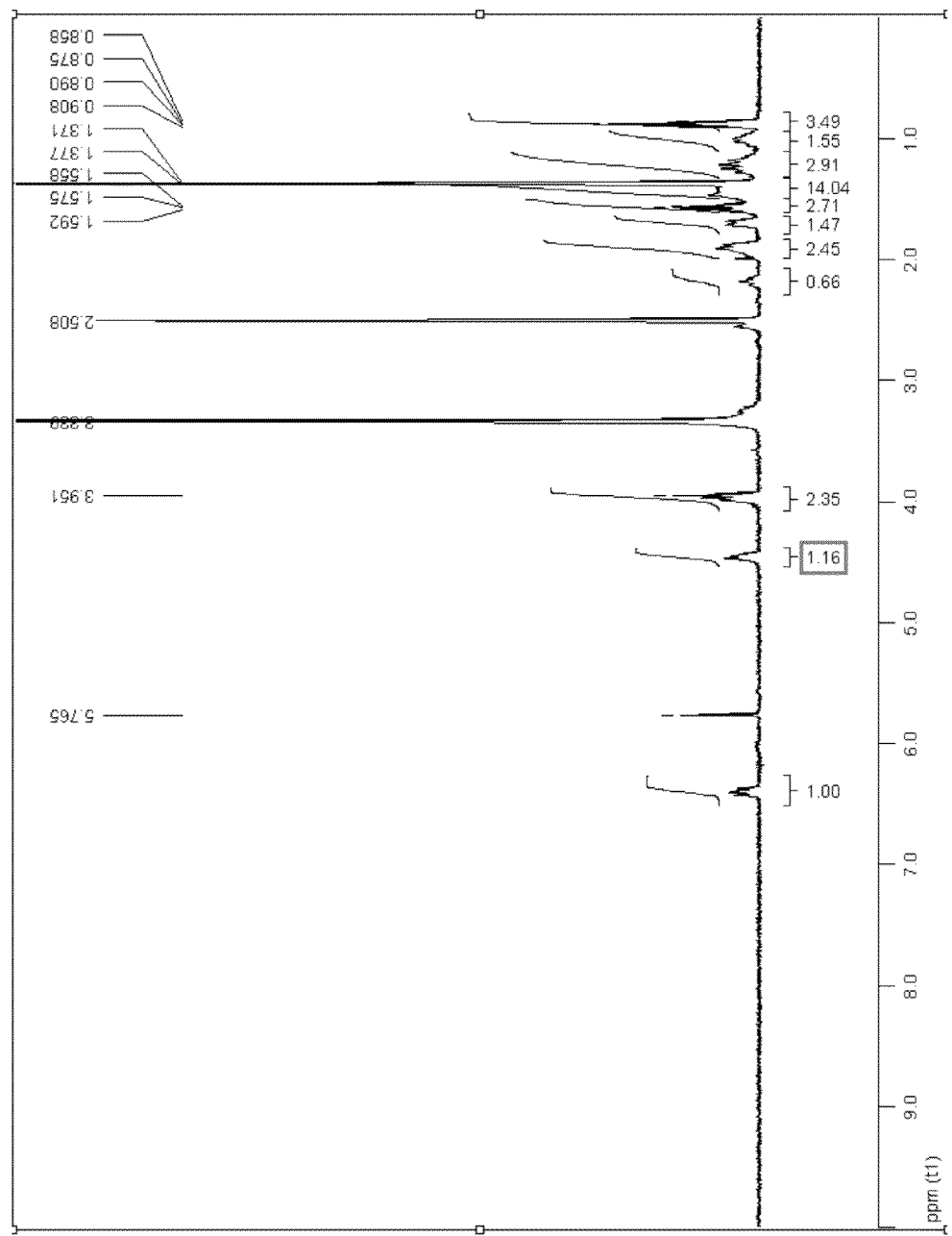

4-(1-tert-Butoxycarbonylamino-2-hydroxy-ethyl)-cyclohexanecarboxylic acid propyl ester (1-4) (4.26 g, 0.0129 mol, 1 eq) was dissolved in anhydrous THF (200 mL) under argon in a 1 L RB flask. The solution was cooled with an acetone-dry ice bath to −78° C. LDA (2.0 M solution) (51.7 mL, 0.103 mol, 8 eq) was added dropwise at −70° C. The reaction mixture was stirred at −70° C. for 2 hours. The reaction was quenched with MeOH (40 mL). The pH was adjusted to pH=45 with 5% HCl. The mixture was extracted with $Et_2O$ (3×330 mL). The combined extracts were washed with brine (1×300 mL). After drying over $Na_2SO_4$ and filtration, the filtrate was concentrated under vacuum to dryness. The residue was purified on a silica gel column eluting with EtOAc/Hexanes 20~40%) to give 3.78 g (88.7% yield) of the intermediate 1-5 as a mixture of cis- and trans-isomers. The $^1H$ NMR (DMSO-$d_6$) data is depicted in FIG. 4.

cis-/trans-4-(2-Amino-1-tert-butoxycarbonylamino-ethyl)-cyclohexane-carboxylic acid propyl ester (1-7)

In a 250 mL RB flask, cis-/trons-4-(1-tert-Butoxycarbonylamino-2-hydroxy-ethyl)-cyclohexanecarboxylic acid propyl ester (5) (1.84 g, 0.0056 mol, 1 eq) was dissolved in anhydrous THF (30 mL) under argon. Phthalimide (0.82 g, 0.0056 mol, 1 eq) was added to this solution followed by PPh$_3$ (2.93 g, 0.011 mol, 2 eq). DIAD (2.28 mL, 0.011 mol, 2 eq) was charged while cooling with a H$_2$O bath. The reaction mixture was stirred at ambient temperature for 3 hours. TLC (30% EtOAc/Hexanes) and LC/MS indicated the absence of the starting material. The reaction was quenched with H$_2$O. The mixture was extracted with EtOAc (3×40 mL). The combined EtOAc extracts were washed with brine (1×40 mL), dried over Na$_2$SO$_4$ and the solvent evaporated to dryness. The crude product was purified on a silica gel column, eluting with EtOAc/Hexanes (1030%) to get 4 g of the intermediate 1-6 containing DIAD-H$_2$ by-product.

Figure 5:
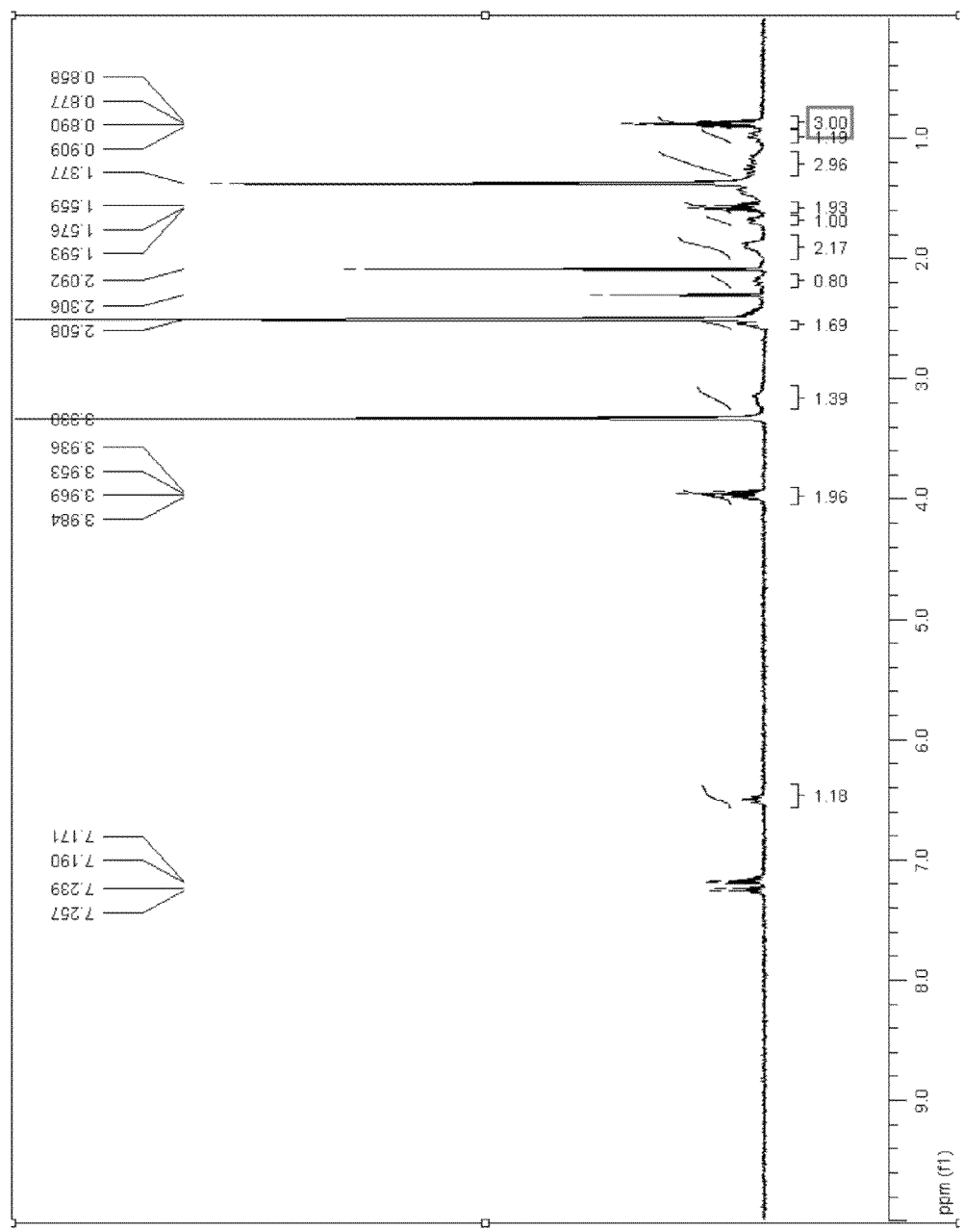

Compound 1-6 (4 g) was dissolved in n-PrOH (60 mL) and THF (10 mL) in a 250 mL RB flask. H$_2$NNH$_2$.H$_2$O (0.33 mL) was added to this solution. The reaction mixture was stirred at 50° C. for 2 hours and at RT overnight. LC/MS indicated the absence of the starting material. The white solid was removed by filtration and rinsed with n-PrOH. The filtrate was diluted with H$_2$O (80 mL). n-PrOH and THF were removed under vacuum. The aqueous layer was extracted with EtOAc (3×200 mL). The combined EtOAc was washed with 5% HCl (1×200 mL). The aqueous layer was basified to pH=89 with 20% NaOH and then extracted with EtOAc (3×200 mL). The combined EtOAc was washed with brine (1×200 mL). After drying over Na$_2$SO$_4$ and filtration, the filtrate was concentrated under vacuum to dryness. The crude product was purified on a silica gel column, eluting with MeOH/CH$_2$Cl$_2$ (5~15% containing 0.1% NH$_3$.H$_2$O) to obtain 0.88 g (47.9% yield) of 1-7. The $^1$H NMR (DMSO-ds) data is depicted in FIG. 5.

cis-/trans-4-(1-tert-Butoxycarbonylamino-2-{[1-(4-chloro-phenyl)cyclo-propanecarbonyl]-amino}-ethyl)-cyclohexanecarboxylic acid propyl ester (1-9)

Figure 6:
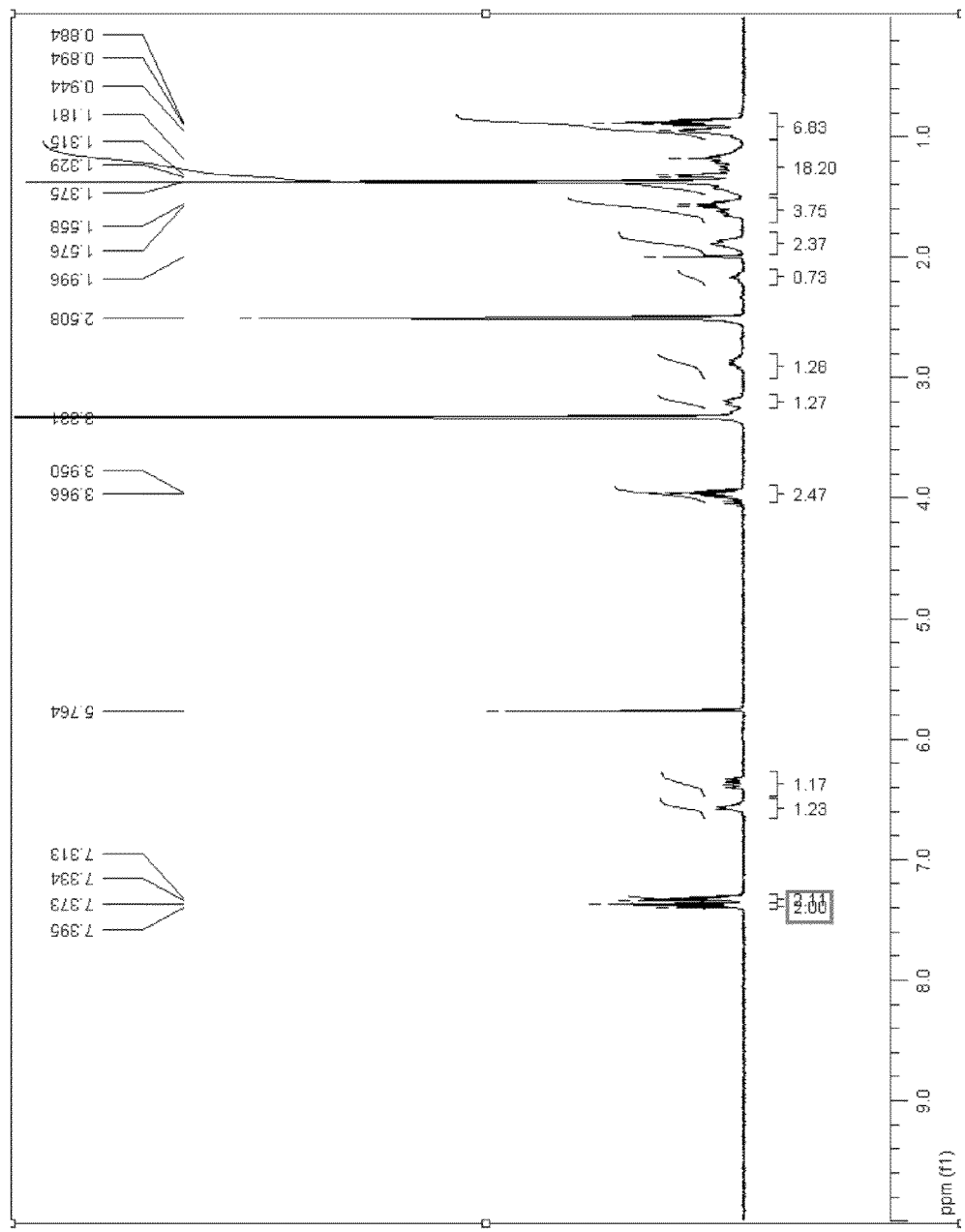
Figure 7:
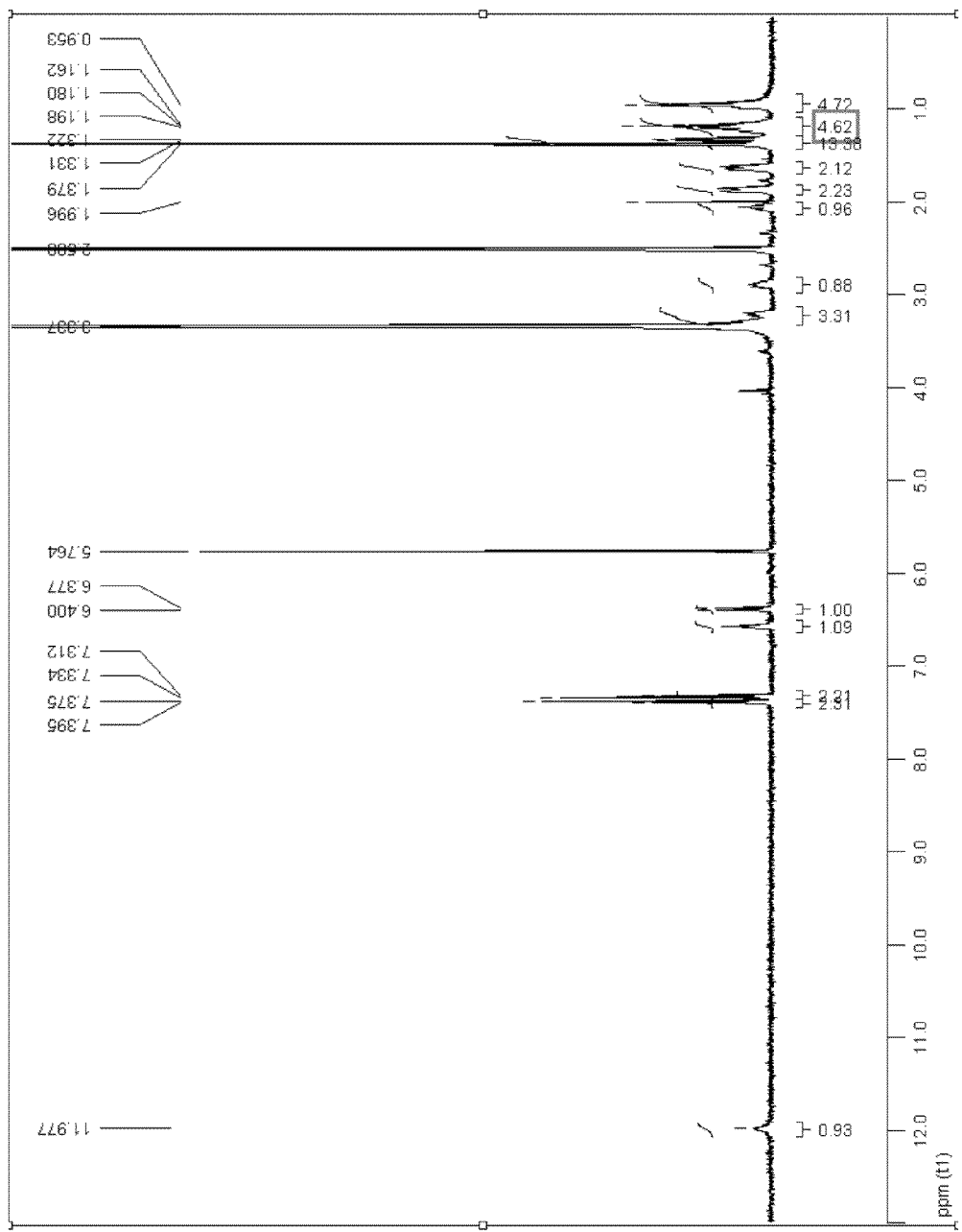

1-(4-Chlorophenyl)cyclopropanecarboxylic acid (527 mg, 2.68 mmol, 1.0 eq) was dissolved in anhydrous DMF (20 mL) in a 250 mL RB flask, under argon. HBTU (1.32 g, 3.48 mmol, 1.3 eq), and DIPEA (0.95 mL, 5.36 mmol, 2.0 eq) were added to this solution. The reaction mixture was stirred at RT for 15 minutes. To this mixture was charged cis-/trans-4-(2-Amino-1-tert-butoxycarbonylamino-ethyl)-cyclohexanecarboxylic acid propyl ester (1-7) (880 mg, 2.68 mmol, 1.0 eq) in anhydrous DMF (20 mL) solution. The reaction mixture was stirred at RT for 2 hours. LC/MS indicated the absence of the starting material. DMF was removed under vacuum. The residue was treated with 1:1 brine/EtOAc (300 mL). The aqueous layer was extracted with EtOAc (2×150 mL). The combined EtOAc extracts were washed with brine (1×150 mL), dried over Na$_2$SO$_4$ and the solvent evaporated to dryness. The crude product was purified on a silica gel column, eluting with EtOAc/Hexanes (20~25%) to give 1.26 g (92% yield) of 1-9. The $^1$H NMR (DMSO-d$_6$) data is depicted in FIG. 6.

trans-4-(1-tert-Butoxycarbonylamino-2-{[1-(4-chloro-phenyl)cyclopropane-carbonyl]-amino}-ethyl)-cyclohexanecarboxylic acid (1-10)

cis-/trans-4-(1-tert-Butoxycarbonylamino-2-{[1-(4-chloro-phenyl)-cyclopropane-carbonyl]-amino}-ethyl)-cyclohexanecarboxylic acid propyl ester (1-9) (1.26 g, 0.00248 mol, 1 eq) was dissolved in THF (20 mL) and MeOH (10 mL) in a 250 mL RB flask LiOH (0.12 g, 0.00497 mol, 2 eq) in H$_2$O (5 mL) was added to this solution. The reaction mixture was stirred at RT for 1 hour. NaOH (MW 40, 0.0075 mol, 3 eq) in H$_2$O (5 mL) was added to the above reaction mixture. The reaction mixture was stirred at RT overnight. The reaction mixture was diluted with H$_2$O. The pH was adjusted to 23 with 5% HCl while cooling with an ice-H$_2$O bath. THF and MeOH were removed under vacuum. The residue was extracted with EtOAc (3×80 mL). The combined EtOAc extracts were washed with brine (1×80 mL), dried over Na$_2$SO$_4$ and solvent evaporated to dryness. The crude product was purified on silica gel column, eluting with MeOH/CH$_2$Cl$_2$ (1.25~10%) to afford 0.28 g plus 0.23 g (less pure) (46% yield) of 1-10. The $^1$H NMR (DMSO-d$_6$) data is depicted in FIG. 7.

Figure 8:
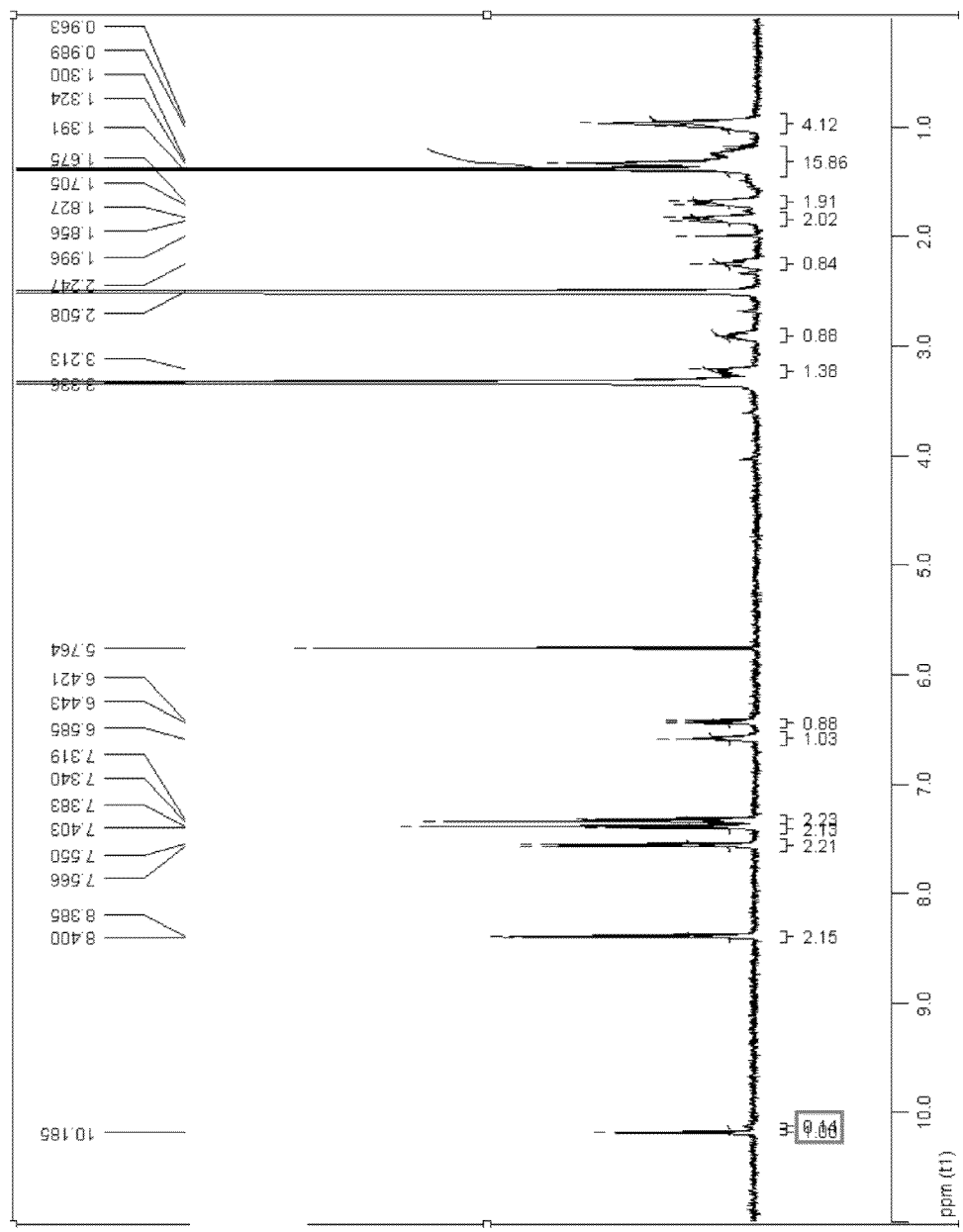

Boc trans-4-[1-Amino-2-[[[1-(4-chlorophenyl)cyclopropyl]carbonyl]amino]ethyl]-N-4-pyridinyl-cyclohexycarboxamide (1-11)

trans-4-(1-tert-Butoxycarbonylamino-2-{[1-(4-chlorophenyl)cyclopropane-carbonyl]-amino}-ethyl)-cyclohexanecarboxylic acid (1-10) (280 mg, 0.602 mmol, 1 eq) was dissolved with anhydrous DMF (6 mL) under argon in a 100 mL RB flask. HBTU (252 mg, 0.664 mmol, 1.1 eq) and DIPEA (0.22 mL, 1.263 mmol, 2 eq) were added. After stirring at RT for 10 minutes, 4-aminopyridine (0.956 mmol, 1.5 eq) was added. The reaction mixture was stirred at RT for 2 hours. TLC (10% MeOH/CH$_2$Cl$_2$) and LC/MS showed no starting material. The reaction mixture was poured into H$_2$O and extracted with EtOAc (3×30 mL). The combined EtOAc extracts were washed with brine (1×30 mL), dried over Na$_2$SO$_4$ and the solvent evaporated to dryness. The crude product was purified on silica gel column, eluted with MeOH/CH$_2$Cl$_2$ (2.5~10%) to give 270 mg (82.9% yield) of the pure 1-11. The $^1$H NMR (DMSO-d$_6$) data is depicted in FIG. 8.

trans-4-[1-Amino-2-[[[1-(4-chlorophenyl)cyclopropyl]carbonyl]amino]ethyl]-N-4-pyridinyl-cyclohexylcarboxamide (1)

Figure 9:
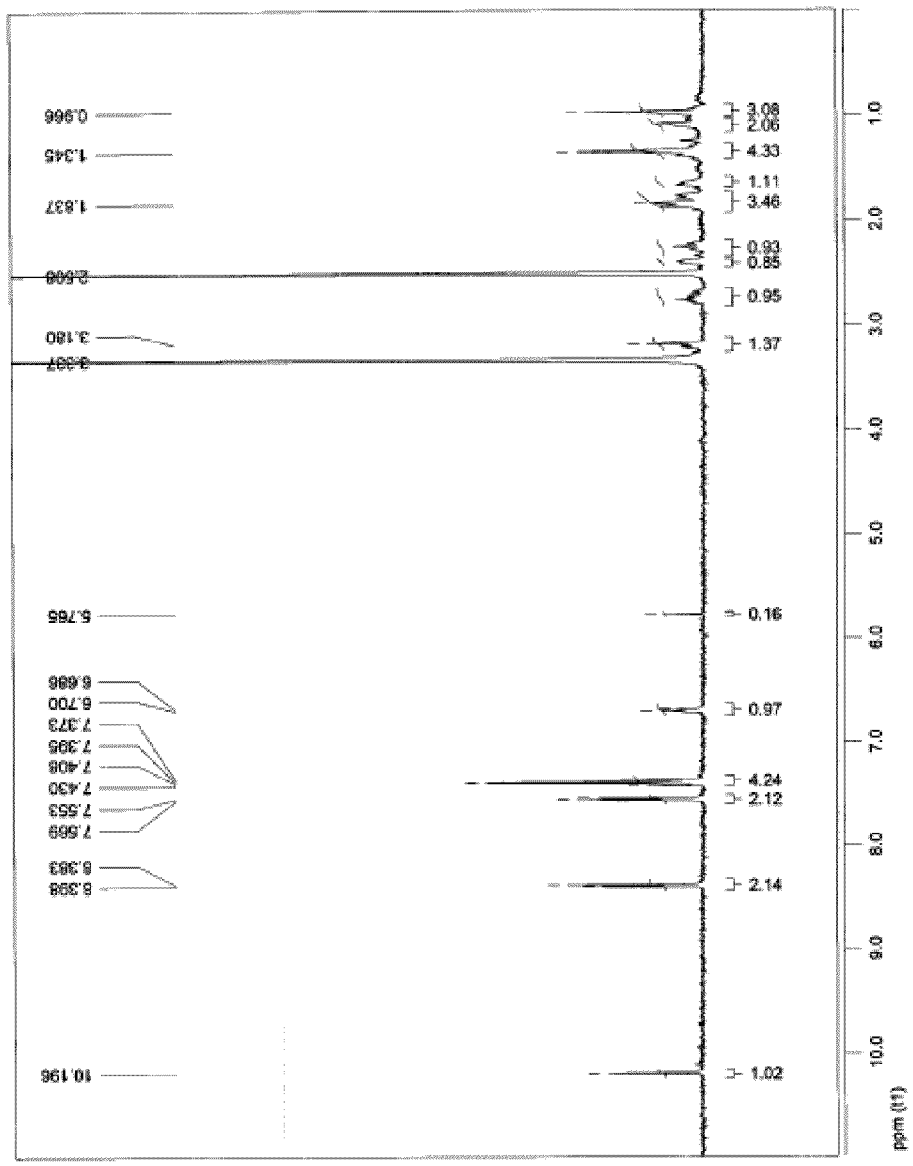

Boc trans-4-[1-Amino-2-[[[1-(4-chlorophenyl)cyclopropyl]carbonyl]amino]ethyl]-N-4-pyridinyl-cyclohexylcarboxamide (1-11) (MW 541.08, 270 mg) was charged to a 250 mL flask. 20% TFA in CH$_2$Cl$_2$ (1 mL of TFA in 4 mL of anhydrous CH$_2$Cl$_2$) solution was added. The reaction mixture was stirred at RT for 60 minutes. TLC (10% MeOH/CH$_2$Cl$_2$) and LC/MS indicated the absence of the starting material. The reaction mixture was diluted with EtOAc and then washed with 20% Na$_2$CO$_3$. The aqueous layer was extracted with EtOAc (2×30 mL). The combined EtOAc extracts were washed with brine, dried over Na$_2$SO$_4$ and solvent evaporated to dryness. The crude product was filtered through a silica gel bed, rinsed with MeOH/CH$_2$Cl$_2$ (5~15% containing 0.1% TEA) to give 170 mg (77.3% yield) of the pure 1.99% pure by HPLC (254 nm); MS (ESI) m/z=441.27[M+H]$^+$ The $^1$H NMR (DMSO-d$_6$) data is depicted in FIG. 9.

The following Compounds 3-9 were synthesized following procedures substantially as described for Compound 1 upon appropriate substitution of starting material.

Compound 3

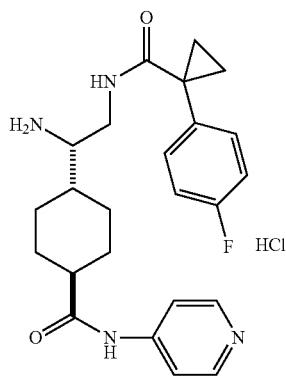 [SMILES: NC(CNC(=O)C1(c2ccc(F)cc2)CC1)[C@H]1CC[C@H](C(=O)Nc2ccncc2)CC1 ; Cl]

Figure 10:
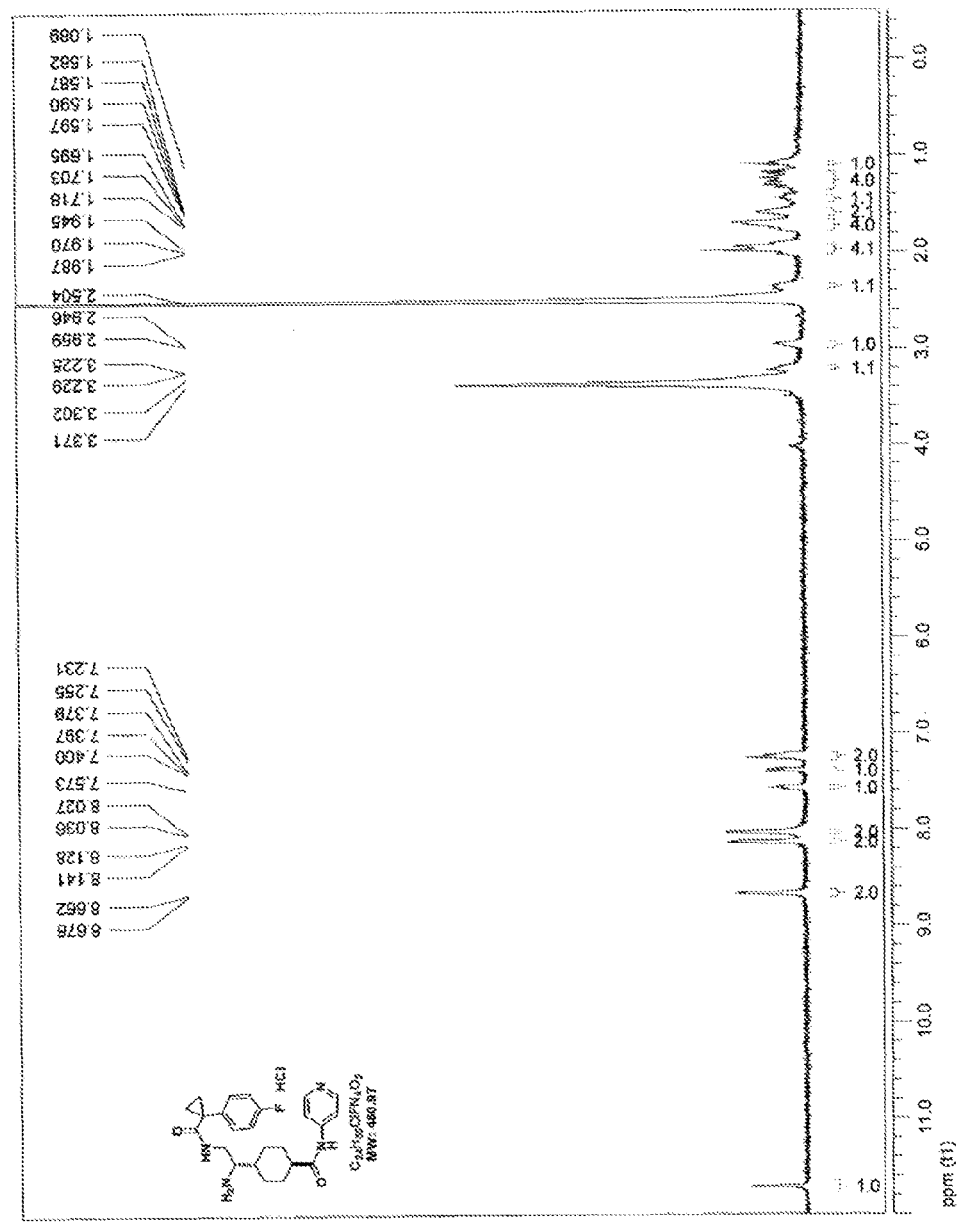
FIGS. 10-16 show $^1$H NMR data of certain other indicated compounds of Example 1.

Molecular formula (M.F.): $C_{24}H_{29}FN_4O_2 \cdot HCl$; molecular weight (M.W.): 460.97 (free base: 424.51); purity: 96.26% by area under curve (AUC) at 254 nm (HPLC); MS (ESI+ve): $[M+H]^+=425.2$ (free base). For $^1H$ NMR DMSO-$d_6$, see FIG. 10.

Compound 4

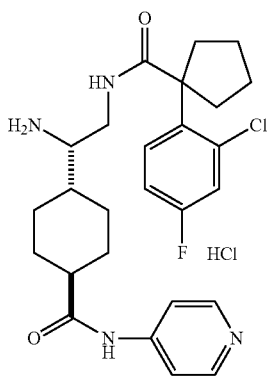 [SMILES: NC(CNC(=O)C1(c2ccc(F)cc2Cl)CCCC1)[C@H]1CC[C@H](C(=O)Nc2ccncc2)CC1 ; Cl]

Figure 11:
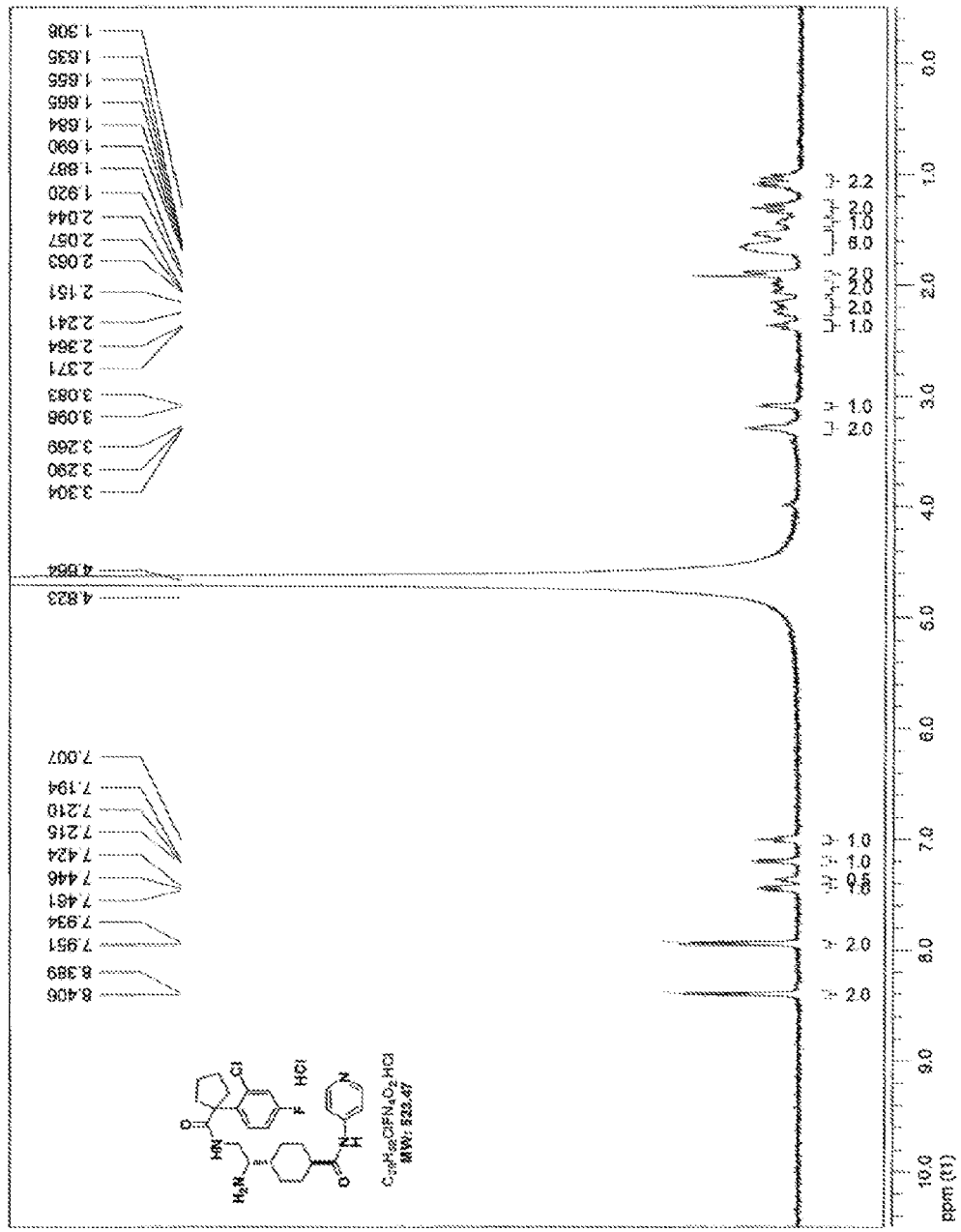

M.F.: $C_{26}H_{32}ClFN_4O_2 \cdot HCl$; M.W.: 523.47 (free base: 487.01); purity: 97.67% by AUC at 254 nm (HPLC); MS (ESI+ve): $[M+H, ^{35}Cl]^+=487.1$; $[M+H, ^{37}Cl]^+=489.2$ (free base). For $^1H$ NMR DMSO-$d_6$, see FIG. 11.

Compound 5

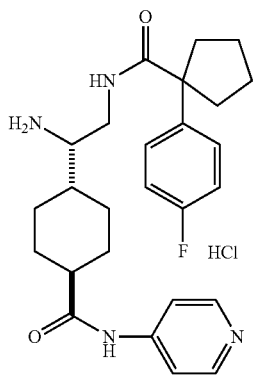 [SMILES: NC(CNC(=O)C1(c2ccc(F)cc2)CCCC1)[C@H]1CC[C@H](C(=O)Nc2ccncc2)CC1 ; Cl]

Figure 12:
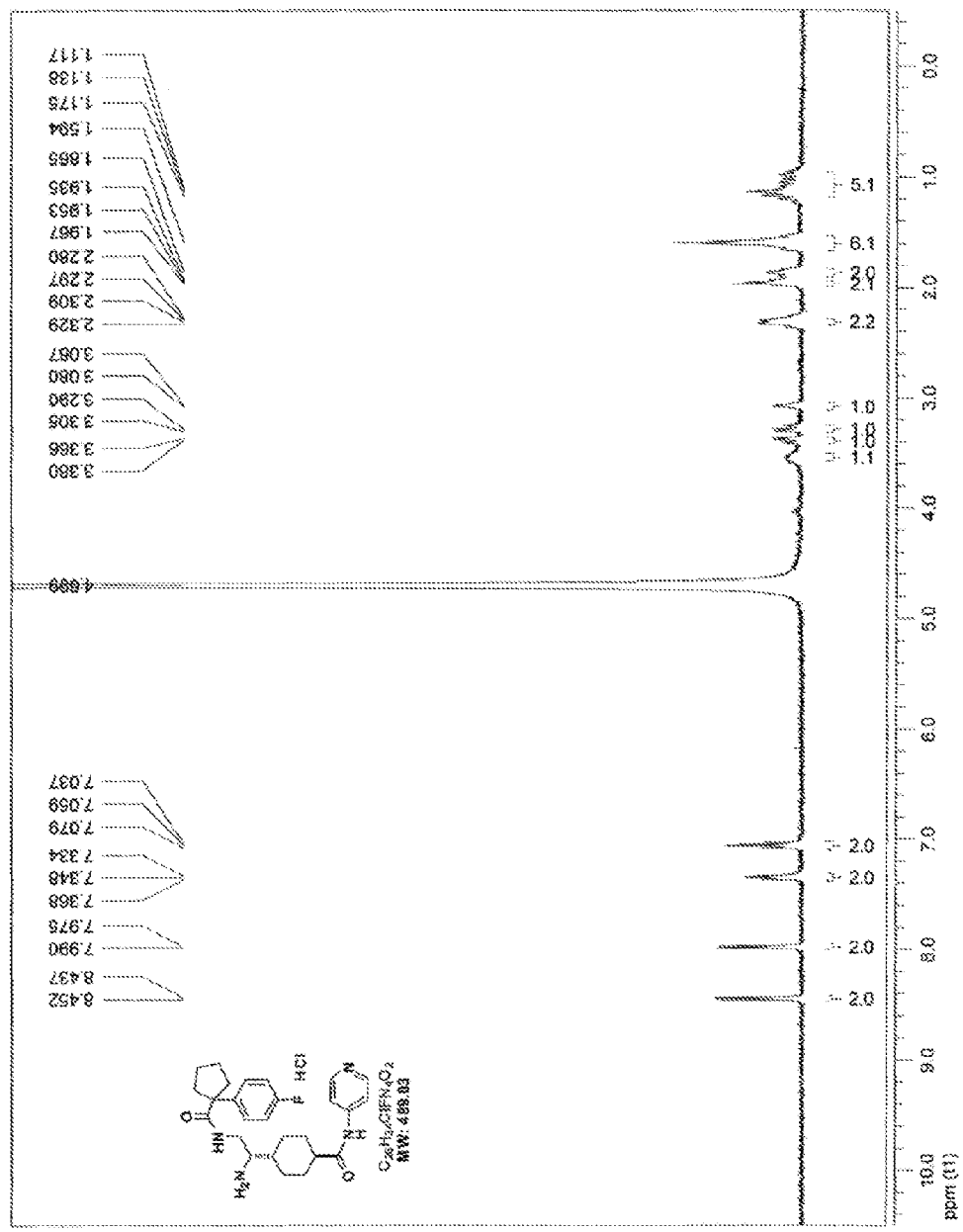

M.F.: $C_{26}H_{33}FN_4O_2 \cdot HCl$; M.W.: 489.03 (free base: 452.56); purity: 95.98% by AUC at 254 nm (HPLC); MS (ESI+ve): $[M+H]^+=453.2$ (free base). For $^1H$ NMR $D_2O$, see FIG. 12:

Compound 6

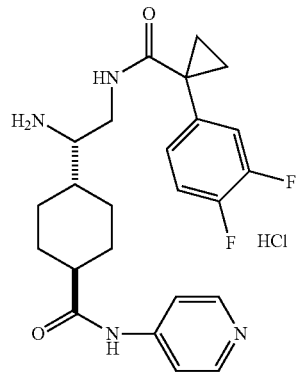 [SMILES: NC(CNC(=O)C1(c2ccc(F)c(F)c2)CC1)[C@H]1CC[C@H](C(=O)Nc2ccncc2)CC1 ; Cl]

Figure 13:
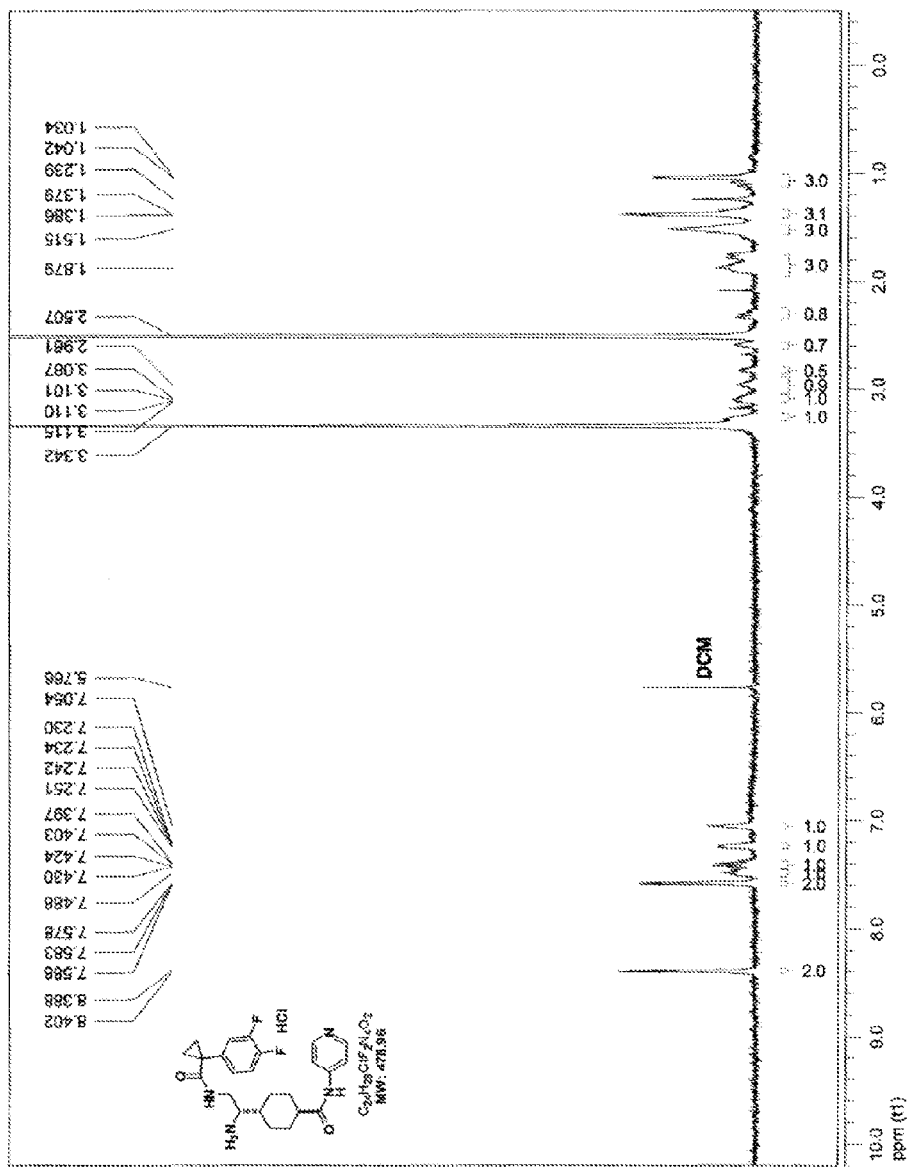

M.F.: $C_{24}H_{28}F_2N_4O_2 \cdot HCl$; M.W.: 478.96 (free base: 442.50); purity: 95.19% by AUC at 254 nm (HPLC); MS (ESI+ve): $[M+H]^+=443.1$ (free base). For $^1H$ NMR DMSO-$d_6$, see FIG. 13.

Compound 7

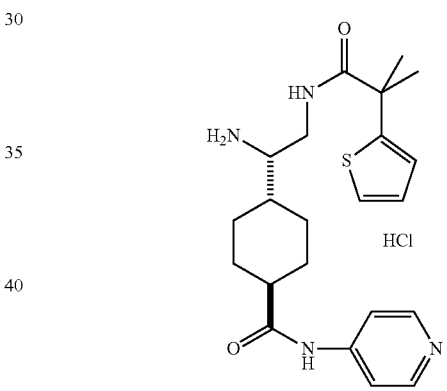

Figure 14:
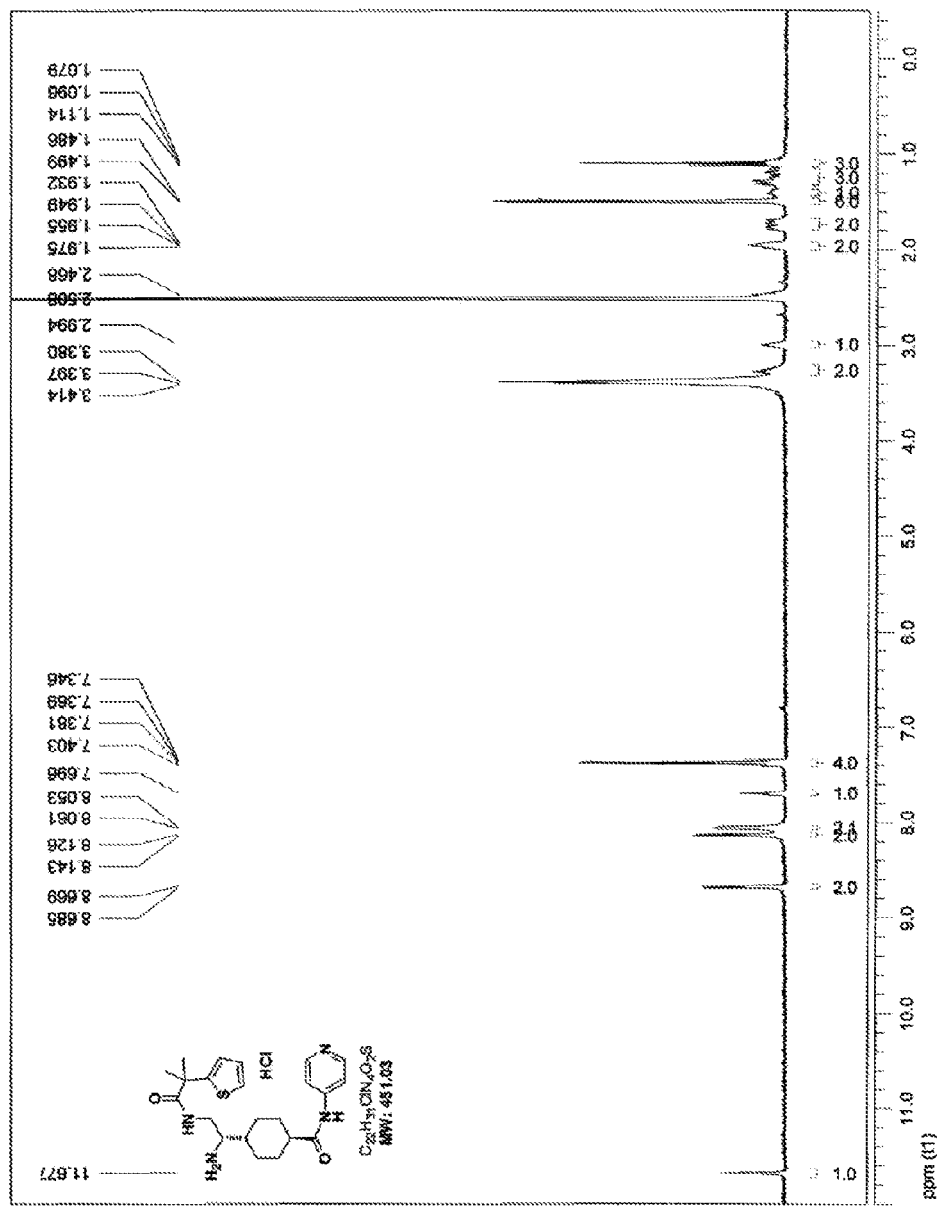

M.F.: $C_{22}H_{30}N_4O_2S \cdot HCl$; M.W.: 451.03 (free base: 414.56); purity: 96.71% by AUC at 254 nm (HPLC); MS (ESI+ve): $[M+H]^+=415.2$ (free base). For $^1H$ NMR DMSO-$d_6$, see FIG. 14.

Compound 8

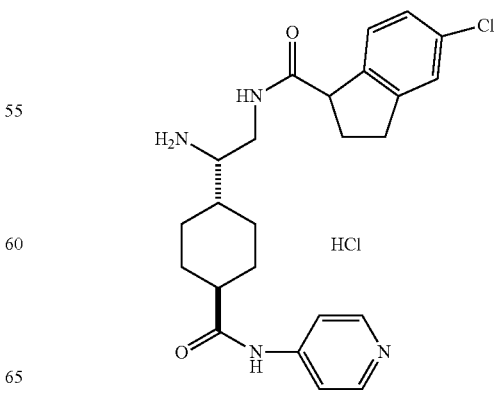

Figure 15:
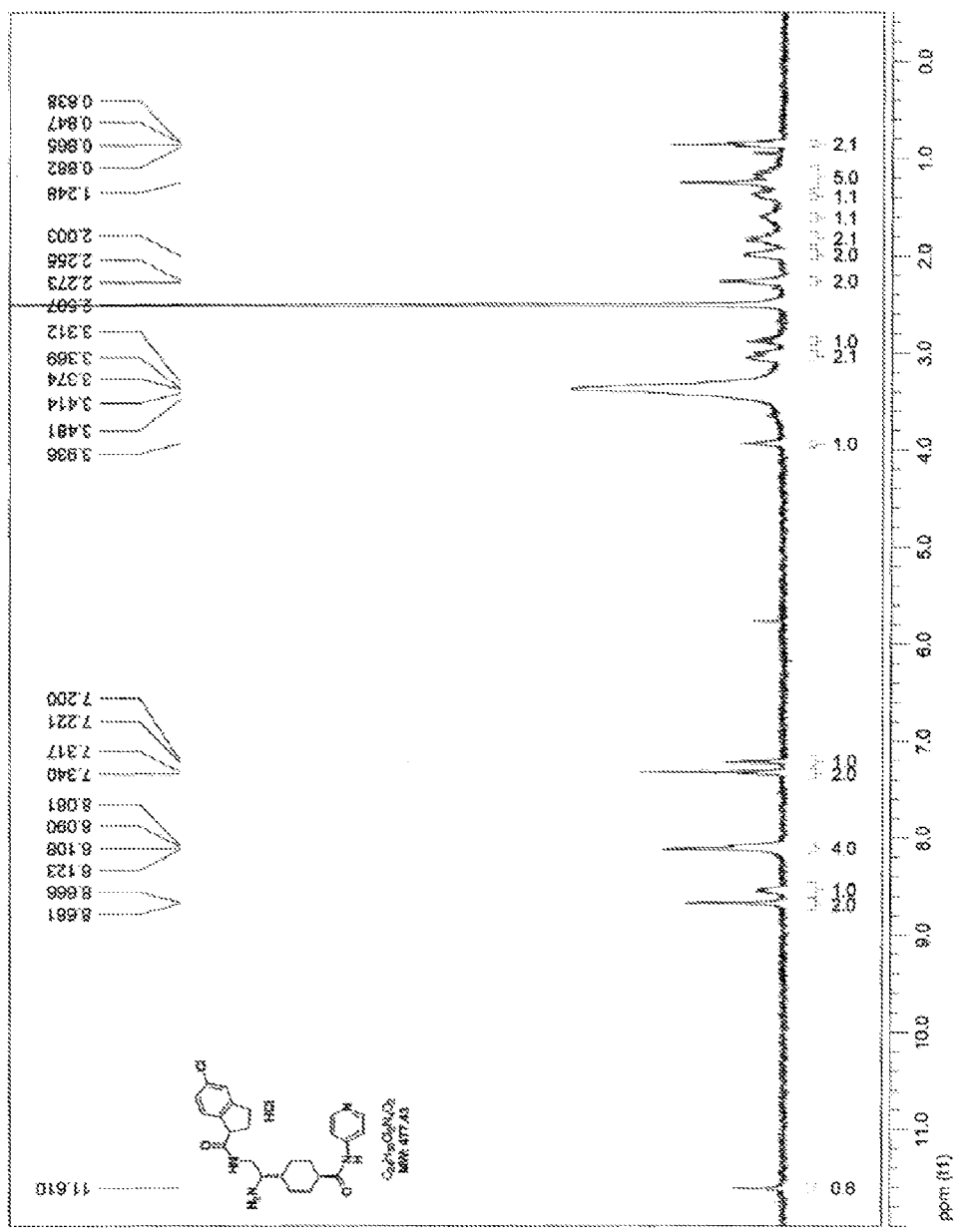

M.F.: C$_{24}$H$_{29}$ClN$_4$O$_2$.HCl; M.W.: 477.43 (free base: 440.97); purity: 100% by AUC at 254 nm (HPLC); MS (ESI+ve): [M+H, $^{35}$Cl]$^+$=441.1; [M+H, $^{37}$Cl]$^+$=443.1 (free base). For $^1$H NMR DMSO-d$_6$, see FIG. 15.

Compound 9

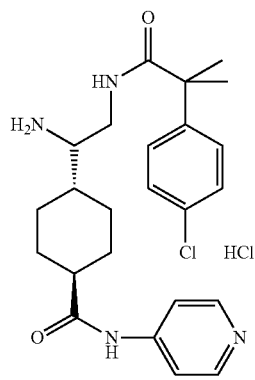 [SMILES: CC(C)(C(=O)NCC(N)[C@H]1CC[C@H](C(=O)Nc2ccncc2)CC1)c1ccc(Cl)cc1 ; Cl]

Figure 16:
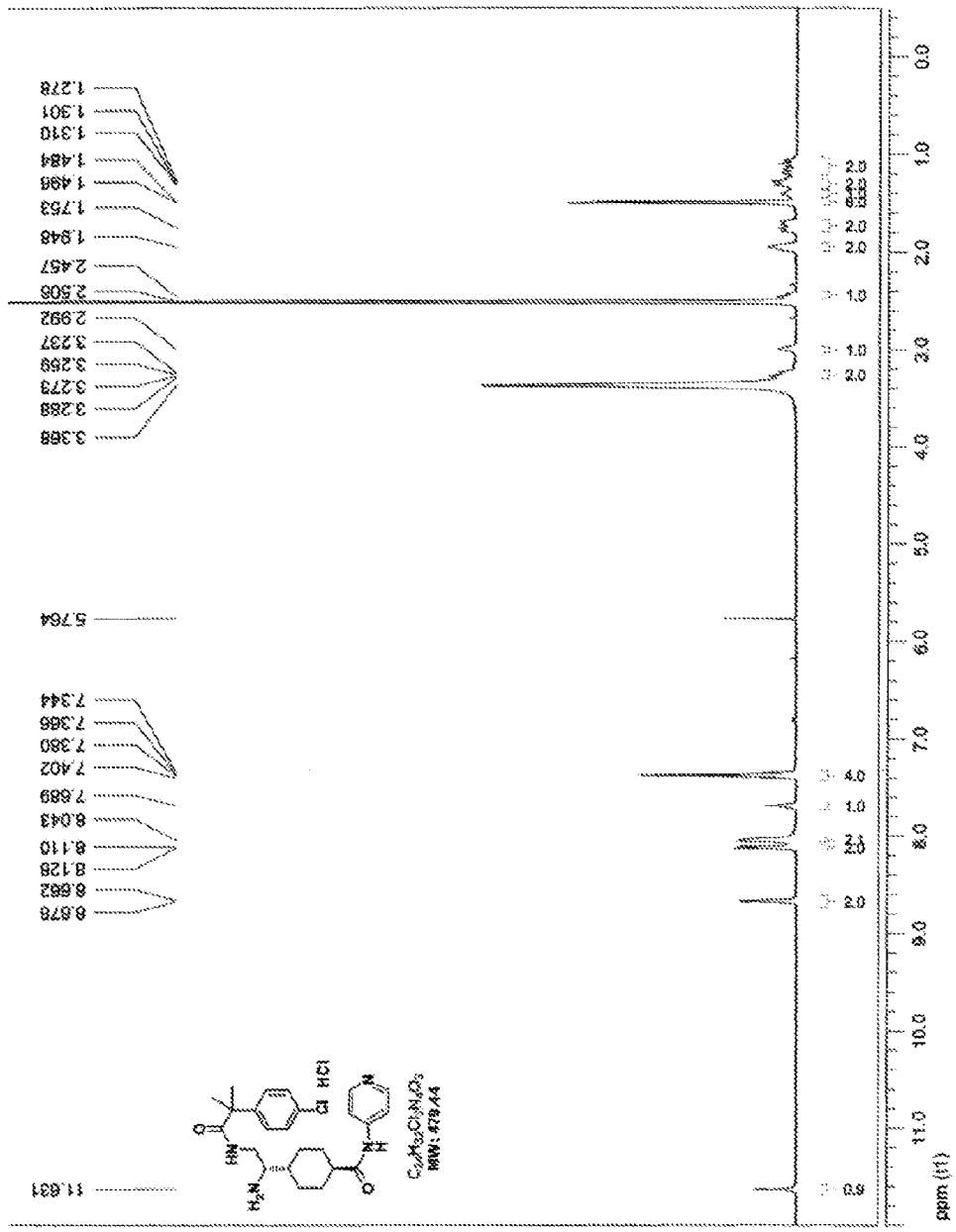

M.F.: C$_{24}$H$_{31}$ClN$_4$O$_2$.HCl; M.W.: 479.44 (free base: 442.98); purity: 95.34% by AUC at 254 nm (HPLC); MS (ESI+ve): [M+H]$^+$=443.1 (free base). For $^1$H NMR DMSO-d$_6$, see FIG. 16.

Example 2

Synthesis of trans-4-[1-Amino-2-[[[1-(4-chlorophenyl)cyclopropyl]methylamino]carbonyl]ethyl]-N-4-pyridinyl-cyclohexylcarboxamide (2)

Scheme 2

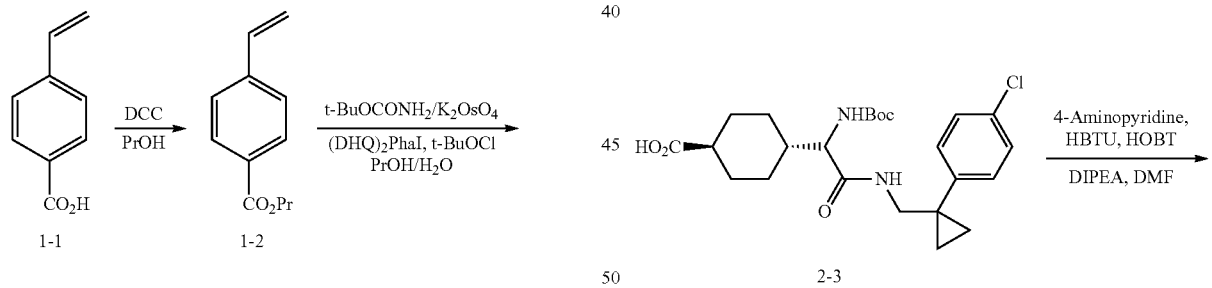

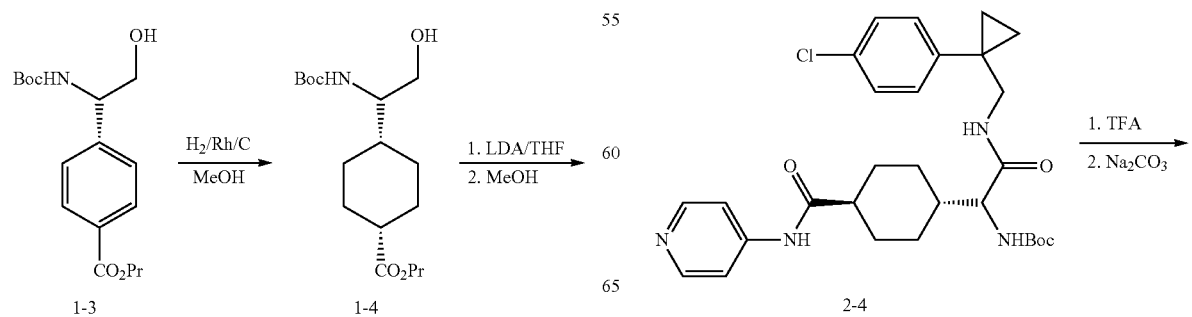

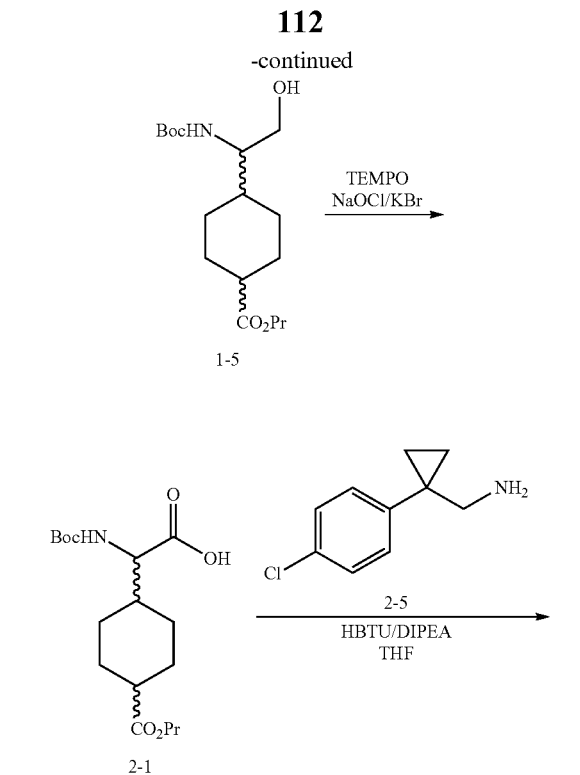

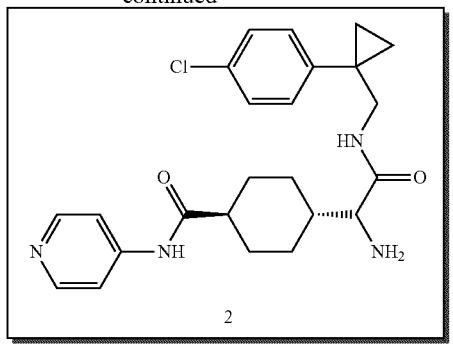

2

Synthesis of 4-(tert-Butoxycarbonylamino-carboxymethyl)cyclohexane-carboxylic acid propyl ester (2-1)

Figure 17:
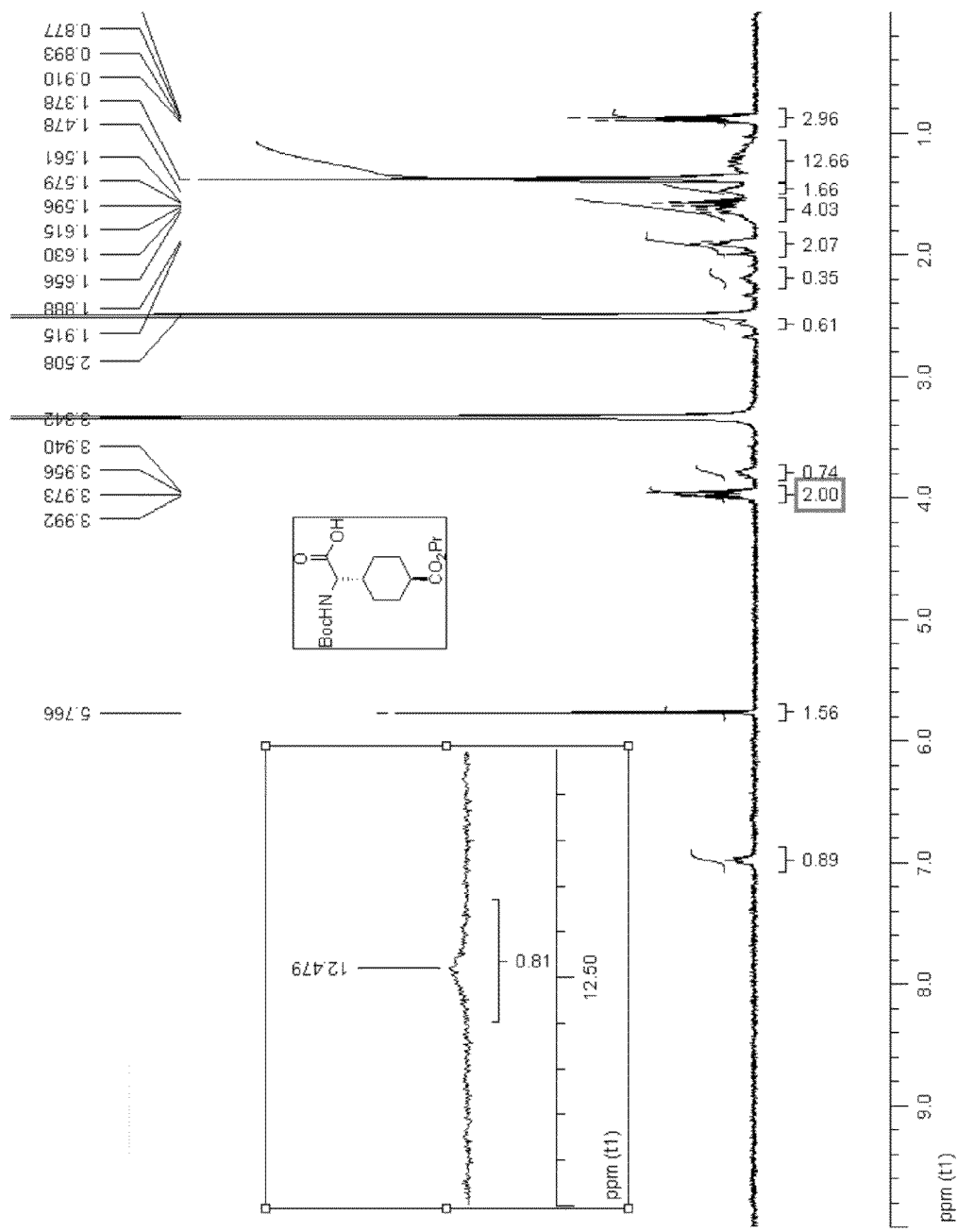
FIGS. 17-21 show $^1$H NMR data with DMSO solvent of the indicated compounds of Example 2.

5% NaHCO$_3$ (16 mL) was added to a 250 mL RB flask. A solution of cis-/trans-4-(1-tert-Butoxycarbonylamino-2-hydroxy-ethyl)cyclohexanecarboxylic acid propyl ester (1-5, prepared according to Example 1) (1.65 g, 1 eq) in acetone (37 mL) was added. The mixture was cooled to 0° C. with an ice-H$_2$O bath. KBr (119.00, 60 mg, 0.1 eq) was added, followed by the addition of TEMPO (825 mg, 1.05 eq). Bleach (12.5 mL) was added dropwise. The reaction mixture was stirred at 0° C. for 1 hour. Another portion of bleach (4.7 mL) was added. The reaction mixture stir at 0° C. for 1 hour, followed by the addition of 5% NaHCO$_3$ (19 mL). TLC and LC/MS indicated the absence of starting material. Acetone was removed under vacuum. The aqueous mixture was extracted with Et$_2$O (2×30 mL). The aqueous layer was acidified to pH=3 with 10% HCl while cooling with ice-H$_2$O bath, and then extracted with EtOAc (3×50 mL). The combined EtOAc was washed with brine. After drying over Na$_2$SO$_4$ and filtration, the filtrate was concentrated under vacuum to give 4-(tert-Butoxycarbonylamino-carboxy-methyl)-cyclohexanecarboxylic acid propyl ester (2-1) 1.71 g in 99.4% yield. The $^1$H NMR (DMSO-d$_6$) data is depicted in FIG. 17.

Synthesis of 4-(tert-Butoxycarbonylamino-{[1-(4-chloro-phenyl)cyclopropyl-methyl]-carbamoyl}-methyl)-cyclohexanecarboxylic acid propyl ester (2-2)

Figure 18:
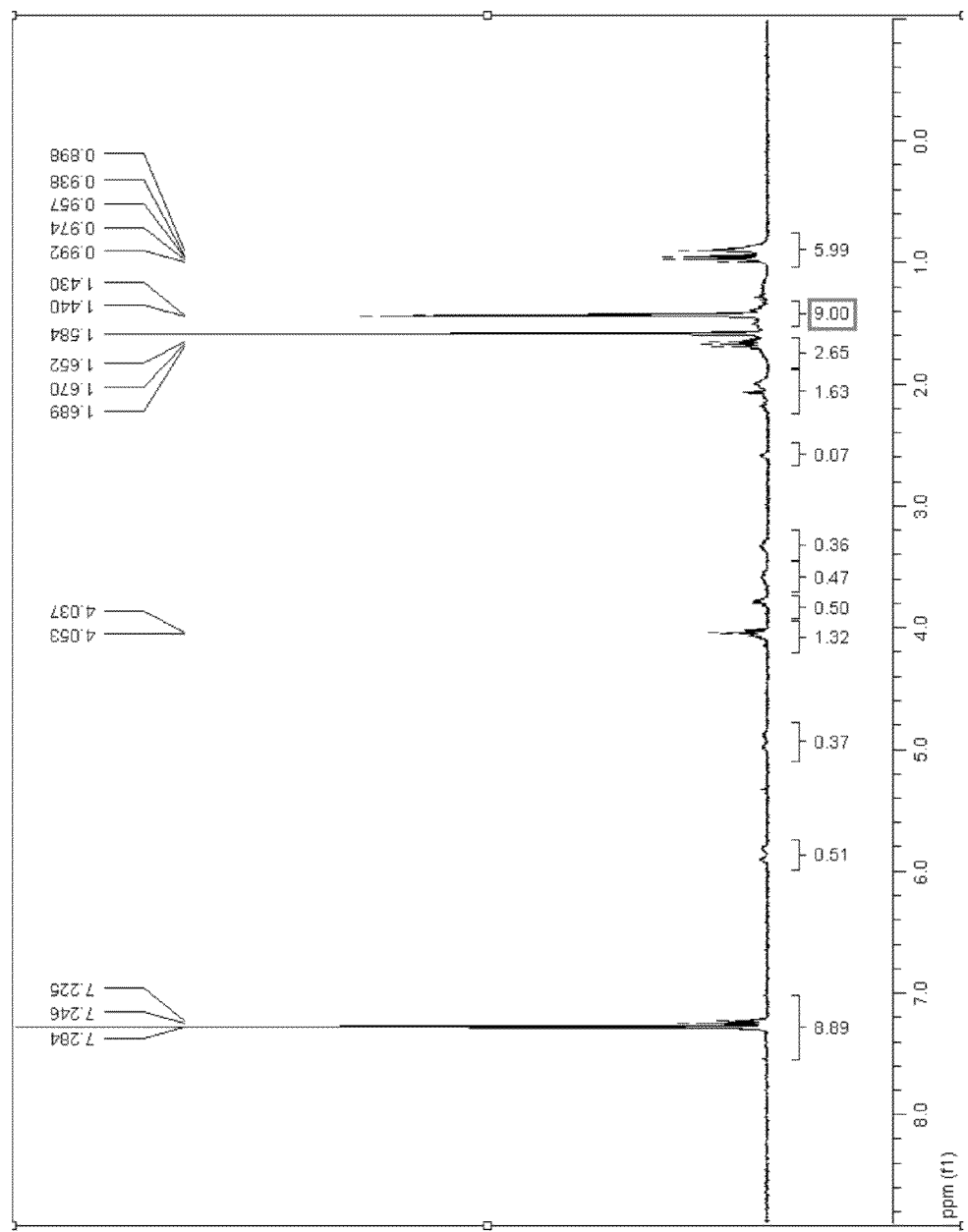

The acid (1.65 g, 0.0048 mol, 1 eq) was dissolved in anhydrous DMF (27 mL) under argon. 1-(4-Chloro-phenyl)-cyclopropylmethylamine (2-5) (0.87 g, 0.0048 mol, 1 eq) was added followed by, DIPEA (1.7 mL, 0.0098 mol, 2 eq) and HBTU (2.37 g, 0.0062 mol, 1.3 eq). The reaction mixture was stirred at RT and monitored by TLC and LC/MS for 16 hours. The amine (130 mg) and DIPEA (1.7 mL) were added. The reaction mixture was stirred at 50° C. for 3 hours. The reaction mixture was poured into H$_2$O (300 mL) and extracted with EtOAc (3×60 mL) The combined EtOAc was washed with brine. After drying over Na$_2$SO$_4$, the crude product was purified on silica gel column, eluting with EtOAc/Hexanes (1525%) to obtain 4-(tert-Butoxycarbonylamino-{[1-(4-chloro-phenyl)-cyclopropylmethyl]-carbamoyl}-methyl)-cyclohexanecarboxylic acid propyl ester (2-2) 1.77 g (90.8%). $^1$H NMR (CDCl$_3$) data is depicted in FIG. 18.

Synthesis of trans-4-(tert-Butoxycarbonylamino-{[1-(4-chloro-phenyl)-cyclopropylmethyl]-carbamoyl}-methyl)-cyclohexanecarboxylic acid (2-3)

Figure 19:
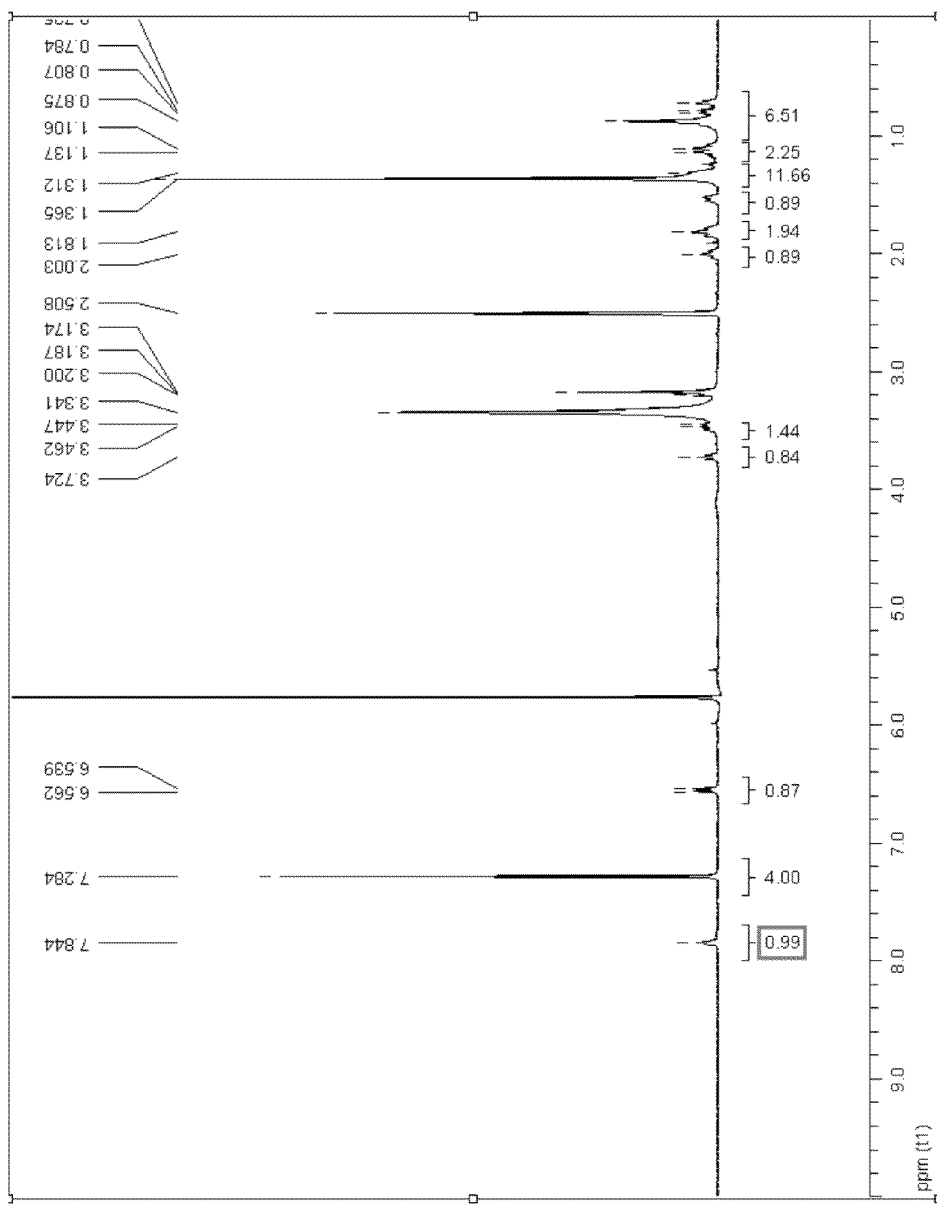

4-(tert-Butoxycarbonylamino-{[1-(4-chloro-phenyl)-cyclopropylmethyl]-carbamoyl}-methyl)-cyclohexanecarboxylic acid propyl ester (2-2) (1.77 g, 0.0035 mol, 1 eq) was dissolved in MeOH (20 mL) and THF (6 mL). NaOH (0.42 g, 0.0105 mol, 3 eq) in H$_2$O (2 mL) was added. The reaction mixture was stirred at RT and monitored by TLC and LC/MS. After stirring at RT for 20 hours, the reaction mixture was diluted with H$_2$O. The pH was adjusted to pH=3 with 10% HCl while cooling with ice-H$_2$O bath. The aqueous was extracted with EtOAc (3×60 mL). The combined EtOAc was washed with brine. After drying over Na$_2$SO$_4$ and filtration, the filtrate was concentrated under vacuum to dryness. The crude product was purified on silica gel column, eluted with 2% MeOH/CH$_2$Cl$_2$ to give trans-4-(tert-Butoxycarbonylamino-{[1-(4-chloro-phenyl)-cyclopropylmethyl]-carbamoyl}-methyl)-cyclohexanecarboxylic acid 0.56 g (2-3) (34.4%). $^1$H NMR (DMSO-d$_6$) data is depicted in FIG. 19.

Synthesis of Boc-trans-4-[1-Amino-2-[[[1-(4-chlorophenyl)cyclopropyl]-methylamino]carbonyl]ethyl]-N-4-pyrdinyl-cyclohexykarboxamide (2-4)

Figure 20:
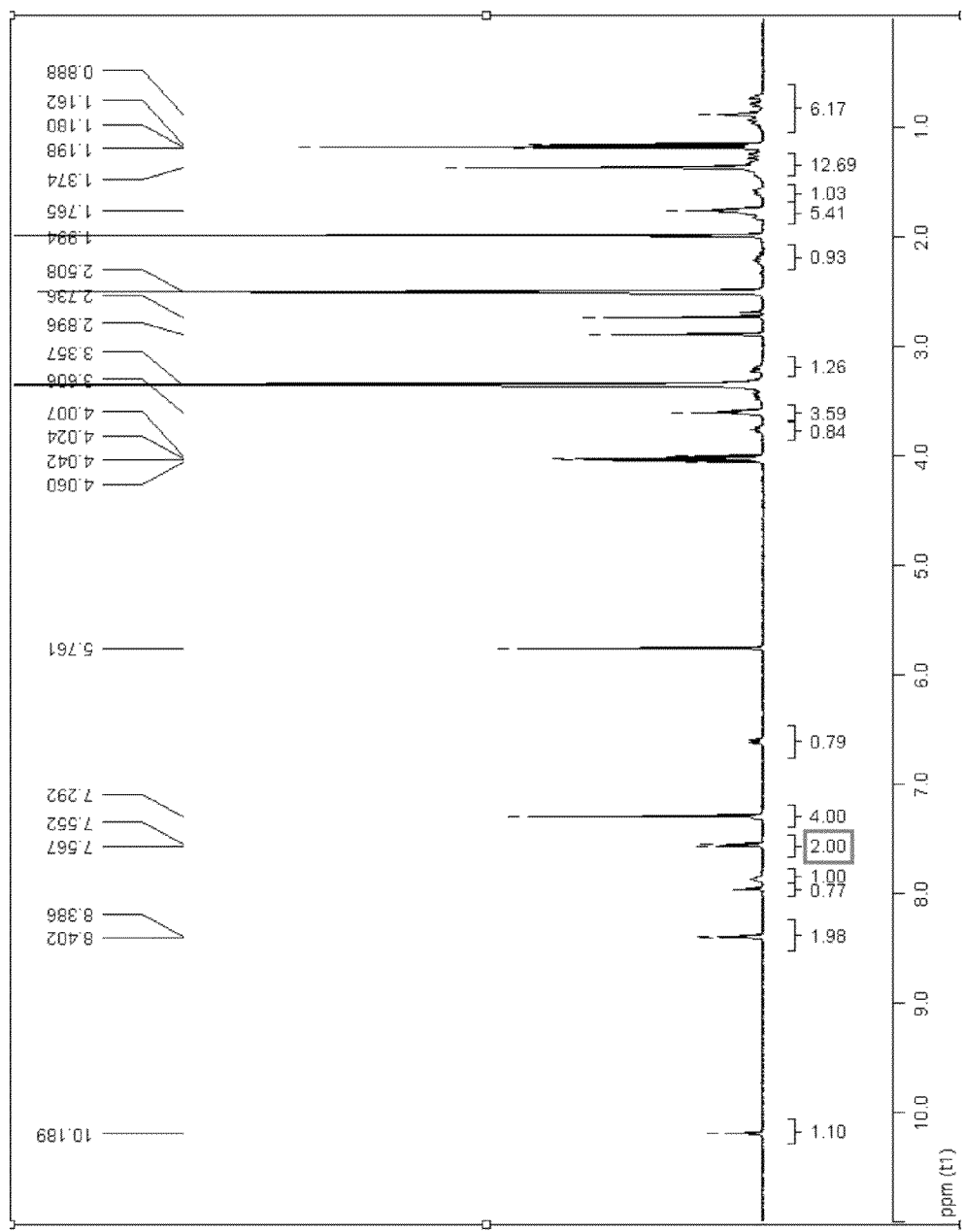

Trans-4-(tert-Butoxycarbonylamino-{[1-(4-chloro-phenyl)-cyclopropylmethyl]-carbamoyl}-methyl)-cyclohexanecarboxylic acid (2-3) (0.56 g, 0.00 12 mol, 1.0 eq) was dissolved in anhydrous DMF (12 mL) under argon. HBTU (0.503 g, 0.0013 mol, 1.1 eq) was added followed by DIPEA (0.42 mL, 0.0024 mol, 2 eq). The reaction mixture was stirred at RT for 10 minutes. 4-Aminopyridine (0.0018 mol, 1.5 eq) was added. The reaction mixture was stirred at RT and monitored by TLC and LC/MS. After 2 hours, the reaction mixture was diluted with H$_2$O (200 mL), and then extracted with EtOAc-THF (3×50 mL). The combined organic layer was washed with brine (1×50 mL). After drying over Na$_2$SO$_4$ and filtration, the filtrate was concentrated under vacuum. The precipitation was collected by filtration, and washed with CH$_2$Cl$_2$ to obtain 0.51 g Boc-trans-4-[1-Amino-2-[[[1-(4-chlorophenyl)-cyclopropyl]methylamino]carbonyl]ethyl]-N-4-pyridinyl-cyclohexylcarboxamide (2-4) (78.3%) as a white solid. $^1$H NMR (DMSO-d$_6$) data is depicted in FIG. 20.

Synthesis of trans-4-[1-Amino-2-[[[1-(4-chlorophenyl)cyclopropyl]methylamino]-carbonyl]ethyl]-N-4-pyridinyl-cyclohexylcarboxamide (2)

Figure 21:
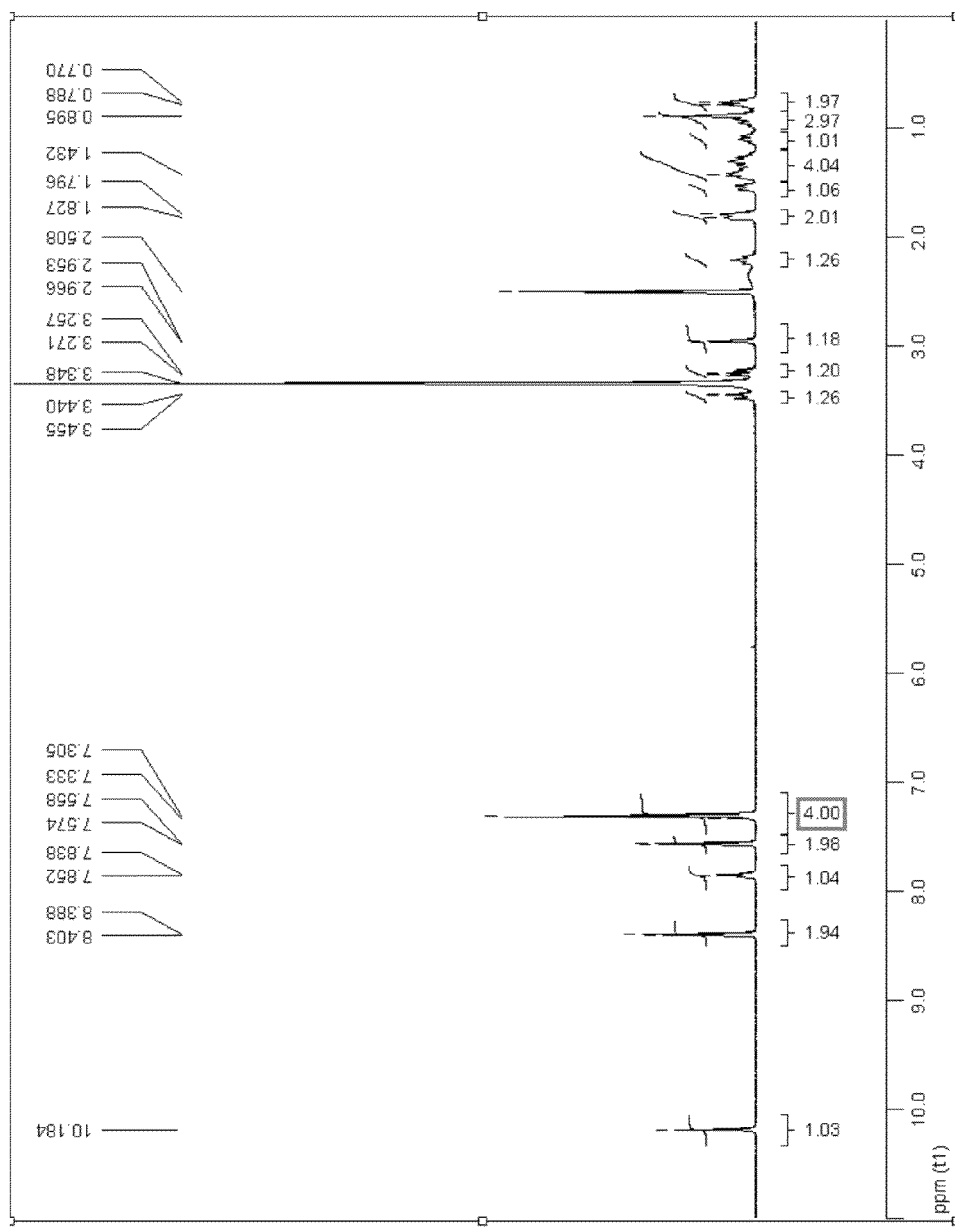

Boc-trans-4-[1-Amino-2-[[[1-(4-chlorophenyl)cyclopropyl]methylamino]carbonyl]ethyl]-N-4-pyridinyl-cyclohexylcarboxamide (2-4) (0.51 g) was dissolved in anhydrous DCM (10 mL). A 20% TFA/CH$_2$Cl$_2$ (10 mL, 2 mL of TFA in 8 mL of anhydrous CH$_2$Cl$_2$) solution was added. The reaction mixture was stirred at RT and monitored by LC/MS. After 60 minutes, the reaction mixture was poured into 20% Na$_2$CO$_3$ (100 mL). The white solid was collected by filtration, and washed with H$_2$O (2×20 mL). The solid was dried under vacuum at <50° C. to give 260 mg (62.6%) of trans-4-[1-Amino-2-[[[1-(4-chlorophenyl)cyclopropyl]methylamino]-carbonyl]ethyl]-N-4-pyridinyl-cyclohexylcarboxamide (2). 99% pure by HPLC (254 nm); MS (ESI) m/z=441.27 [M+H]$^+$ $_1$H NMR (DMSO-d$_6$) data is depicted in FIG. 21.

The following Compounds 10-12 were synthesized following procedures substantially as described for the synthesis of Compound 2 upon appropriate substitution of starting material.

Compound 10

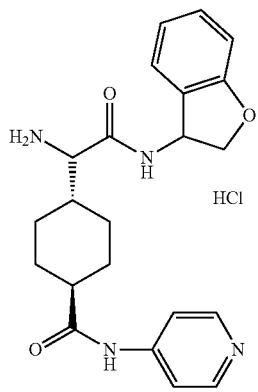

Figure 22:
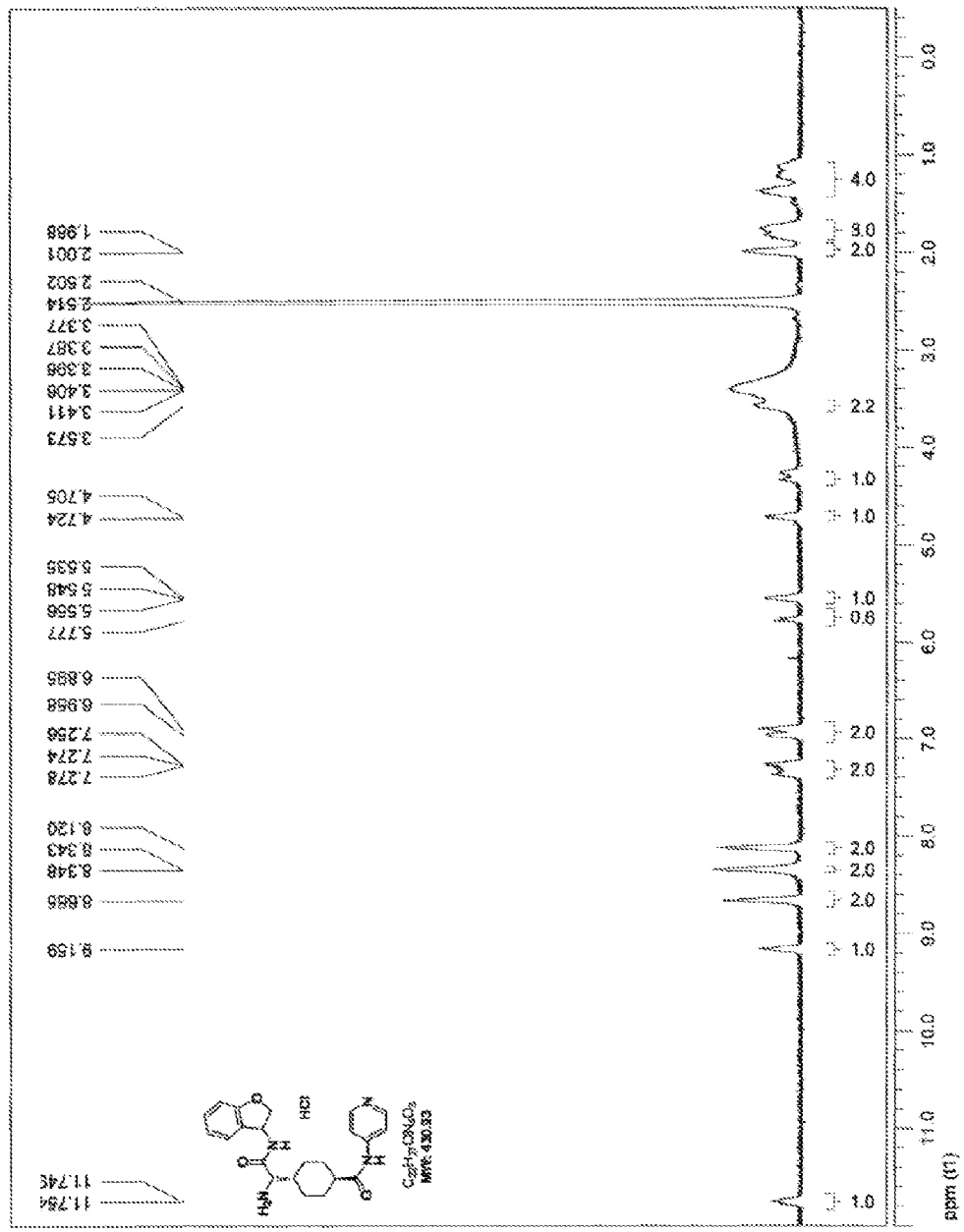
FIGS. 22-24 show $^1$H NMR data of certain other indicated compounds of Example 2.

M.W.: 430.93 (free base: 394.47); purity: 96.61% by AUC at 254 nm (HPLC); MS (ESI+ve): [M+H]$^+$=395.1 (free base). For $^1$H NMR DMSO-d$_6$, see FIG. 22.

Compound 11

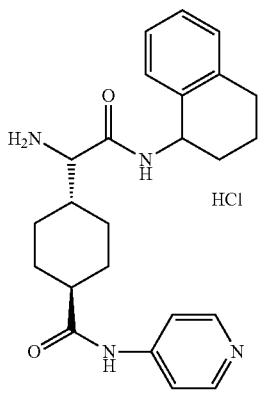 [SMILES: NC(C(=O)NC1CCCc2ccccc21)[C@H]1CC[C@H](C(=O)Nc2ccncc2)CC1 ; Cl]

Figure 23:
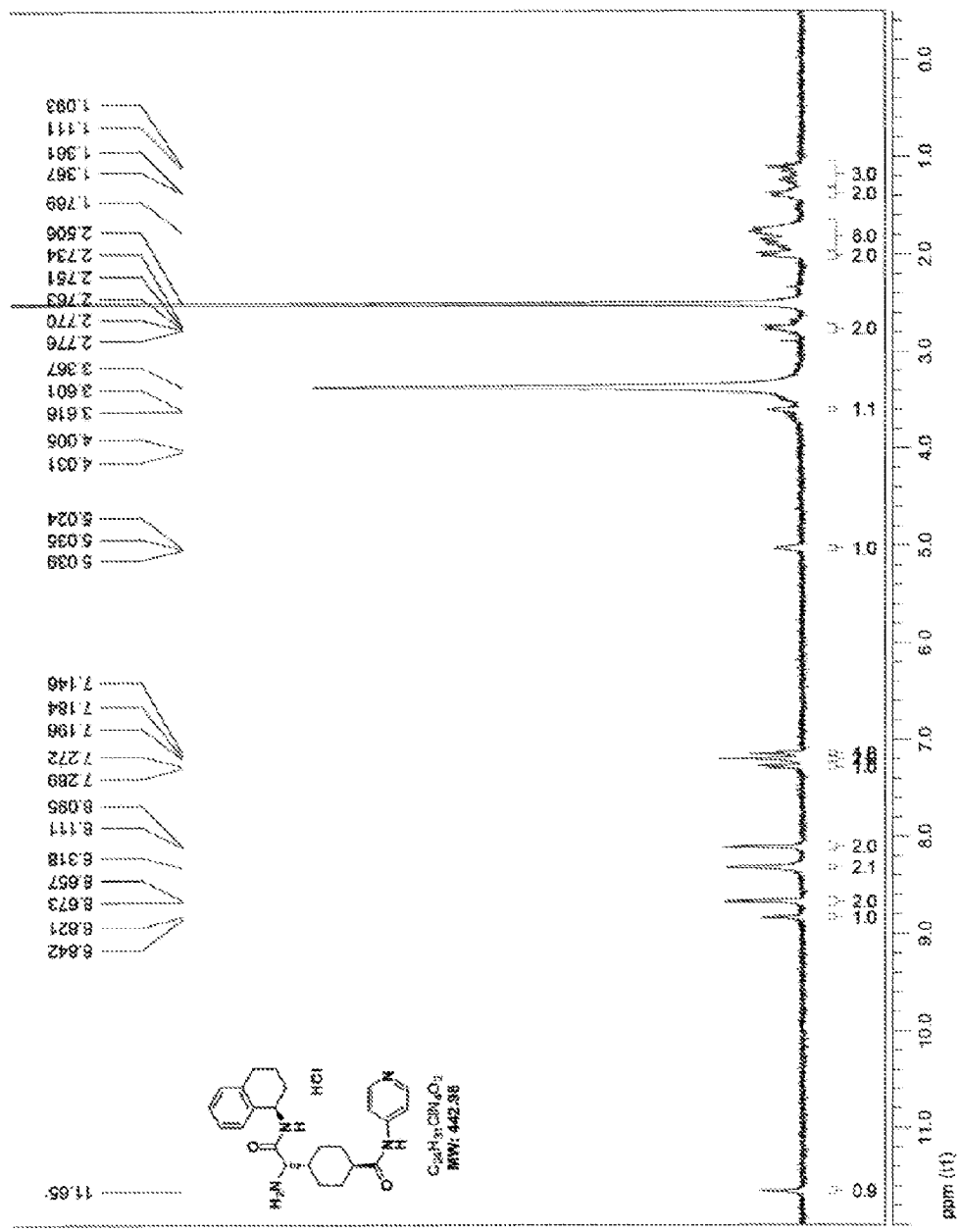

M.F.: $C_{24}H_{30}N_4O_2$.HCl; M.W.: 442.98 (free base: 406.52); purity: 98.01% by AUC at 254 nm (HPLC); MS (ESI+ve): [M+H]$^+$=407.1 (free base). For $^1$H NMR DMSO-d$_6$, see FIG. 23.

Compound 12

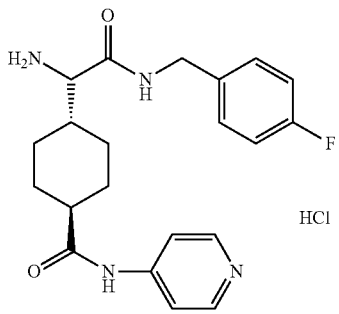 [SMILES: NC(C(=O)NCc1ccc(F)cc1)[C@H]1CC[C@H](C(=O)Nc2ccncc2)CC1 ; Cl]

Figure 24:
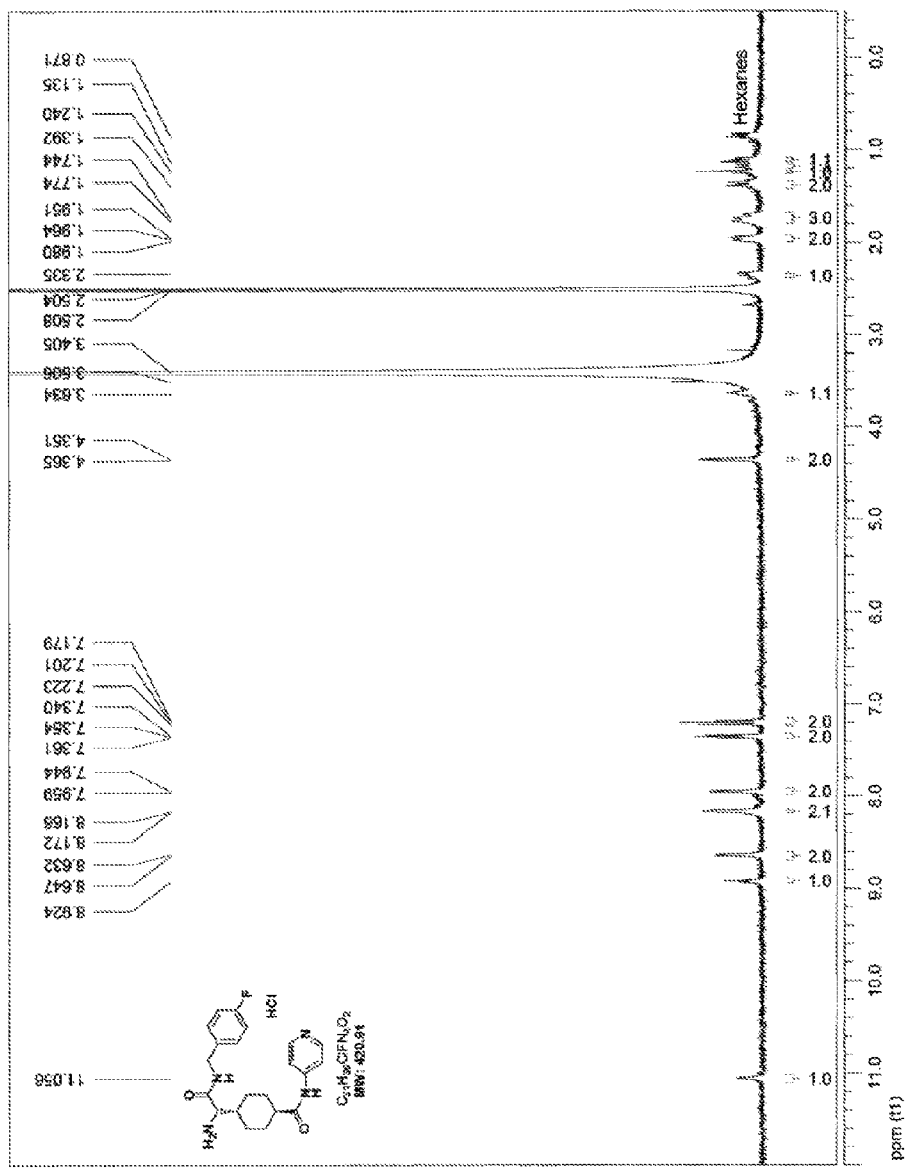

M.F.: $C_{21}H_{25}FN_4O_2$. HCl; M.W.: 420.91 (free base: 384.45); purity: 97.83% by AUC at 254 nm (HPLC); MS (ESI+ve): [M+H]$^+$=385.1 (free base). For $^1$H NMR, see FIG. 24.

Example 3

Biological Examples i. In Vitro PKCε Inhibition

The ability of the compounds disclosed herein to inhibit PKCε can be assessed using the primary PKCε assay described above using the biotinylated substrate KRFARKGSLRQKNV. Eight-point dose response curves can reveal the order of potency. Those compounds tested exhibited activity in this assay. The inhibitory effects of Compounds 1 and 2 are tabulated below:

| Compound | IC$_{50}$ (M) | Log IC$_{50}$ | Log IC$_{50}$ SE |
|---|---|---|---|
| 1 | 1.31E−07 | −6.883 | 0.02928 |
| 2 | 1.69E−06 | −5.773 | 0.1232 | ii. In Vitro Inhibition of Other PKC Isozymes and of ROCK1

The specificity of the compounds disclosed herein for inhibition of PKCε can be determined by examining their ability to inhibit ROCK1 and selected members of each PKC subfamily according to the protocols of the counter-screening assay for selectivity disclosed herein. This assay can be performed according to the biochemical assay for PKCε described above with some modifications.

Rather than varying the concentrations of the inhibitors, only 10 μM of each compound can be used. Those compounds tested exhibited selectivity against various PKC's as well as ROCK1 when screened in these assays.

iii. FRET Based LANCE Ultra Kinase Assay

Certain compounds of this invention were tested in the captioned assay. The results are tabulated below.

| Compound | IC$_{50}$ (M) | Log IC$_{50}$ | Log IC$_{50}$ SE |
|---|---|---|---|
| 1 | 5.66E−08 | −7.247 | 0.026 |
| 2 | 3.24E−06 | −5.489 | 0.071 |
| 3 | 1.46E−07 | −6.835 | 0.065 |
| 4 | 1.21E−07 | −6.917 | 0.027 |
| 5 | 4.26E−08 | −7.370 | 0.029 |
| 6 | 5.22E−08 | −7.282 | 0.061 |
| 7 | 2.80E−07 | −6.553 | 0.048 |
| 8 | 3.59E−07 | −6.445 | 0.053 |
| 9 | 4.00E−08 | −7.398 | 0.034 |
| 10 | 2.02E−06 | −5.695 | 0.114 |
| 11 | 3.09E−06 | −5.510 | 0.077 |
| 12 | 2.37E−06 | −5.625 | 0.094 | iv. In Vivo

The ability to reduce PKCε-dependent mechanical hyperalgesia can be tested by injecting 1 μg of a test compound into the rat hind paw immediately after injection of 1 μg ψεRack. Any decrease in threshold can be measured by the mechanical hyperalgesia assay. Those compounds tested compounds were capable of significantly reducing ψεRack-induced hyperalgesia at the test dose.

Example 4

Inhibition of PKCε and Other PKCs by Compounds of this Invention

This example demonstrates the PKC inhibitory efficacy of certain compounds of this invention. Compounds 1, 5, and 9:

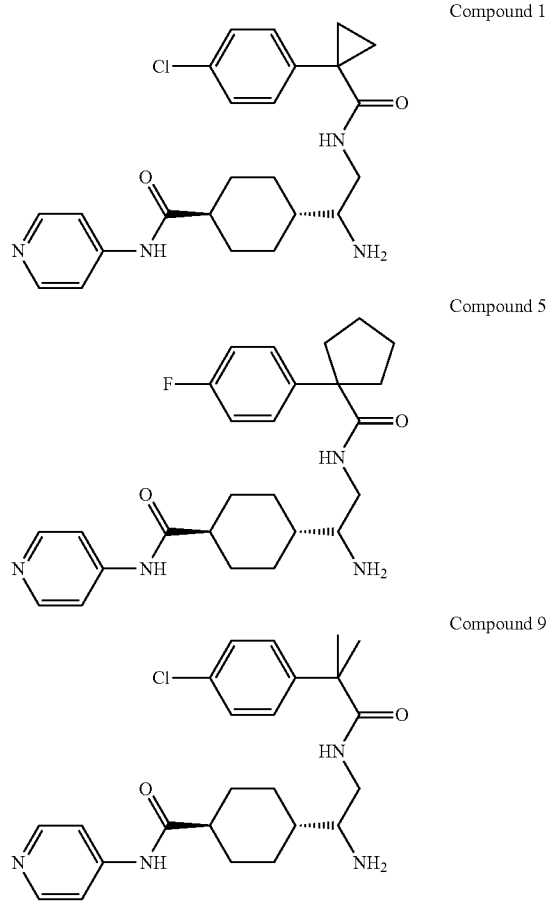

Compound 1

Compound 5

Compound 9 that inhibit PKCε with Ki<20 nM were selected for this test. They all inhibited conventional PKCγ at 10 μM, while compounds 5 and 9 showed almost no activity against atypical PKCζ at that concentration as tabulated below.

TABLE 4

Percent inhibition of PKC activity by 10 μM of each inhibitor (n = 3 each condition).

| | Conventional | Novel | | Atypical |
|---|---|---|---|---|
| Compound | PKCγ | PKCδ | PKCθ | PKCζ |
| 1 | 16.7 ± 3.8 | 96.3 ± 0.7 | 96.9 ± 1.1 | 55.9 ± 3.8 |
| 5 | 17.0 ± 1.3 | 96.4 ± 1.0 | 94.4 ± 1.0 | 6.3 ± 2.1 |
| 9 | 30.0 ± 3.3 | 98.9 ± 0.6 | 99.6 ± 1.3 | 8.9 ± 1.8 |

All the compounds inhibited the highly related novel PKCs: PKCδ and PKCθ, but showed some selectivity within the novel PKC subfamily, being about 6 to 10-fold less potent in inhibiting PKCδ and PKCθ than PKCε as tabulated below.

TABLE 5

Ki and Log IC50 ± SE values for inhibition of novel PKCs (n = 3).

| | PKCε | | PKCδ | | PKCθ | |
|---|---|---|---|---|---|---|
| Compound | Ki (nM) | Log IC50 (M) | Ki (nM) | Log IC50 (M) | Ki (nM) | Log IC50 (M) |
| 1 | 17.0 | −7.26 ± 0.06 | 172.7 | −6.15 ± 0.14 | 91.7 | −6.43 ± 0.08 |
| 5 | 12.8 | −7.37 ± 0.03 | 124.7 | −6.28 ± 0.12 | 86.9 | −6.44 ± 0.04 |
| 9 | 9.3 | −7.42 ± 0.07 | 66.5 | −6.57 ± 0.11 | 67.0 | −6.56 ± 0.10 |

Example 5

Compound 1 Increases LORR In Vivo

This example demonstrates that a compound of this invention possesses CNS related activity and prolongs loss of righting reflex (LORR) duration in vivo. Compound 1 was administered (10 mg/kg) i.p. to C57BL/6 mice, which were administered 20 min later 3.6 g/kg ethanol i.p. to induce loss of righting. It was found that Compound 1 increased the LORR duration by 45%, from 31.4±4.9 (n=8) in vehicle-treated mice to 45.7±4.0 (n=10) in drug-treated mice (p=0.036). These findings indicate that this class of compounds can cross the blood-brain barrier and act as a PKCε inhibitor, and prolong the duration of the LORR in the treated animals. Such increased signs of ethanol intoxication are contemplated to be aversive and to limit ethanol self-administration. Therefore, this example demonstrates that compounds of this invention are suitable for treating alcohol abuse and substance abuse disorders.

Example 6

In Vivo Testing of the Compounds of this Invention

Wild type C57BL6/NTac mice are used as subjects. Compounds are dissolved at a stock concentration of 10 mg/ml. For injection, the stock is diluted 1:20 in saline to a final concentration of 0.5 mg/ml, with 5% DMSO and 20% Cremophor-EL added as needed to keep the compounds in solution. Kinase inhibition is assayed by measuring phosphorylation of γ2S327 normalized to total γ2 subunit immunoreactivity. For each compound, it is determined if the drug enters the brain and for how long. Dosing starts at 10 mg/kg i.p. and the plasma and brain levels of the administered compounds is measured in animals euthanized after 5 min, 30 min, 1 h, 2 h, 4 h and 8 h. The plasma and brain half-lives of the drug is determined using a one-phase exponential decay model $[Y=(Y_{t=0})*e^{-K*X}]$, where the final concentration (plateau)=0 and $t_{1/2}=0.6932/K$. The inhibition of PKCε is measured by administering a range of doses (0.3-30 mg/kg), and then euthanizing animals by microwave fixation at a time when inhibition should be maximal to assay samples of amygdala, dorsal striatum, and nucleus accumbens for γ2-S (P)327 immunoreactivity.

The doses that decrease ethanol intake are determined using a limited access, two bottle choice drinking procedure. See, Lesscher et al., "Amygdala protein kinase C epsilon controls alcohol consumption," Genes Brain Behav. 8:493-9, 2009, incorporated herein in its entirety by reference. In this paradigm animals are given access to two drinking tubes, one containing 15% ethanol and the other tap water 2 h after the beginning of the dark phase of a 12-h light:12-h dark cycle for a period of 2 h. Under this procedure, ethanol consumption escalates and then stabilizes by 3 weeks, results in BECs of 50-60 mg/dl in C57BL/6J×129S4/SvJae hybrid mice, and can be reduced by administering 1 mg/kg naltrexone. The doses of each compound that enhance ethanol-induced ataxia using a fixed-speed rotarod. Mice are trained to remain on the rotarod for 3 min and are then administered 2.0 g/kg ethanol i.p., which renders them completely unable to remain on the rotarod 5 min later. Their latency to fall from the rod is measured every 15 min until they recover and are able to remain on the rotarod for a full 3 min. The doses of each compound that prolong the ethanol-induced loss of the righting reflex are determined by administering 4.0 g/kg ethanol by measuring the duration of the ethanol-induced loss of righting and the blood ethanol concentration upon recovery. The range of doses that inhibits γ2S327 phosphorylation is used to adjust the dose range as needed to alter these behaviors. To determine if the inhibitors alter ethanol clearance, the mice are injected 4.0 g/kg ethanol and the decline in their blood ethanol concentration (BEC) is measured 1, 2, 3 and 4 h later. The effect of ethanol to alter the amount of inhibitor in plasma or that reaches the brain is determined by administering 4 g/kg ethanol, 30 min later administering 25 mg/kg of a kinase inhibitor, and 1 h later measuring plasma and brain levels of that inhibitor by LC/MS/MS.

What is claimed is:

1. A method for treating a patient suffering from a disease or disorder selected from the group consisting of pain, substance abuse substance dependencies and depression, which method comprises administering to a patient an effective amount of a compound of Formula I or a salt thereof:

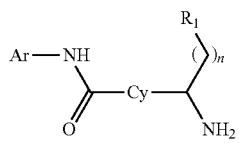

wherein
Ar is pyridyl;
Cy is selected from the group consisting of cyclohexyl, adamantyl and piperidinyl;
n is 0 or −1; and
$R^1$ is selected from:

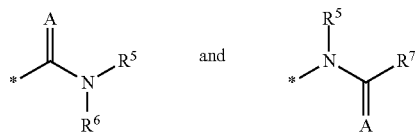

with the proviso that when n is 0, then $R^1$ is

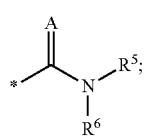

A is oxygen or sulfur; and
$R^5$, $R^6$ and $R^7$ are each independently selected from the group consisting of hydrogen, alkyl, cycloalkyl, or heterocyclyl, where the cycloalkyl or heterocyclyl group may be fused to one phenyl or pyridyl group, and where each of said alkyl, cycloalkyl, heterocyclyl, phenyl or pyridyl groups is-optionally substituted by halo, aryl, cycloalkyl, phenyl or pyridyl.

2. The method of claim 1, represented by Formula Ia, Ib or Ic:

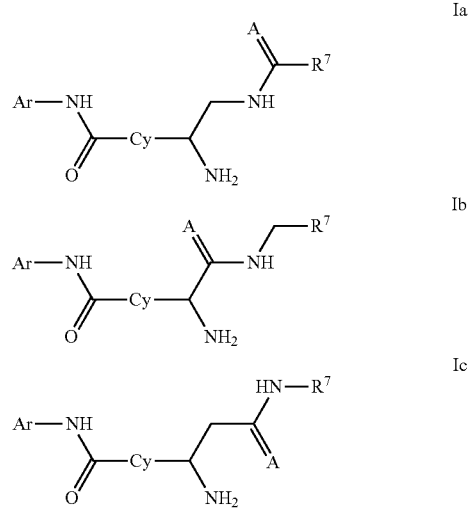

wherein
Ar is pyridyl;
Cy is selected from the group consisting of cyclohexyl, adamantyl and piperidinyl;
A is oxygen or sulfur; and
$R^7$ is selected from the group consisting of hydrogen, alkyl, cycloalkyl, or heterocyclyl, where the cycloalkyl or heterocyclyl group may be fused to one phenyl or pyridyl group, and where each of said alkyl, cycloalkyl, heterocyclyl, phenyl or pyridyl groups is-optionally substituted by halo, aryl, cycloalkyl, phenyl or pyridyl.

3. The method of claim 2, represented by Formula IIIa, IIIb or IIIc:

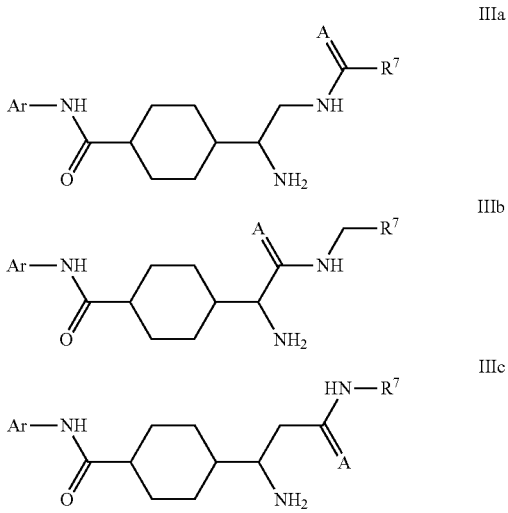

wherein Ar, A, and $R^7$ are as defined therein;
or a salt thereof.

4. The method of claim 2, wherein Cy is selected from the group consisting of adamantyl and piperidinyl or a salt thereof.

5. The method of claim 1, wherein the compound is selected from Table 1:

TABLE 1

Compound

TABLE 1-continued
Compound
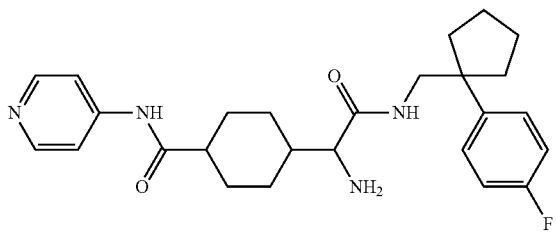
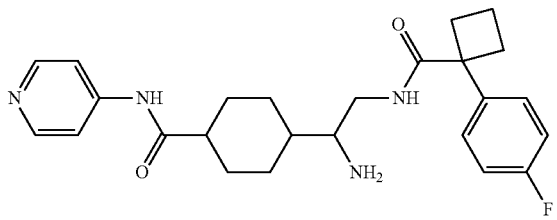 [SMILES: NC(CNC(=O)C1(c2ccc(F)cc2)CCC1)C1CCC(C(=O)Nc2ccncc2)CC1]
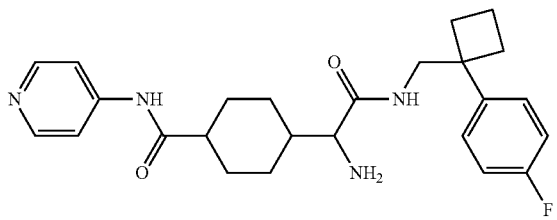
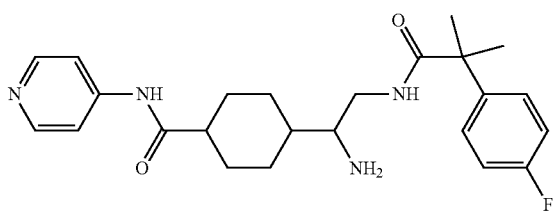
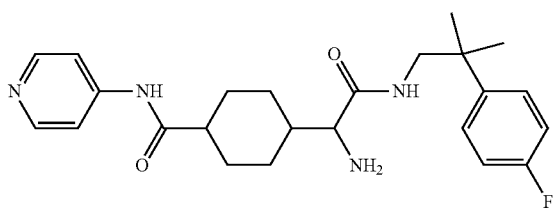 [SMILES: CC(C)(CNC(=O)C(N)C1CCC(C(=O)Nc2ccncc2)CC1)c1ccc(F)cc1]
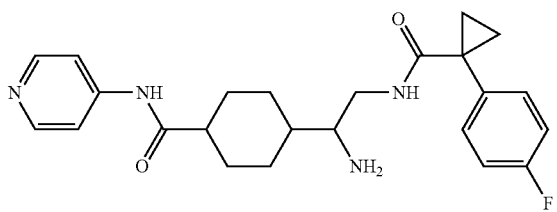 [SMILES: NC(CNC(=O)C1(c2ccc(F)cc2)CC1)C1CCC(C(=O)Nc2ccncc2)CC1]
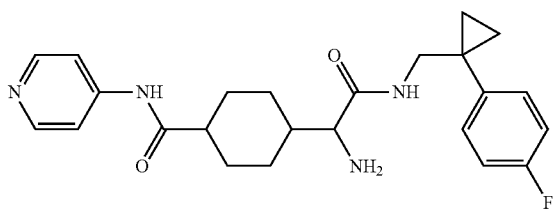

TABLE 1-continued

Compound

TABLE 1-continued
Compound
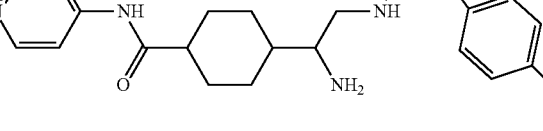
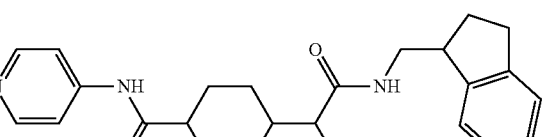
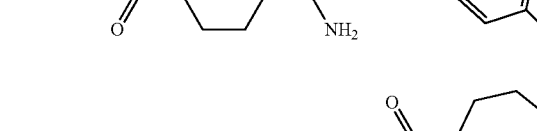
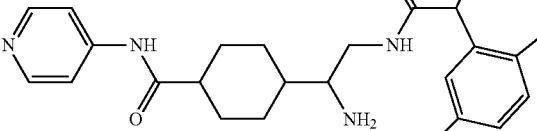
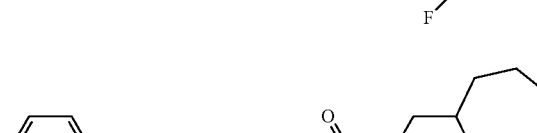
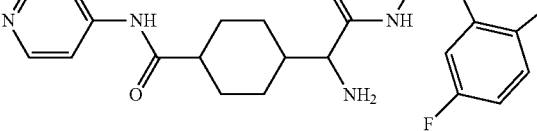
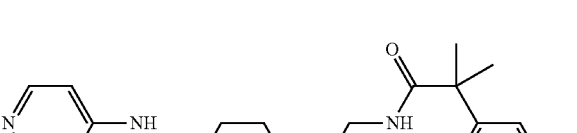

TABLE 1-continued

Compound

TABLE 1-continued

| Compound |
|---|

TABLE 1-continued

Compound

TABLE 1-continued
Compound
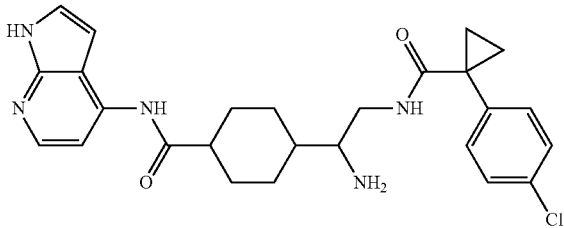 [SMILES: NC(CNC(=O)C1(c2ccc(Cl)cc2)CC1)C1CCC(C(=O)Nc2ccnc3[nH]ccc23)CC1]
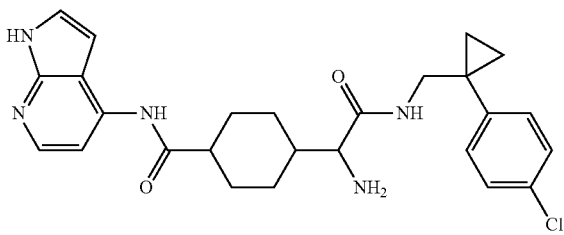
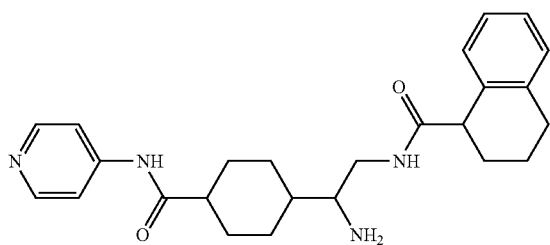 [SMILES: NC(CNC(=O)C1CCCc2ccccc21)C1CCC(C(=O)Nc2ccncc2)CC1]
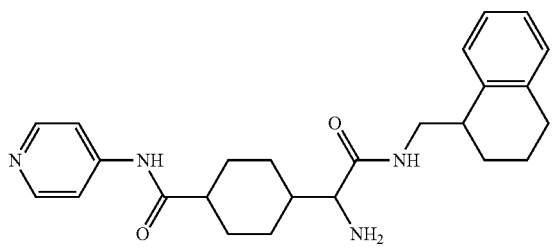
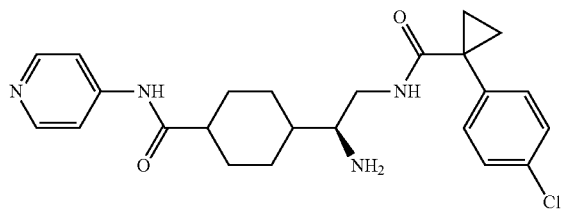
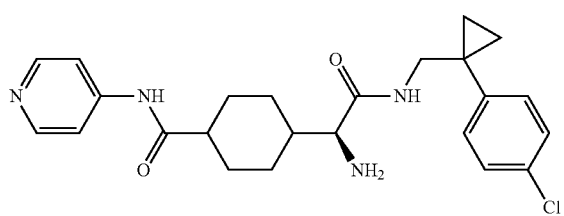

TABLE 1-continued

Compound

139
TABLE 1-continued
Compound
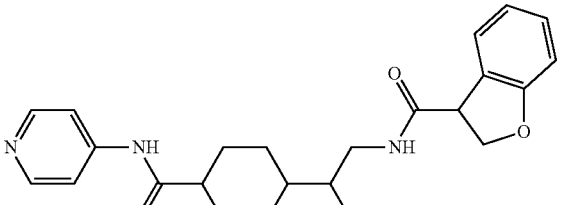
or a salt thereof.
6. The method of claim 1, wherein the compound is selected from Table 2:
TABLE 2
Compound
140
TABLE 2-continued
Compound
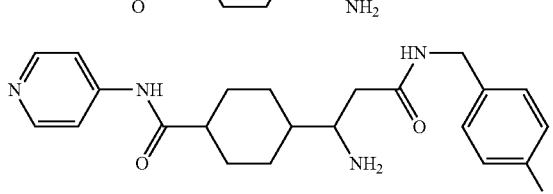

TABLE 2-continued
Compound
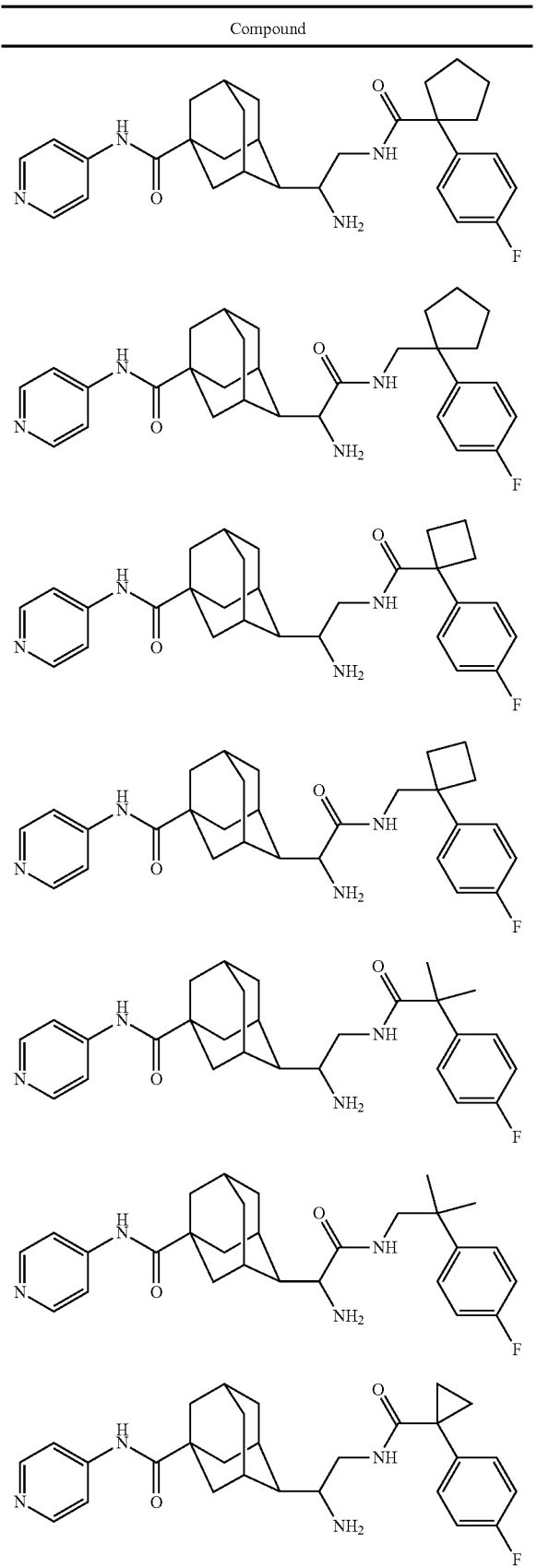
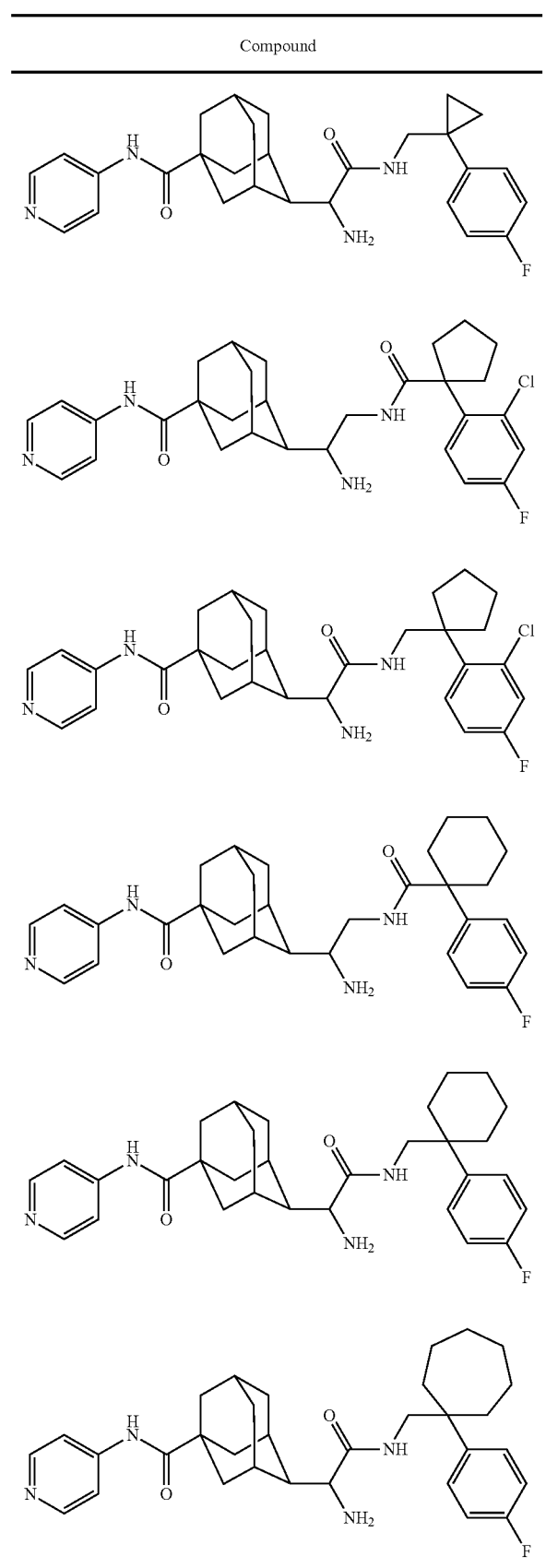

TABLE 2-continued

Compound

TABLE 2-continued
Compound
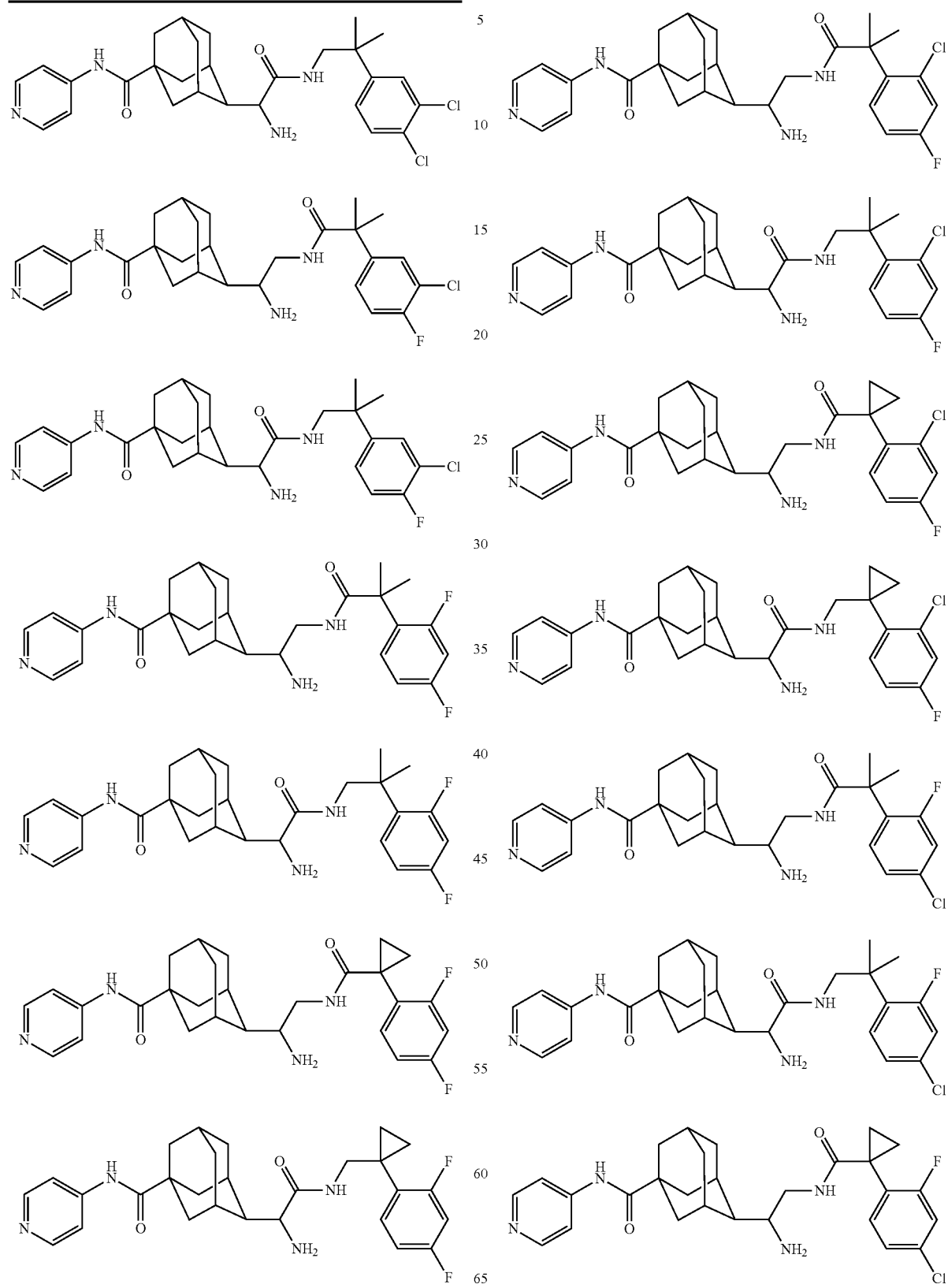

TABLE 2-continued

Compound

TABLE 2-continued
Compound
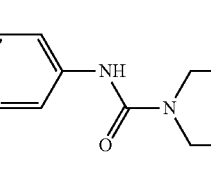
or salt thereof.
7. The method of claim 1, wherein the compound is selected from Table 3:
TABLE 3
Compound
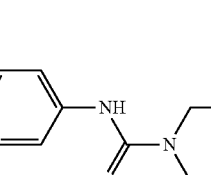
TABLE 3-continued
Compound
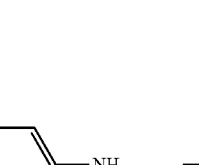

TABLE 3-continued

Compound

TABLE 3-continued
Compound
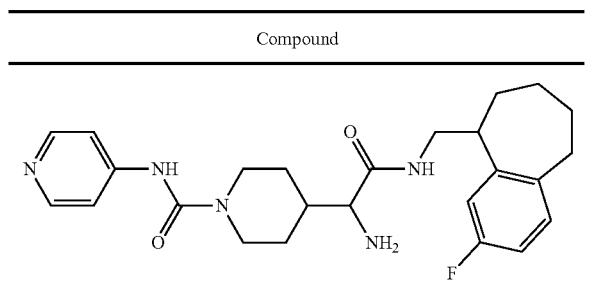
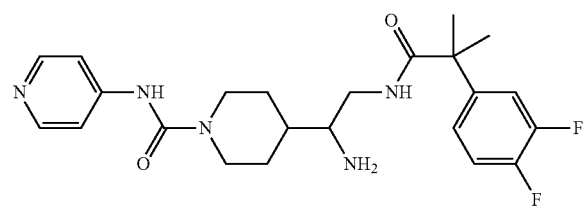
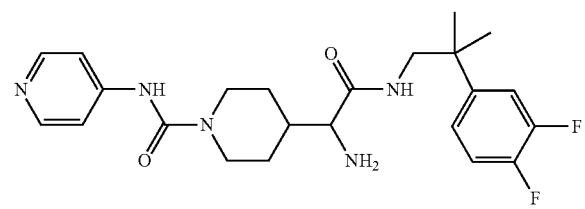 [SMILES: CC(C)(CNC(=O)C(N)C1CCN(C(=O)Nc2ccncc2)CC1)c1ccc(F)c(F)c1]
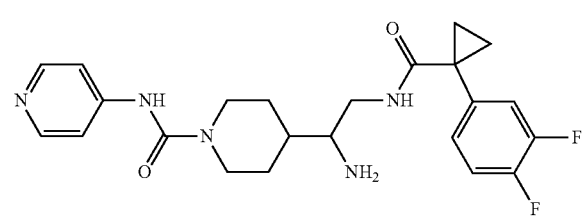 [SMILES: NC(CNC(=O)C1(c2ccc(F)c(F)c2)CC1)C1CCN(C(=O)Nc2ccncc2)CC1]
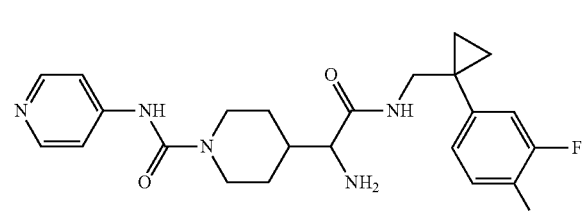
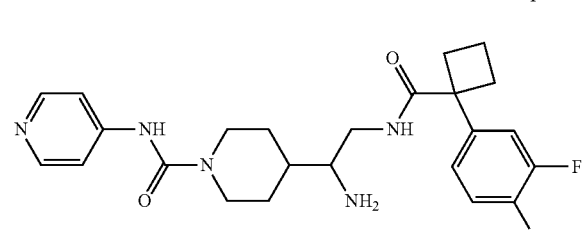
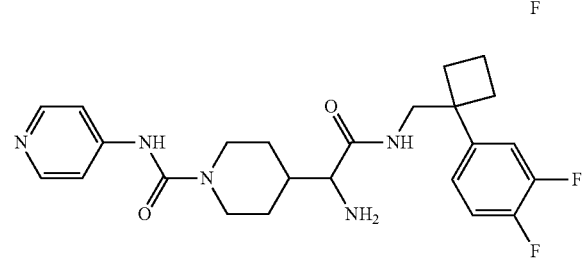
TABLE 3-continued
Compound
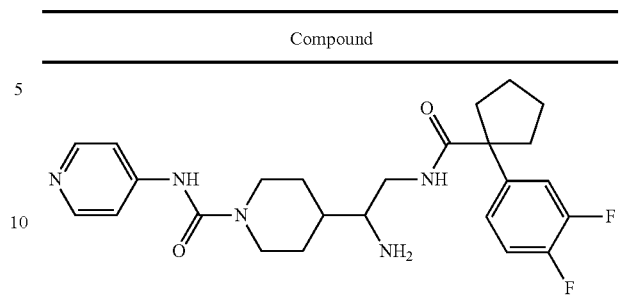
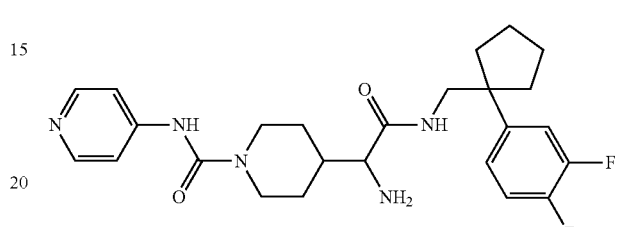
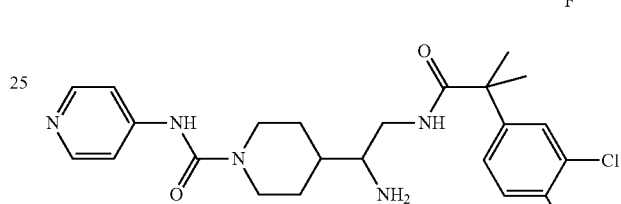
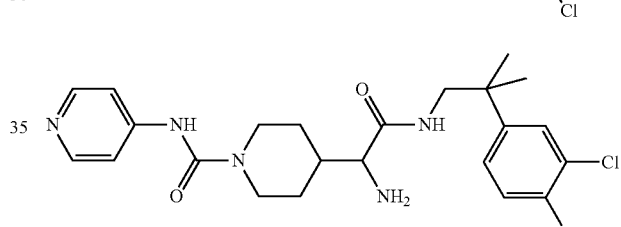
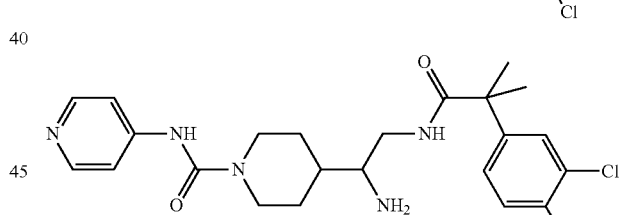
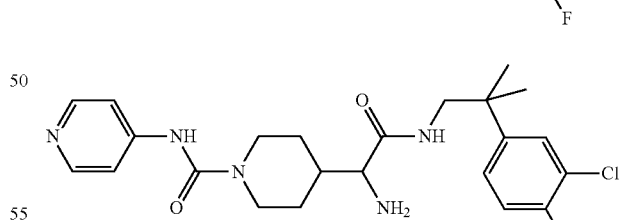
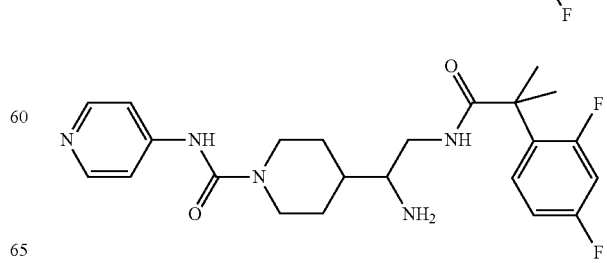

TABLE 3-continued

Compound

TABLE 3-continued
Compound
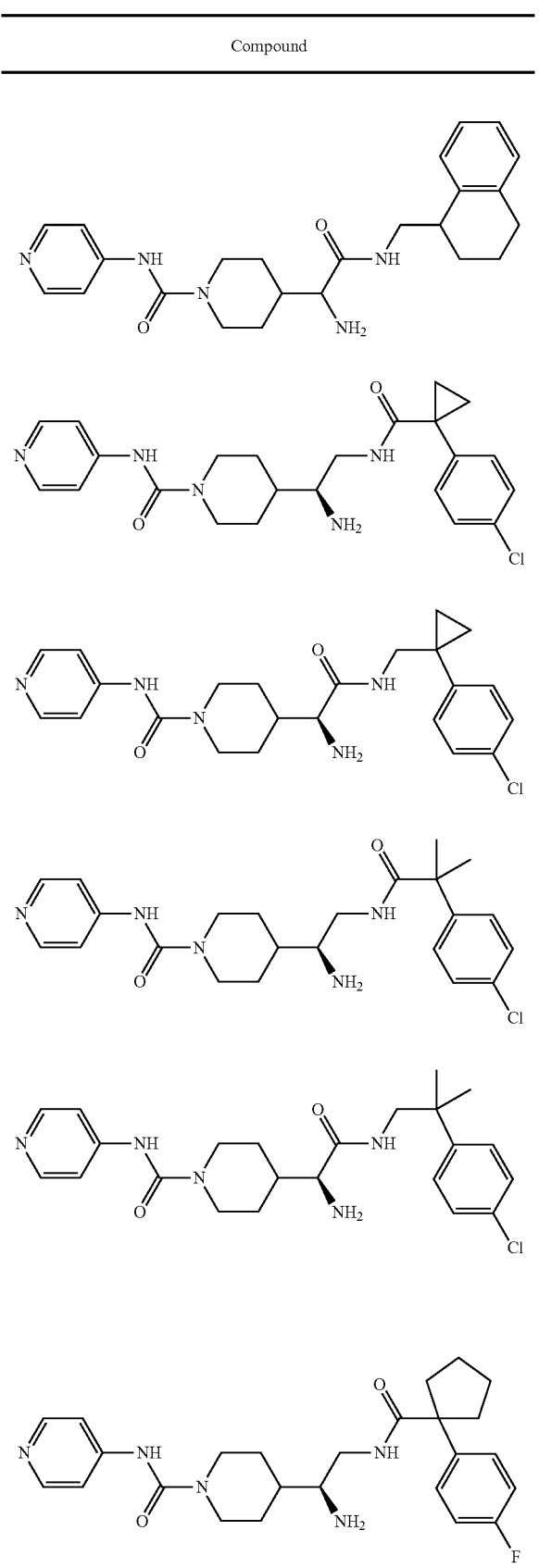
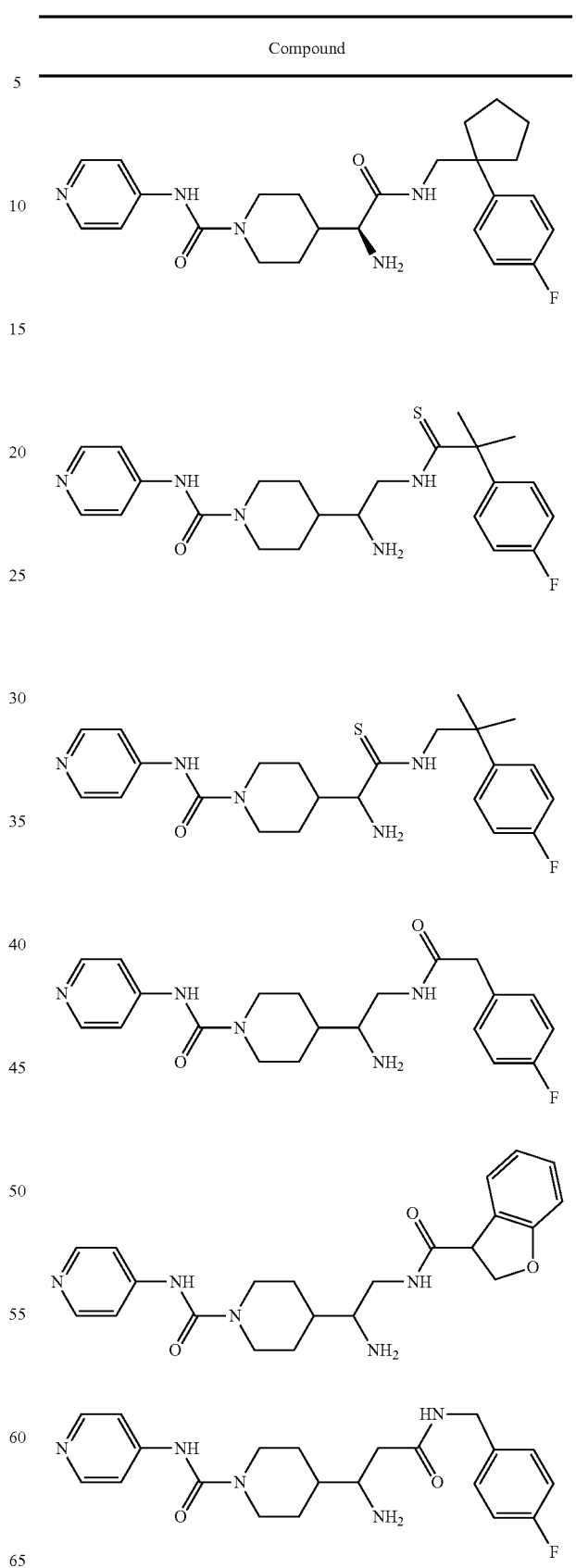

TABLE 3-continued
Compound
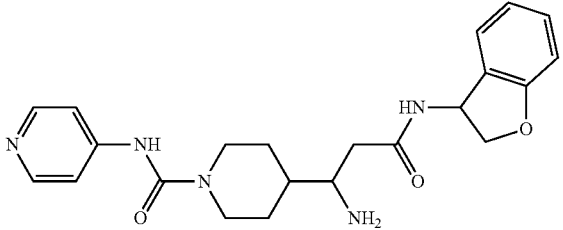
or a salt thereof.
8. The method of claim 1 wherein said patient suffers from substance abuse and/or substance dependence.
9. The method of claim 1 wherein said patient suffers from depression.
* * * * *